(12) United States Patent
Davis et al.

(10) Patent No.: US 7,135,502 B1
(45) Date of Patent: Nov. 14, 2006

(54) COLCHINOL DERIVATIVES AS VASCULAR DAMAGING AGENTS

(75) Inventors: Peter D Davis, Oxfordshire (GB); Jean-Claude Arnould, Reims (FR); Francis T Boyle, Cheshire (GB)

(73) Assignee: Angiogene Pharmaceuticals Ltd., Oxfordshire (GB)

( * ) Notice: Subject to any disclaimer, the term of this patent is extended or adjusted under 35 U.S.C. 154(b) by 0 days.

(21) Appl. No.: 09/869,925

(22) PCT Filed: Dec. 24, 1999

(86) PCT No.: PCT/GB99/04436

§ 371 (c)(1), (2), (4) Date: Aug. 14, 2001

(87) PCT Pub. No.: WO00/40529

PCT Pub. Date: Jul. 13, 2000

(30) Foreign Application Priority Data

Jan. 7, 1999 (GB) .................................. 9900334

(51) Int. Cl.
*A61K 31/05* (2006.01)
(52) U.S. Cl. ........................ 514/732; 514/646; 568/733
(58) Field of Classification Search ................ 514/732, 514/646; 568/733
See application file for complete search history.

(56) References Cited

U.S. PATENT DOCUMENTS

| | | | |
|---|---|---|---|
| 3,442,953 A | 5/1969 | Muller et al. ................. | 568/315 |
| 5,561,122 A | 10/1996 | Pettit ........................... | 514/130 |
| 5,760,092 A | 6/1998 | Timasheff et al. ........... | 514/680 |
| 5,843,910 A | 12/1998 | Bombardelli et al. ......... | 514/33 |
| 5,880,160 A | 3/1999 | Bombardelli et al. ......... | 514/628 |
| 5,973,204 A | 10/1999 | Bombardelli ................. | 564/222 |
| 6,080,739 A | 6/2000 | Bombardelli ............. | 514/229.5 |
| 6,423,753 B1 | 7/2002 | Dougherty .................. | 514/719 |

FOREIGN PATENT DOCUMENTS

| | | |
|---|---|---|
| FR | 4.685 M | 1/1967 |
| JP | 39-19634 | 9/1964 |
| JP | 39-19635 | 9/1964 |
| WO | 97/47577 | 12/1997 |
| WO | 99/02166 | 1/1999 |
| WO | 00/48606 A1 | 8/2000 |
| WO | 02/04434 | 1/2002 |
| WO | 02/08213 | 1/2002 |

OTHER PUBLICATIONS

Boyé et al. "Potential Covalent Markers of the Colchicine-Binding-Site . . . Isothiocyanato Groups", Med. Chem. Res., (1991), 1 (2), 142-150.

Boye et al., "Natural Products. Antitubulin effect of congeners of N-acetylocolchinyl . . . of demethoxy analogues of deaminocolchinyl methyl ether", Can. J. Chem., (1992), 70 (5), 1237-1249.

Boyé et al., "Synthesis of $^{14}C$ Labelled Electrophilic Ligands of the Colchinine . . . 9-Deoxy-N-Acetylcolchinol.",J. Labelled Compd Radiopharm., (1993) 33(4), 293-299.

Mackay et al., "Structures of Colchicine Analogues. IV. An Aminodibromoallocolchicine, $C_{20}H_{22}Br_2 N_2O_4$ ", Acta Crystallogr, Section C: Cryst. Struct Commun, (1991) C47 (12), 2615-2618.

Ondra et al, "Colchicinoide—Ihre Toxizität Und Biologische Activität", Acta Univ Palacki Olomuc Fac Med, (1995) 139, 17-18.

Palmquist et al., "Anodic Oxidation of Phenolic Compounds. 4. $^{1a}$ Scope and Mechanism of the Anodic Intramolecular Coupling of Phenolic Diarylalkanes", J. Am. Chem. Soc., (1976), 98(9), 2571-2580.

Perez-Ramirez et al., "Cosolvent Modulation of the Tubulin-Colchicine GTPase-Activating Conformational Change: Strength of the Enzymatic Activity", Biochemistry, (1994), 33 (20), 6262-6267.

(Continued)

*Primary Examiner*—David Lukton
(74) *Attorney, Agent, or Firm*—Morgan Lewis Bockius LLP

(57) ABSTRACT

The invention relates to the use of compounds of formula (I): wherein X is —C(O)—, —C(S)—, —C=NOH, or —CH($R^7$)— wherein $R^7$ is hydrogen, hydroxy, $C_{1-7}$alkoxy, —$OR^8$ or —$NR^8R^9$ (wherein $R^8$ is a group —$Y^1R^{10}$ (wherein $Y^1$ is a direct bond, —C(O)—, —C(S)—, —S—, —C(O)O, —C(O)$NR^{11}$—, —$SO_2$— or —$SO_2NR^{12}$— (wherein $R^{11}$ and $R^{12}$, which may be the same or different, each independently represents hydrogen, $C_{1-3}$alkyl or $C_{1-3}$alkoxy$C_{2-3}$alkyl) and $R^{10}$ is as defined herein, and $R^9$ includes hydrogen; $R^1$, $R^2$ and $R^3$ are as defined herein and are preferably methyl; $R^4$, $R^5$ and $R^6$ are as defined herein with the proviso that $R^5$ is not hydroxy, alkoxy, substituted alkoxy, —$OPO_3H_2$, —O—$C_{1-7}$alkanoyl or benzyloxy; and salts thereof in the manufacture of a medicament for use in the production of a vascular damaging effect in warm-blooded animals such as humans. The present invention further relates to compounds of the formula (I), pharmaceutical compositions containing them, processes for their preparation and to a method of treatment using the compounds to produce a vascular damaging effect in a warm-blooded animal such as a human. The compounds of formula (I) and the pharmaceutically acceptable salts thereof may be useful in the treatment of a number of disease states including cancer and rheumatoid arthritis.

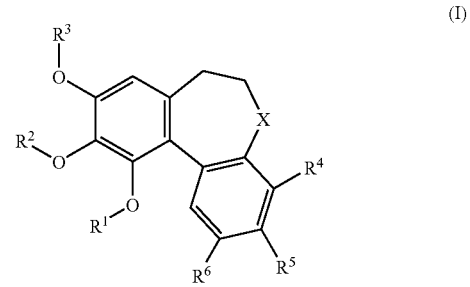

(I)

13 Claims, No Drawings

OTHER PUBLICATIONS

Perez-Ramirez et al., "Linkages in Tubulin-Colchicine Functions: The Roe of Ring C (C') Oxgens and Ring B in the Controls", Biochemistry, (1998), 37 (6), 1646-1661.

Perez-Ramirez et al., "Stoichiometric and Substoichiometric Inhibition of Tubulin Self-Assembly by Colchicine Analogues", Biochemistry, (1996), 35 (10), 3277-3285.

Perez-Ramirez et al., "The Colchicine-Induced GTPase Activity of Tubulin: State of the Product. Activation by Microtubule-Promoting Cosolvents," Biochemistry, (1994), 33 (20), 6253-6261.

Prakash et al., "Aging of Tubulin at Neutral pH: Stabilization by Colchicine and its Analogues", Archives of Biochem & Biophysics (1992), 295 (1), 146-152.

Pyles et al., "Role of the B-Ring Substituent in the Fluorescence of Colchicinoid-Tubulin and Allocolchicinoid-Tubulin Complexes", Biochemistry, (1992), 31 (31), 7086-93.

Rossi et al., "Structural Analysis of the Substoichiometric and Stochiometric Microtubule-Inhibiting Biphenyl Analogues of Colchicine", Biochemistry, (1996), 35 (10), 3286-3289.

Schönharting et al., "Metabolic Transformation of Colchicine I. The Oxidative Formation of Products from Colchicine in the Udenfriend System", Hoppe-Seyler's Z. Physiol.Chem., (1973), 354 (1), 421-436.

Shearwin et al., "Effect of Colchicine Analogues on the Dissociation of $\alpha\beta$ into Subunits: The Locus of Colchicine Binding", Biochemistry, (1994), 33 (4), 894-901.

Shi et al., "Antitumor Agents Part 184[1]) Syntheses and Antibutulin Activity of Compounds Derived from Reaction of Thiocolchicone with Amiens: Lactams, Alcohols, and Ester Analogs of Allothiocolchicinoids", Helv Chim Acta, (1998), 81, 1023-1037.

Shi et al., "Antitumor Agents. 183. Syntheses, Conformational Analyses, and Antitubulin Activity of Allochiocolchicinoids", J. Org. Chem., (1998), 63, 4018-4025.

Shi et al., "Antitumore Agents. 172. Synthesis and Biological Evaluation of Novel Deacetamidothiocolchicin-7-ols and Ester Analogs as Antitubulin Agents", J. Med. Chem., (1997), 40, 961-966.

Staretz et al., "Synthesis, Photochemical Decomposition, and Tubulin Binding of 10-Azido-10-demethoxycolchicine and 9-Azido-9-demethoxyiscocolchicine", J. Org. Chem., (1991) 56 (1), 428-432.

Sterzl et al., "Effect of Colchicine Derivatives on the Antibody Response Induced in vitro", Folia Microbiol. (Prague), (1982), 27 (4), 256-266.

Tang-Wai et al., "Structure Activity Relationships in the Colchicine Molecule with Respect to Interaction with the Mammalian Multidrug Transporter, P-Glycoprotein", Hetercycles, (1994), 39 (1) 385-403.

Timbekov et al., "Mass-Spectometric Study of New Alkaloids from Plants' of the Family Liliaceae", Khim. Prir. Soedin, (1985) (1) 3-11 (in Russian) (English translation attached).

Tojo et al., "The Dibenzocycloheptylamine Alkaloids", J. Nat. Prod., (1989), 52 (5), 1163-1166.

Ward et al., "Energy Transfer Studies of the Distance between the Colchicine, Ruthenium Red, and BisANS Binding Sites on Calf Brain Tubulin", Biochemistry, (1994), 33 (39), 11900-11908.

Ward et al., "Energy-Transfer Studies of the Distance . . . Binding Sites on Calf Brain Tubulin", Biochemistry, (1988), 27 (5), 1508-1514.

Wolff et al., "Cochicine Binding to Antibodies", J. Biol. Chem., (1980) 255 (15), 7144-7148.

Wosikowski et al., "Identification of Epidermal Growth Factor Receptor and c-erbB2 Pathway Inhibitors by Correlation With Gene Expression Patterns", J. Natl. Cancer Inst., (1997), 89 (20) 1505-1515.

Xie et al., "Synthesis of three new Schizandrin Analogues", Chin. Chem. Lett., (1998) 9 (7) 631-634.

Yusupov et al., "A Study of 2-Demethylallocolchicine and Its Derivatives", Khim. Prir. Soedin. (1973), (2), 194-196 (in Russian) (English translation attached).

Zweig et al., "Inhibition of Sodium Urate-Induced Rat Hindpaw Edema by Colchicine Derivatives: Correlation with Antimitotic Activity", J. Pharmacol. Exp. Therapeutics, (1972), 182(2), 344-350.

Zweig et al., "Interaction of Some Colchicine Analogs, Vinblastine and Podphyllotoxin with Rat Brain Microtubule Protein", Biochemistry Pharmacology, (1973), 22, 2141-2150.

Hunter et al., "The photo-oxidation of some novel Colchicine derivatives", Afinidad, vol., 38, No. 372, 1981, pp. 122-123.

Kang et al., "n-acetylcolchinol 0-methyl ether and thiocolchicine, potent nalogs of colchicine modified in the C-ring" Journal of Biological Chemistry, vol. 265, No. 18, Jun. 25, 1990, pp. 10255-10259, XP002081868, ISSN: 0021-9258.

Abu Zarga et al., "New Natural Dibenzocycloheptylamine Alkaloids": A Possible Catabolic Route for the Colchicine Alkaloids, J. Nat. Prod., (1991), 54(4), 936-940.

Al-Tel et al., "New Natural Colchicinoids: Indications of Two Possible Catabolic Routes for the Colchicine Alkaloids", J. Nat. Prod., (1990) 53 (3), 623-629.

Banwell et al., "Total Syntheses of the Structures Assigned to Salimine and Jerusalemine, Alkaloids for *Colchicum decaisnei* Boiss. (Liliaceae)", J. Chem. Soc., Chem. Commun., (1994) (22) 2647-2649.

Banwell, et al., "Synthesis and Tubulin-Binding Properties of Some AC- and ABC-Ring Analogues of Allocolchicine", Aust J Chem., (1992), 45, 1967-1982.

Battersby et al., "Biosynthesis. Part 26[1]. Synthetic Studies on Structural Modification of Late Biosynthetic Precursors for Colchicine", J. Chem. Soc., Perkin Trans 1, (1983), (12), 3053-3063.

Boger et al., "Thermal Reactions of Cyclopropenone Ketals. Application of . . . Total Synthesis of Colchicine", J. Am. Chem. Soc., (1986) (108 (21), 6713-6719.

Boyé et al. "185. Deaminocolchinyl Methyl Ether: Synthesis from . . . Errfects of Deaminocolchinyl Methyl Ether and Dehydro Analogs", Helv. Chem. Acta, (1989), 72 (8), 1690-1696.

Brecht et al., "(−)-(M,7S)-Colchicine and (−)-(M,7S)-10-Ethylthiocolchicide/Alkyne . . . Consecutive [4+2] and [3 +2] Cycloadditions", Eur. Jour. Org. Chem., (1998) (11) 2451-2460.

Brossi et al., "aS, 7S-absolute configuration of natural --)-colchicine and allocongeners", FEBS Lett., (1990), 262 (1), 5-7.

Orsini et al (1997) Carbohydrate Research 301, 95-109.

Brown el al (1995) J. Chem. Soc. Perkin. Trans. 1 577-581.

Deninim et al., "Synthesis and Binding to Tubulin of an Allocolchicine Spin Probe." Acta Chem. Scand, Ser B (1981) B35 (10), 677-681.

Dilger et al., "Arbeitsvorschriften und Messwerte Procedures and Data Formaldehyd-O-oxid und Colchicine: ein eleganter Zugang zu Allocolcicinen", J. Prakt Chem./Chem-Ztg, (1998), 340 (5), 468-471 (in German).

Dumortier et al., "Alternations of Rings B and C of Colchicine Are Cumulative in Overall Binding to Tubulin but Modify Each Kinetic Step", Biochemistry, (1996), 35 (49), 15900-15906.

Fitzgerald, "Molecular Features of Colchicine Associated with Antimitotic Activity and Inhibition of Tubulin Polymerization", Biochemistry Pharmacology, (1976), 25, 1383-1387.

Ghera et al., "Total Synthesis of Lignan (±)-Schizandrin", J. Chem. Soc., Chem. Commun., (1978) (11), 480-481.

Hahn et al., "Synthesis and Evaluation of 2-Diazo-3,3,3-Trifluoropropanoyl . . . Photochemistry, and Tubulin Binding", Photochem. Photobiol., (1992) 55 (1), 17-27.

Han et al., "Distances between the Paclitaxel, Colchicine, and Exhangeable GTP Binding Site on Tubulin", Biochemistry, (1998), 37 (19), 6636-6644.

Leiter et al., "Damage Induced in Sarcoma 37 with Chemical Agents. III. Colchicine Derivatives Related to Trimethylcolchicinic Acid and to Colchinol", J. Natl. Cancer Inst., (1952), 13, 379-392.

Medrano, "Roles of Colchicine Rings B and C in the Binding Process to Tubulin", Biochemistry, (1989), 28 (13), 5589-5599.

Menéndez et al., " A Thermodynamic Study of the Interaction of Tubulin with Colchicine Site Ligands", J. Biol. Chem., (1989), 264, (28), 16367-16371.

Olszewski et al., "Potential Photoaffinity Labels for Tubulin. Synthesis and . . . Colchicine, Combretastatin, and 3,4,5-Trimethoxybiphenyl", J. Org. Chem., (1994), 59 (15) 4285-4296.

Powell et al., "Role of Ring C Substituents Related to Allocolchicine on Antitubulin Action", Med. Chem. Res., (1996), 164-173.

Mackey et al., "Structures of Colchicine Analogues. I. Allocolchicine", Acta Cryst, (1989), C45, 795-799.

Hastie, "Spectroscopic analyses of colchicinoid-tubulin complexes", Cellular Pharmacology, (1993), 1, (Suppl. 1), S17-S21.

Hastie, "Spectroscopic and Kinetic Features of Allocolchicine Binding to Tubulin", Biochemistry, (1989), 28 (19), 7753-7760.

Hrbek et al., "Circular Dichroism of Alkaloids of Colchicine Type And Their Derivatives", Collect. Czech. Chem. Commun., (1982), 47 (8), 2258-2279.

Iorio, "Contraction of the Tropolonic Ring of Colchicine by Hydrogen Peroxide Oxidation", Heterocycles, (1984), 22 (10), 2207-2211.

Kiselev et al., "Benzenoid Rearrangement of Colchicine by the Action of Ethylene Glycol", Zh. Org. Khim., (1977), 13 (11), 2337-2342 (in Russian) (English translation attached).

Kiselev et al., "Derivatives of Aminocolchicide—VI. Dicolchicidyl-L-Lysine" Obshch. Khim., (1970), 40 (4), 914-915 (in Russian, English translation attached).

Kiselev, "Derivatives of Aminocolchicide. VII", Zh. Zh. Obshch.. Khim., (1971), 41 (2) 464-466 (in Russian, English translation attached).

Kita et al., "Non-phenolic oxidative coupling of phenol ether derivatives using phenyliodine (III) bis(trifluoroacetate)", Chem. Commun. (Cambridge), (1996) (12), 1481-1482.

English language Abstract of Dokl Akad Nauk USSR, (1991) (4) 33-35.

English language Abstract of Fernholz, "Über die Umlagerung des Colchicins mit Natriumalkoholat und die Struktur des Ringes $C^1$)", Justus Liebigs Ann. Chem., CODEN: JLACBF, 568, (1950), 63-82.

English language Abstract of Zh Obshch Khim., (1994) 64(5) 856-864 (in Russian).

English language Abstract of Timbekov et al., "Mass Spectrometric Study of Alkaloids of the Homoaprophine, Homomorpine and Allocolchicine Series", Tezisy Dokl.=Sov.-Indiiskii Simp. Khim. Prir Soedin., 5th (1978), p. 85 (Chemical Abstracts attached).

English language Abstract of Izv Akad Nauk Turkm SSR, Ser Fiz-Tekh, Khim Geol Nauk, (1976), (1), 70-73.

Brecht et al., "Dihydrocolchicine 8,12-Endoperoxide: A Novel Starting Material for Convenient Syntheses of the Allocolchicinoids N-Acetylcolchinol-O-Methyl Ether and Androbiphenyline"; Liebigs Ann. Recueil, 1997, pp. 2275-2279.

COLCHINOL DERIVATIVES AS VASCULAR DAMAGING AGENTS

This application is a 371 of PCT/GB99/04436, filed Dec. 24, 1999, which claims priority to UK application 9900334.5, filed Jan. 7, 1999.

The present invention relates to vascular damaging agents, in particular to the use of compounds of the invention in the manufacture of medicaments for use in the production of antiangiogenic effects in warm-blooded animals such as humans, to processes for the preparation of such compounds, to pharmaceutical compositions containing such compounds as active ingredient, to methods for the treatment of disease states associated with angiogenesis and to the use of such compounds as medicaments.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 26: 57–66; Folkman, 1995, Nature Medicine 1: 27–31). Formation of new vasculature by angiogenesis is a key pathological feature of several diseases (J. Folkman, New England Journal of Medicine 333, 1757–1763 (1995)). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy.

Reversal of neovascularisation by damaging the newly-formed vascular endothelium is expected to have a beneficial therapeutic effect. The present invention is based on the discovery of tricyclic compounds that surprisingly specifically damage newly formed vasculature without affecting the normal, established vascular endothelium of the host species, a property of value in the treatment of disease states associated with angiogenesis such as cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation.

Compounds of the present invention are colchinol derivatives. Colchinol derivatives for example N-acetyl-colchinol are known. Anti-tumour effects have been noted on animal models (see for example—Jnl. Natl. Cancer Inst. 1952, 13, 379–392). However, the effect studied was that of gross damage (haemorrhage, softening and necrosis) and there is no suggestion of treatment of inappropriate angiogenesis by destruction of neovasculature.

A search of Chemical Abstracts (post 1955) based on the substructure:

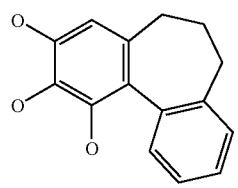

revealed a number of colchinol related structures. To the extent that any of these compounds have been studied for anti-cancer activity it is because tubulin-binding agents like colchinol might be expected to be anti-mitotic and therefore to have a direct effect on tumour cells. Some compounds which bind tubulin have been shown to have anti-vascular effects when given at their maximum tolerated dose (MTD) (S. A. Hill et al. Eur. J Cancer, 29A, 1320–1324 (1993)) but other tubulin-binding agents have no vascular-damaging activity even when administered at the MTD, for example docetaxel (Lancet, 1994, 344, 1267–1271). Based on this information and in the course of the work in the present invention, the issue of the relevance of tubulin-binding properties to possible effectiveness as anti-vascular agent was studied but no predictability was found. No correlation between the potency of tubulin interaction and effectiveness as an anti-vascular agent is apparent. Certain compounds structurally related to those of the present invention but not of the present invention, have been found to have a therapeutic window (ratio of MTD to minimum effective dose (MED)) too small for potential clinical effectiveness.

The presence of tubulin-binding properties is then not predictive for antivascular activity. Compounds which have strong tubulin-binding activity give rise to antimitotic effects in vivo. The effects of this are most noticeable on proliferating tissue and give rise to undesirable effects, for example on the proliferative tissue of the gut and bone marrow. Compounds which have vascular damaging activity but weak tubulin-binding activity would therefore be useful in the treatment of diseases involving angiogenesis.

It is believed, though this is not limiting on the invention, that the use of compounds of the invention damages newly-formed vasculature, for example the vasculature of tumours, thus effectively reversing the process of angiogenesis as compared to known anti-angiogenic agents which tend to be less effective once the vasculature has formed.

According to one aspect of the present invention there is provided the use of a compound of formula I:

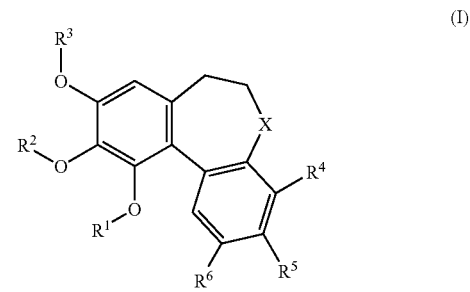

(I)

wherein
X is —C(O)—, —C(S)—, —C=NOH, or —CH($R^7$)— wherein $R^7$ is hydrogen, hydroxy, $C_{1-7}$alkoxy, —$OR^8$ or —$NR^8R^9$ (wherein $R^8$ is a group —$Y^1R^{10}$ (wherein $Y^1$ is a direct bond, —C(O)—, —C(S)—, —S—, —C(O)O—, —C(O)$NR^{11}$—, —$SO_2$— or —$SO_2NR^{12}$— (wherein $R^{11}$ and $R^{12}$, which may be the same or different, each independently represents hydrogen, $C_{1-3}$alkyl or $C_{1-3}$alkoxy$C_{2-3}$alkyl) and $R^{10}$ is selected from one of the following nine groups:

1) hydrogen, $C_{1-7}$alkyl, $C_{3-7}$cycloalkyl, $C_{1-4}$alkyl$Y^8$ $C_{1-4}$alkyl wherein $Y^8$ is as defined hereinafter, or phenyl, (which alkyl, cycloalkyl, alkyl$Y^8$alkyl or phenyl group may bear one or more substituents selected from:
  halogeno, amino, $C_{1-4}$alkylamino, di($C_{1-4}$alkyl)amino, hydroxy, carboxy, carbamoyl, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, phenyl, nitro, sulphate, phosphate, $Z^1$ (wherein $Z^1$ represents a 5–6 membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-7}$alkanoyl, cyano$C_{1-4}$alkyl, $C_{1-4}$alkoxy$C_{1-4}$alkyl, $C_{1-4}$alkylsulphonyl$C_{1-4}$alkyl and $Z^2$ (wherein $Z^2$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-7}$alkanoyl, cyano$C_{1-4}$alkyl, $C_{1-4}$alkoxy$C_{1-4}$alkyl and $C_{1-4}$alkylsulphonyl$C_{1-4}$alkyl)), $C_{1-4}$alkyl$Z^1$ (wherein $Z^1$ is as defined hereinbefore), and a group —$Y^2R^{13}$ (wherein $Y^2$ is —$NR^{14}C(O)$— or —O—C(O)— (wherein $R^{14}$ represents hydrogen, $C_{1-3}$alkyl or $C_{1-3}$alkoxy$C_{2-3}$alkyl) and $R^{13}$ is $C_{1-7}$alkyl, $C_{3-7}$cycloalkyl or a group $R^{15}$ wherein $R^{15}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{16}R^{17}$ and —$NR^{18}COR^{19}$ (wherein $R^{16}$, $R^{17}$, $R^{18}$ and $R^{19}$, which may be the same or different, each represents hydrogen, $C_{1-3}$alkyl or $C_{1-3}$alkoxy$C_{2-3}$alkyl)));

2) $R^{15}$ wherein $R^{15}$ is as defined hereinbefore;
3) $C_{2-7}$alkenyl$R^{15}$ (wherein $R^{15}$ is as defined hereinbefore);
4) $C_{3-7}$alkynyl$R^{15}$ (wherein $R^{15}$ is as defined hereinbefore));
5) $Z^1$ (wherein $Z^1$ is as defined hereinbefore);
6) $C_{1-7}$alkyl$Z^1$ (wherein $Z^1$ is as defined hereinbefore);
7) $C_{1-7}$alkyl$Y^8Z^1$ (wherein $Z^1$ is as defined hereinbefore and $Y^8$ is —C(O)—, —$NR^{59}C(O)$—, —$NR^{59}C(O)C_{1-4}$alkyl-, —$C(O)NR^{60}$— or —$C(O)NR^{60}C_{1-4}$alkyl-, (wherein $R^{59}$ and $R^{60}$, which may be the same or different, each represents hydrogen, $C_{1-3}$alkyl, $C_{1-3}$hydroxyalkyl or $C_{1-3}$alkoxy$C_{2-3}$alkyl));
8) $(C_{1-7}\text{alkyl})_cY^9Z^3$ (wherein c is 0 or 1, $Z^3$ is an amino acid group and $Y^9$ is a direct bond, —C(O)— or —$NR^{61}$— (wherein $R^{61}$ is hydrogen, $C_{1-3}$alkyl or $C_{1-3}$alkoxy$C_{2-3}$alkyl)); and
9) $C_{1-7}$alkyl$R^{15}$ (wherein $R^{15}$ is as defined hereinbefore);

and $R^9$ is hydrogen, $C_{1-7}$alkyl or $C_{3-7}$cycloalkyl, which alkyl or cycloalkyl group may bear one or more selected from $C_{1-4}$alkoxy and phenyl);

$R^1$, $R^2$ and $R^3$ are each independently hydrogen, $PO_3H_2$, sulphate, $C_{3-7}$cycloalkyl, $C_{2-7}$alkenyl, $C_{2-7}$alkynyl, $C_{1-7}$alkanoyl, a group $R^{20}C_{1-7}$alkyl (wherein $R^{20}$ is phenyl which may bear one or more substituents selected from $C_{1-4}$alkyl, $C_{1-4}$alkoxy, $C_{1-4}$aminoalkyl and $C_{1-4}$hydroxyalkoxy), $C_{1-7}$alkyl or $C_{1-7}$alkylsulphonyl (which alkyl or alkylsulphonyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^2R^{21}$ (wherein $Y^2$ is —$NR^{22}C(O)$— or —O—C(O)— (wherein $R^{22}$ represents hydrogen, $C_{1-3}$alkyl or $C_{1-3}$alkoxy$C_{2-3}$alkyl) and $R^{21}$ is $C_{1-7}$alkyl, $C_{3-7}$cycloalkyl or a group $R^{23}$ wherein $R^{23}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{24}R^{25}$ and —$NR^{26}COR^{27}$ (wherein $R^{24}$, $R^{25}$, $R^{26}$ and $R^{27}$, which may be the same or different, each represents hydrogen, $C_{1-3}$alkyl or $C_{1-3}$alkoxy$C_{2-3}$alkyl)));

with the proviso that at least two of $R^1$, $R^2$ and $R^3$ are $C_{1-7}$alkyl;

$R^4$, $R^5$ and $R^6$ are each independently selected from:

hydrogen, —$OPO_3H_2$, phosphonate, cyano, halogeno, nitro, amino, carboxy, carbamoyl, hydroxy, $C_{1-7}$alkoxy, $C_{1-7}$alkanoyl, $C_{1-7}$thioalkoxy, $C_{1-7}$alkyl, (which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, sulphate, phosphate and a group —$Y^3R^{28}$ (wherein $Y^3$ is —$NR^{29}C(O)$— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl))), and a group —$Y^4R^{35}$ (wherein $Y^4$ is —C(O)—, —OC(O)—, —O—, —SO—, —$SO_2$—, —$OSO_2$—, —$NR^{36}$—, —$C_{1-4}$alkyl$NR^{36}$—, —$C_{1-4}$alkylC(O)—, —$NR^{37}C(O)$—, —OC(O)O—, —$C(O)NR^{38}$— or —$NR^{39}C(O)O$— (wherein $R^{36}$, $R^{37}$, $R^{38}$ and $R^{39}$, which may be the same or different, each represents hydrogen, $C_{1-3}$alkyl or $C_{1-3}$alkoxy$C_{2-3}$alkyl) and $R^{35}$ is a sugar moiety, a mono-peptide, a di-peptide, a tri-peptide, a tetra-peptide, sulphate, hydroxy, amino, $C_{1-7}$alkyl, $C_{1-7}$alkoxy, $C_{1-7}$alkanoyl, $C_{1-7}$alkylamino, di($C_{1-7}$alkyl)amino, amino$C_{1-7}$alkylamino, $C_{1-7}$alkylamino$C_{1-7}$alkylamino, $C_{1-7}$alkanoylamino$C_{1-7}$alkyl, di($C_{1-7}$alkyl)amino$C_{1-7}$alkylamino, $C_{1-7}$alkylphosphate, $C_{1-7}$alkylphosphonate, $C_{1-7}$alkylcarbamoyl$C_{1-7}$alkyl, (which alkyl, alkoxy, alkanoyl, alkylamino, dialkylamino, aminoalkylamino, alkylaminoalkylamino, alkanoylaminoalkyl, dialkylaminoalkylamino, alkylphosphate, alkylphosphonate or alkylcarbamoylalkyl, may bear one or more substituents selected from:

halogeno, amino, $C_{1-4}$alkylamino, di($C_{1-4}$alkyl)amino, hydroxy, $C_{1-4}$hydroxyalkyl, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^5R^{40}$ (wherein $Y^5$ is —$NR^{41}C(O)$—, —$C(O)NR^{42}$—, —$C(O)$—O— or —O—$C(O)$— (wherein $R^{41}$ and $R^{42}$ which may be the same or different each represents hydrogen, $C_{1-3}$alkyl or $C_{1-3}$alkoxy$C_{2-3}$alkyl) and $R^{40}$ is $C_{1-7}$alkyl, $C_{3-7}$cycloalkyl, carboxy$C_{1-7}$alkyl or a group $R^{43}$ wherein $R^{43}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{44}R^{45}$ and —$NR^{46}COR^{47}$ (wherein $R^{44}$, $R^{45}$, $R^{46}$ and $R^{47}$, which may be the same or different, each represents hydrogen, $C_{1-3}$alkyl or $C_{1-3}$alkoxy$C_{2-3}$alkyl))), $R^{48}$ (wherein $R^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, di($C_{1-4}$alkyl)amino, di($C_{1-4}$ alkyl)amino$C_{1-4}$alkyl, di($C_{1-4}$hydroxyalkyl)amino$C_{1-4}$alkyl, di($C_{1-4}$aminoalkyl)amino$C_{1-4}$alkyl, $C_{1-4}$hydroxyalkoxy, carboxy, $C_{1-4}$carboxyalkyl, phenyl, cyano, —$CONR^{49}R^{50}$, —$NR^{51}COR^{52}$ (wherein $R^{49}$, $R^{50}$, $R^{51}$ and $R^{52}$, which may be the same or different, each represents hydrogen, $C_{1-3}$alkyl or $C_{1-3}$alkoxy$C_{2-3}$alkyl) and $C_{1-4}$alkyl$R^{53}$ (wherein $R^{53}$ is as defined hereinafter), $C_{1-7}$alkyl$R^{48}$ (wherein $R^{48}$ is as defined hereinbefore), $R^{53}$ (wherein $R^{53}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$carboxyalkyl, $C_{1-4}$aminoalkyl, di($C_{1-4}$alkyl)amino$C_{1-4}$alkyl, $C_{1-4}$alkoxy$C_{1-4}$alkyl, $C_{1-4}$alkylsulphonyl$C_{1-4}$alkyl and $R^{54}$ (wherein $R^{54}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl)), or $(CH_2)_aY^6(CH_2)_bR^{53}$ (wherein $R^{53}$ is as defined hereinbefore, a is 0, or an integer 1–4, b is 0 or an integer 1–4 and $Y^6$ represents a direct bond, —O—, —$C(O)$—, —$NR^{55}$—, —$NR^{56}C(O)$— or —$C(O)NR^{57}$— (wherein $R^{55}$, $R^{56}$, and $R^{57}$, which may be the same or different, each represents hydrogen, $C_{1-3}$alkyl or $C_{1-3}$alkoxy$C_{2-3}$alkyl), and wherein one or more of the $(CH_2)_a$ or $(CH_2)_b$ groups may bear one or more substituents selected from hydroxy, amino and halogeno));

with the proviso that $R^5$ is not hydroxy, alkoxy, substituted alkoxy (wherein $R^5$ is $Y^4R^{35}$ and $Y^4$ is —O— and $R^{35}$ is $C_{1-7}$alkyl bearing one or more substituents selected from the list given hereinbefore), —$OPO_3H_2$, —O—$C_{1-7}$alkanoyl or benzyloxy;

and salts thereof, pharmaceutically acceptable salts thereof, solvates and hydrates thereof, and prodrugs thereof in the manufacture of a medicament for use in the production of a vascular damaging effect in warm-blooded animals such as humans.

According to a further aspect of the present invention there is provided the use of a compound of the formula I as defined hereinbefore and salts thereof, pharmaceutically acceptable salts thereof, solvates and hydrates thereof, and prodrugs thereof in the manufacture of a medicament for use in the production of a vascular damaging effect at less than the maximum tolerated dose in warm-blooded animals such as humans. Conveniently X is —$C(O)$—, —$C(S)$— or —$CH(R^7)$— wherein $R^7$ is hydrogen, hydroxy, —$OR^8$ or —$NR^8R^9$ (wherein $R^8$ is a group —$Y^1R^{10}$ (wherein $Y^1$ is a direct bond, —$C(O)$—, —$C(S)$—, —S—, —$C(O)O$—, —$C(O)NR^{11}$—, —$SO_2$— or —$SO_2NR^{12}$— (wherein $R^{11}$ and $R^{12}$, which may be the same or different, each independently represents hydrogen, $C_{1-3}$alkyl or $C_{1-3}$alkoxy$C_{2-3}$alkyl) and $R^{10}$ is selected from one of the following seven groups:

1) hydrogen, $C_{1-7}$alkyl, $C_{3-7}$cycloalkyl, $C_{1-4}$alkyl$Y^8C_{1-4}$alkyl wherein $Y^8$ is as defined hereinafter, or phenyl, (which alkyl, cycloalkyl, alkyl$Y^8$alkyl or phenyl group may bear one or more substituents selected from:

halogeno, amino, $C_{1-4}$alkylamino, di($C_{1-4}$alkyl)amino, hydroxy, carboxy, carbamoyl, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, phenyl, nitro, sulphate, phosphate, $Z^1$ (wherein $Z^1$ represents a 5–6 membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-7}$alkanoyl, cyano$C_{1-4}$alkyl, $C_{1-4}$alkoxy$C_{1-4}$alkyl, $C_{1-4}$alkylsulphonyl$C_{1-4}$alkyl and $Z^2$ (wherein $Z^2$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-7}$alkanoyl, cyano$C_{1-4}$alkyl, $C_{1-4}$alkoxy$C_{1-4}$alkyl and $C_{1-4}$alkylsulphonyl$C_{1-4}$alkyl)), $C_{1-4}$alkyl$Z^1$ (wherein $Z^1$ is as defined hereinbefore), and a group —$Y^2R^{13}$ (wherein $Y^2$ is —$NR^{14}C(O)$— or —O—$C(O)$— (wherein $R^{14}$ represents hydrogen, $C_{1-3}$alkyl or $C_{1-3}$alkoxy$C_{2-3}$alkyl) and $R^{13}$ is $C_{1-7}$alkyl, $C_{3-7}$cycloalkyl or a group $R^{15}$ wherein $R^{15}$ is a 5–10-membered aromatic heterocyclic group (linked via carbon or nitrogen) with 1–4 heteroatoms selected independently from O, N and S, aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —CONR$^{16}$R$^{17}$ and —NR$^{18}$COR$^{19}$ (wherein R$^{16}$, R$^{17}$, R$^{18}$ and R$^{19}$, which may be the same or different, each represents hydrogen, C$_{1-3}$alkyl or C$_{1-3}$alkoxyC$_{2-3}$alkyl)));
2) R$^{15}$ wherein R$^{15}$ is as defined hereinbefore;
3) Z$^1$ (wherein Z$^1$ is as defined hereinbefore);
4) C$_{1-7}$alkylZ$^1$ (wherein Z$^1$ is as defined hereinbefore);
5) C$_{1-7}$alkylY$^8$Z$^1$ (wherein Z$^1$ is as defined hereinbefore and Y$^8$ is —C(O)—, —NR$^{59}$C(O)—, —NR$^{59}$C(O)C$_{1-4}$alkyl-, —C(O)NR$^{60}$— or —C(O)NR$^{60}$C$_{1-4}$alkyl-, (wherein R$^{59}$ and R$^{60}$, which may be the same or different, each represents hydrogen, C$_{1-3}$alkyl, C$_{1-3}$hydroxyalkyl or C$_{1-3}$alkoxyC$_{2-3}$alkyl));
6) (C$_{1-7}$alkyl)$_c$Y$^9$Z$^3$ (wherein c is 0 or 1, Z$^3$ is an amino acid group and Y$^9$ is a direct bond, —C(O)— or —NR$^{61}$— (wherein R$^{61}$ is hydrogen, C$_{1-3}$alkyl or C$_{1-3}$alkoxyC$_{2-3}$alkyl)); and
7) C$_{1-7}$alkylR$^{15}$ (wherein R$^{15}$ is as defined hereinbefore));
and R$^9$ is hydrogen, C$_{1-7}$alkyl or C$_{3-7}$cycloalkyl, which alkyl or cycloalkyl group may bear one or more substituents selected from C$_{1-4}$alkoxy and phenyl).

Advantageously X is —CH(R$^7$)— wherein R$^7$ is —OR$^8$ or —NR$^8$R$^9$ (wherein R$^8$ is a group —Y$^1$R$^{10}$ (wherein Y$^1$ is —C(O)—, —C(O)O— or —C(O)NR$^{11}$— (wherein R$^{11}$ represents hydrogen, C$_{1-3}$alkyl or C$_{1-3}$alkoxyC$_{2-3}$alkyl) and R$^{10}$ is as defined hereinbefore) and R$^9$ is as defined hereinbefore).

Preferably X is —CH(R$^7$)— wherein R$^7$ is —OR$^8$ or —NR$^8$R$^9$ (wherein R$^8$ is a group —Y$^1$R$^{10}$ (wherein Y$^1$ is —C(O)— or —C(O)O— and R$^{10}$ is as defined hereinbefore) and R$^9$ is as defined hereinbefore).

In one embodiment of the present invention preferably X is —C(O)—, —CH$_2$—, —CH(OH)— or —CH(NHC(O)CH$_3$)—.

In one embodiment of the present invention more preferably X is —CH(NHC(O)CH$_3$)—.

Conveniently R$^1$, R$^2$ and R$^3$ are each independently hydrogen, PO$_3$H$_2$, sulphate, C$_{1-7}$alkyl, C$_{3-7}$cycloalkyl, C$_{2-7}$alkenyl, C$_{2-7}$alkynyl, C$_{1-7}$alkanoyl, C$_{1-7}$alkylsulphonyl or a group R$^{20}$C$_{1-7}$alkyl (wherein R$^{20}$ is phenyl which may bear one or more substituents selected from C$_{1-4}$alkyl, C$_{1-4}$alkoxy, C$_{1-4}$aminoalkyl and C$_{1-4}$hydroxyalkoxy); with the proviso that at least two of R$^1$, R$^2$ and R$^3$ are C$_{1-7}$alkyl.

Preferably R$^1$, R$^2$ and R$^3$ are each independently C$_{1-4}$alkyl.
More preferably R$^1$, R$^2$ and R$^3$ are each methyl.

Conveniently R$^4$ is hydrogen, cyano, halogeno, nitro, amino, hydroxy, C$_{1-7}$alkoxy, C$_{1-7}$thioalkoxy, C$_{1-7}$alkanoyl or C$_{1-7}$alkyl,
(which alkyl group may bear one or more substituents selected from halogeno, amino, C$_{1-4}$alkylamino, di(C$_{1-4}$ alkyl)amino, hydroxy, C$_{1-4}$alkoxy, C$_{1-4}$alkylsulphanyl, C$_{1-4}$alkylsulphonyl, C$_{1-4}$alkoxycarbonylamino, C$_{1-4}$alkanoyl, carboxy, phenyl, nitro, sulphate, phosphate and a group —Y$^3$R$^{28}$ (wherein Y$^3$ is —NR$^{29}$C(O)— or —O—C(O)— (wherein R$^{29}$ represents hydrogen, C$_{1-3}$alkyl or C$_{1-3}$alkoxyC$_{2-3}$alkyl) and R$^{28}$ is C$_{1-7}$alkyl, C$_{3-7}$cycloalkyl or a group R$^{30}$ wherein R$^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, C$_{1-4}$alkyl, C$_{1-4}$haloalkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, cyano, —CONR$^{31}$R$^{32}$ and —NR$^{31}$COR$^{32}$ (wherein R$^{31}$, R$^{32}$, R$^{33}$ and R$^{34}$, which may be the same or different, each represents hydrogen, C$_{1-3}$alkyl or C$_{1-3}$alkoxyC$_{2-3}$alkyl))).

Preferably R$^4$ is hydrogen, hydroxy, halogeno, cyano, amino or C$_{1-7}$alkanoyl.
More preferably R$^4$ is hydrogen.

Conveniently R$^5$ and R$^6$ are each independently selected from:
hydrogen, —OPO$_3$H$_2$, phosphonate, cyano, halogeno, nitro, amino, carboxy, carbamoyl, hydroxy, C$_{1-7}$alkoxy, C$_{1-7}$alkanoyl, C$_{1-7}$thioalkoxy, C$_{1-7}$alkyl,
(which alkyl group may bear one or more substituents selected from: halogeno, amino, C$_{1-4}$alkylamino, di(C$_{1-4}$alkyl)amino, hydroxy, C$_{1-4}$alkoxy, C$_{1-4}$alkylsulphanyl, C$_{1-4}$alkylsulphonyl, C$_{1-4}$alkoxycarbonylamino, C$_{1-4}$alkanoyl, carboxy, phenyl, sulphate, phosphate and a group —Y$^3$R$^{28}$ (wherein Y$^3$ is —NR$^{29}$C(O)— or —O—C(O)— (wherein R$^{29}$ represents hydrogen, C$_{1-3}$alkyl or C$_{1-3}$alkoxyC$_{2-3}$alkyl) and R$^{28}$ is C$_{1-7}$alkyl, C$_{3-7}$cycloalkyl or a group R$^{30}$ wherein R$^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, C$_{1-4}$alkyl, C$_{1-4}$haloalkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, cyano, —CONR$^{31}$R$^{32}$ and —NR$^{31}$COR$^{32}$ (wherein R$^{31}$, R$^{32}$, R$^{33}$ and R$^{34}$, which may be the same or different, each represents hydrogen, C$_{1-3}$alkyl or C$_{1-3}$alkoxyC$_{2-3}$alkyl))); and
a group —Y$^4$R$^{35}$
(wherein Y$^4$ is —C(O)—, —OC(O)—, —O—, —SO—, —SO$_2$—, —OSO$_2$—, —NR$^{36}$—, —C$_{1-4}$alkylNR$^{36}$—, —C$_{1-4}$alkylC(O)—, —NR$^{37}$C(O)—, —OC(O)O—, —C(O)NR$^{38}$— or —NR$^{39}$C(O)O— (wherein R$^{36}$, R$^{37}$, R$^{38}$ and R$^{39}$, which may be the same or different, each represents hydrogen, C$_{1-3}$alkyl or C$_{1-3}$alkoxyC$_{2-3}$alkyl) and
R$^{35}$ is a sugar moiety, a mono-peptide, a di-peptide, a tri-peptide, a tetra-peptide, sulphate, hydroxy, amino, C$_{1-7}$alkyl, C$_{1-7}$alkoxy, C$_{1-7}$alkanoyl, C$_{1-7}$alkylamino, di(C$_{1-7}$alkyl)amino, aminoC$_{1-7}$alkylamino, C$_{1-7}$alkylaminoC$_{1-7}$alkylamino, C$_{1-7}$alkanoylaminoC$_{1-7}$alkyl, di(C$_{1-7}$alkyl)aminoC$_{1-7}$alkylamino, C$_{1-7}$alkylphosphate, C$_{1-7}$alkylphosphonate, C$_{1-7}$alkylcarbamoylC$_{1-7}$alkyl,
(which alkyl, alkoxy, alkanoyl, alkylamino, dialkylamino, aminoalkylamino, alkylaminoalkylamino, alkanoylaminoalkyl, dialkylaminoalkylamino, alkylphosphate, alkylphosphonate or alkylcarbamoylalkyl, may bear one or more substituents selected from:
halogeno, amino, C$_{1-4}$alkylamino, di(C$_{1-4}$alkyl)amino, hydroxy, C$_{1-4}$hydroxyalkyl, C$_{1-4}$alkoxy, C$_{1-4}$alkylsulphanyl, C$_{1-4}$alkylsulphonyl, C$_{1-4}$alkoxycarbonylamino, C$_{1-4}$alkanoyl, carboxy, phenyl, nitro, sulphate, phosphate and a group —Y$^5$R$^{40}$ (wherein Y$^5$ is —NR$^{41}$C(O)—, —C(O)NR$^{42}$—, —C(O)—O— or —O—C(O)— (wherein R$^{41}$ and R$^{42}$ which may be the same or different each represents hydrogen, C$_{1-3}$alkyl or C$_{1-3}$alkoxyC$_{2-3}$alkyl) and R$^{40}$ is C$_{1-7}$alkyl, C$_{3-7}$cycloalkyl, carboxyC$_{1-7}$alkyl or a group R$^{43}$ wherein R$^{43}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —CONR$^{44}$R$^{45}$ and —NR$^{46}$COR$^{47}$ (wherein R$^{44}$, R$^{45}$, R$^{46}$ and R$^{47}$, which may be the same or different, each represents hydrogen, $C_{1-3}$alkyl or $C_{1-3}$alkoxyC$_{2-3}$alkyl))), R$^{48}$ (wherein R$^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, di($C_{1-4}$alkyl)amino, di($C_{1-4}$alkyl)aminoC$_{1-4}$alkyl, di($C_{1-4}$hydroxyalkyl)aminoC$_{1-4}$alkyl, di($C_{1-4}$aminoalkyl)aminoC$_{1-4}$alkyl, $C_{1-4}$hydroxyalkoxy, carboxy, $C_{1-4}$carboxyalkyl, phenyl, cyano, —CONR$^{49}$R$^{50}$, —NR$^{51}$COR$^{52}$ (wherein R$^{49}$, R$^{50}$, R$^{51}$ and R$^{52}$, which may be the same or different, each represents hydrogen, $C_{1-3}$alkyl or $C_{1-3}$alkoxyC$_{2-3}$alkyl) and $C_{1-4}$alkylR$^{53}$ (wherein R$^{53}$ is as defined hereinafter), $C_{1-7}$alkylR$^{48}$ (wherein R$^{48}$ is as defined hereinbefore), R$^{53}$ (wherein R$^{53}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$carboxyalkyl, $C_{1-4}$aminoalkyl, di($C_{1-4}$alkyl)aminoC$_{1-4}$alkyl, $C_{1-4}$alkoxyC$_{1-4}$alkyl, $C_{1-4}$alkylsulphonylC$_{1-4}$alkyl and R$^{54}$ (wherein R$^{54}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxyC$_{1-4}$alkyl and $C_{1-4}$alkylsulphonylC$_{1-4}$alkyl)), or (CH$_2$)$_a$Y$^6$(CH$_2$)$_b$R$^{53}$ (wherein R$^{53}$ is as defined hereinbefore, a is 0, or an integer 1–4, b is 0 or an integer 1–4 and Y$^6$ represents a direct bond, —O—, —C(O)—, —NR$^{55}$—, —NR$^{56}$C(O)— or —C(O)NR$^{57}$— (wherein R$^{55}$, R$^{56}$, and R$^{57}$, which may be the same or different, each represents hydrogen, $C_{1-3}$alkyl or $C_{1-3}$alkoxyC$_{2-3}$alkyl), and wherein one or more of the (CH$_2$)$_a$ or (CH$_2$)$_b$ groups may bear one or more substituents selected from hydroxy, amino and halogeno));

with the proviso that R$^5$ is not hydroxy, alkoxy, substituted alkoxy (wherein R$^5$ is Y$^4$R$^{35}$ and Y$^4$ is —O— and R$^{35}$ is $C_{1-7}$alkyl bearing one or more substituents selected from the list given hereinbefore), —OPO$_3$H$_2$, —O—C$_{1-7}$alkanoyl or benzyloxy.

In another embodiment of the present invention conveniently R$^5$ and R$^6$ are each independently selected from:

hydrogen, —OPO$_3$H$_2$, cyano, halogeno, nitro, amino, carboxy, hydroxy, $C_{1-7}$alkoxy, $C_{1-7}$alkanoyl, $C_{1-7}$thioalkoxy, $C_{1-7}$alkyl, (which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, sulphate, phosphate and a group —Y$^3$R$^{28}$ (wherein Y$^3$ is —NR$^{29}$C(O)— or —O—C(O)— (wherein R$^{29}$ represents hydrogen, $C_{1-3}$alkyl or $C_{1-3}$alkoxyC$_{2-3}$alkyl) and R$^{28}$ is $C_{1-7}$alkyl, $C_{3-7}$cycloalkyl or a group R$^{30}$ wherein R$^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —CONR$^{31}$R$^{32}$ and —NR$^{31}$COR$^{32}$ (wherein R$^{31}$, R$^{32}$, R$^{33}$ and R$^{34}$, which may be the same or different, each represents hydrogen, $C_{1-3}$alkyl or $C_{1-3}$alkoxyC$_{2-3}$alkyl))), and a group —Y$^4$R$^{35}$ (wherein Y$^4$ is —C(O)—, —OC(O)—, —O—, —SO—, —SO$_2$—, —OSO$_2$—, —NR$^{36}$—, —NR$^{37}$C(O)—, —OC(O)O—, —C(O)NR$^{38}$— or —NR$^{39}$C(O)O— (wherein R$^{36}$, R$^{37}$, R$^{38}$ and R$^{39}$, which may be the same or different, each represents hydrogen, $C_{1-3}$alkyl or $C_{1-3}$alkoxyC$_{2-3}$alkyl) and R$^{35}$ is a sugar moiety, a mono-peptide, a di-peptide, a tri-peptide, a tetra-peptide, sulphate, $C_{1-7}$alkyl, $C_{1-7}$alkoxy, $C_{1-7}$alkanoyl, aminoC$_{1-7}$alkylamino, $C_{1-7}$alkylaminoC$_{1-7}$alkylamino, di($C_{1-7}$alkyl)aminoC$_{1-7}$alkylamino, $C_{1-7}$alkylphosphate (which alkyl, alkoxy, alkanoyl, aminoalkylamino, alkylaminoalkylamino, dialkylaminoalkylamino, or alkylphosphate may bear one or more substituents selected from:

halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —Y$^5$R$^{40}$ (wherein Y$^5$ is —NR$^{41}$C(O)—, —C(O)NR$^{42}$—, —C(O)—O— or —O—C(O)— (wherein R$^{41}$ and R$^{42}$ which may be the same or different each represents hydrogen, $C_{1-3}$alkyl or $C_{1-3}$alkoxyC$_{2-3}$alkyl) and R$^{40}$ is $C_{1-7}$alkyl, $C_{3-7}$cycloalkyl, carboxyC$_{1-7}$alkyl or a group R$^{43}$ wherein R$^{43}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —CONR$^{44}$R$^{45}$ and —NR$^{46}$COR$^{47}$ (wherein R$^{44}$, R$^{45}$, R$^{46}$ and R$^{47}$, which may be the same or different, each represents hydrogen, $C_{1-3}$alkyl or $C_{1-3}$alkoxyC$_{2-3}$alkyl))), R$^{48}$ (wherein R$^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, phenyl, cyano, —CONR$^{49}$R$^{50}$ and —NR$^{51}$COR$^{52}$ (wherein R$^{49}$, R$^{50}$, R$^{51}$ and R$^{52}$, which may be the same or different, each represents hydrogen, $C_{1-3}$alkyl or $C_{1-3}$alkoxyC$_{2-3}$alkyl)), or R$^{53}$ (wherein R$^{53}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, C$_{1-4}$alkyl, C$_{1-4}$hydroxyalkyl, C$_{1-4}$alkoxy, C$_{1-4}$alkoxyC$_{1-4}$alkyl, C$_{1-4}$alkylsulphonylC$_{1-4}$alkyl and R$^{54}$ (wherein R$^{54}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, C$_{1-4}$alkyl, C$_{1-4}$hydroxyalkyl, C$_{1-4}$alkoxy, C$_{1-4}$alkoxyC$_{1-4}$alkyl and C$_{1-4}$alkylsulphonylC$_{1-4}$alkyl)));

with the proviso that R$^5$ is not hydroxy, alkoxy, substituted alkoxy, —OPO$_3$H$_2$, —O—C$_{1-7}$alkanoyl or benzyloxy.

Preferably R$^6$ is hydrogen, halogeno, amino, carboxy, hydroxy, C$_{1-7}$alkoxy or a group Y$^4$R$^{35}$ (wherein Y$^4$ is —C(O)—, —O— or —OSO$_2$— and R$^{35}$ is C$_{1-7}$alkyl, C$_{1-7}$alkoxy (which alkyl or alkoxy may bear one or more substituents selected from halogeno), R$^{48}$ (wherein R$^{48}$ is a benzyl group) or R$^{53}$ (wherein R$^{53}$ is a 5–6-membered saturated heterocyclic group (linked via carbon or nitrogen) with 1–2 heteroatoms selected independently from O, S and N)).

Particularly R$^6$ is hydrogen, C(O)OCH$_3$ or methoxy, especially C(O)OCH$_3$ or methoxy.

More preferably R$^6$ is hydrogen.

Preferably R$^5$ is hydrogen, halogeno, amino, carboxy, carbamoyl, C$_{1-7}$alkanoyl, C$_{1-7}$thioalkoxy, or a group —Y$^4$R$^{35}$ (wherein Y$^4$ is —C(O)—, —OC(O)—, —O—, —SO—, —OSO$_2$—, —NR$^{36}$—, —NR$^{37}$C(O)— or —C(O)NR$^{38}$— (wherein R$^{36}$, R$^{37}$ and R$^{38}$, which may be the same or different, each represents hydrogen, C$_{1-3}$alkyl or C$_{1-3}$alkoxyC$_{2-3}$alkyl) and R$^{35}$ is a sugar moiety, a mono-peptide, a di-peptide, a tri-peptide, a tetra-peptide, C$_{1-7}$alkyl, C$_{1-7}$alkoxy, C$_{1-7}$alkanoyl, C$_{1-7}$alkanoylaminoC$_{1-7}$alkyl, (which alkyl, alkoxy, alkanoyl, alkanoylaminoalkyl may bear one or more substituents selected from: halogeno, amino, hydroxy, carboxy, and a group —Y$^5$R$^{40}$ (wherein Y$^5$ is —C(O)—O— or —O—C(O)— and R$^{40}$ is C$_{1-7}$alkyl or a group R$^{43}$ wherein R$^{43}$ is a benzyl group), R$^{48}$ (wherein R$^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, fluoro, amino, C$_{1-4}$alkoxy, C$_{1-4}$hydroxyalkyl, C$_{1-4}$aminoalkyl, C$_{1-4}$alkylamino, di(C$_{1-4}$alkyl)amino, di(C$_{1-4}$alkyl)aminoC$_{1-4}$alkyl, di(C$_{1-4}$hydroxyalkyl)aminoC$_{1-4}$alkyl, di(C$_{1-4}$aminoalkyl)aminoC$_{1-4}$alkyl, C$_{1-4}$hydroxyalkoxy, carboxy, C$_{1-4}$carboxyalkyl, cyano, —CONR$^{49}$R$^{50}$, —NR$^{51}$COR$^{52}$ (wherein R$^{49}$, R$^{50}$, R$^{51}$ and R$^{52}$, which may be the same or different, each represents hydrogen, C$_{1-3}$alkyl or C$_{1-3}$alkoxyC$_{2-3}$alkyl) and C$_{1-4}$alkylR$^{53}$ (wherein R$^{53}$ is as defined hereinafter), C$_{1-7}$alkylR$^{48}$ (wherein R$^{48}$ is as defined hereinbefore), R$^{53}$ (wherein R$^{53}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, fluoro, chloro, C$_{1-4}$alkyl, C$_{1-4}$hydroxyalkyl, C$_{1-4}$alkoxy, C$_{1-4}$carboxyalkyl, C$_{1-4}$aminoalkyl, di(C$_{1-4}$alkyl)aminoC$_{1-4}$alkyl, C$_{1-4}$alkoxyC$_{1-4}$alkyl, C$_{1-4}$alkylsulphonylC$_{1-4}$alkyl and R$^{54}$ (wherein R$^{54}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, C$_{1-4}$alkyl, C$_{1-4}$hydroxyalkyl, C$_{1-4}$alkoxy, C$_{1-4}$alkoxyC$_{1-4}$alkyl and C$_{1-4}$alkylsulphonylC$_{1-4}$alkyl)), or (CH$_2$)$_a$Y$^6$(CH$_2$)$_b$R$^{53}$ (wherein R$^{53}$ is as defined hereinbefore, a is 0, or an integer 1–4, b is 0 or an integer 1–4 and Y$^6$ represents a direct bond, —O—, —C(O)—, —NR$^{55}$—, —NR$^{56}$C(O)— or —C(O)NR$^{57}$— (wherein R$^{55}$, R$^{56}$, and R$^{57}$, which may be the same or different, each represents hydrogen, C$_{1-3}$alkyl or C$_{1-3}$alkoxyC$_{2-3}$alkyl), and wherein one or more of the (CH$_2$)$_a$ or (CH$_2$)$_b$ groups may bear one or more substituents selected from hydroxy, amino and halogeno));

with the proviso that R$^5$ is not alkoxy, substituted alkoxy (wherein R$^5$ is Y$^4$R$^{35}$ and Y$^4$ is —O— and R$^{35}$ is C$_{1-7}$alkyl bearing one or more substituents selected from the list given hereinbefore), —O—C$_{1-7}$alkanoyl or benzyloxy.

Preferably R$^{53}$ is a group selected from morpholino, piperidinyl and piperazinyl which group may be substituted as hereinbefore defined.

Advantageous values for R$^5$ include:

3-{[(2R)-2,6-diaminohexanoyl]amino}propanoyloxy (such as in Example 4),

3-[(2-aminoacetyl)amino]propanoyloxy (such as in Example 5), 2-morpholinoacetylaminomethoxy (such as in Example 38), 2-carboxy-3,4,5-trihydroxytetrahydro-2H-pyran-6-yloxy (such as in Example 44), 4-(4-methylpiperazin-1-ylmethyl)phenylcarbonyloxy (such as in Example 16), 4-(morpholinomethyl)phenylcarbonyloxy (such as in Example 17), 3-(4-methylpiperazin-1-ylcarbonyl)propanoyloxy (such as in Example 40), 5-carboxypentanoyloxy (such as in Example 41), 3-(4-carboxyphenyl)propanoyloxy (such as in Example 18) and (3R)-2-amino-3-hydroxypropanoylamino (such as in Example 28).

Another advantageous value for R$^5$ is (2S)-2-amino-5-[(2-nitroethanimidoyl)amino]pentanoylamino (such as in Example 52).

Preferred values for R$^5$ include

3-{[(2R)-2,6-diaminohexanoyl]amino}propanoyloxy (such as in Example 4),

3-[(2-aminoacetyl)amino]propanoyloxy (such as in Example 5), 4-(4-methylpiperazin-1-ylmethyl)phenylcarbonyloxy (such as in Example 16), 4-(morpholinomethyl)phenylcarbonyloxy (such as in Example 17), 3-(4-methylpiperazin-1-ylcarbonyl)propanoyloxy (such as in Example 40), 5-carboxypentanoyloxy (such as in Example 41), 3-(4-carboxyphenyl)propanoyloxy (such as in Example 18) and (3R)-2-amino-3-hydroxypropanoylamino (such as in Example 28).

More preferred values for R$^5$ include 4-(4-methylpiperazin-1-ylmethyl)phenylcarbonyloxy (such as in Example 16) and
(3R)-2-amino-3-hydroxypropanoylamino (such as in Example 28).

In another embodiment of the present invention preferred values for $R^5$ include alanylamino, N-(benzyloxycarbonylalanyl)amino, and 4-(piperidino)piperidin-1-ylcarbonyloxy.

A more preferred value for $R^5$ is alanylamino.

In another embodiment of the present invention particular values of $R^5$ include amino, $C_{1-7}$alkylamino and di$C_{1-7}$alkylamino, especially amino.

When $R^{35}$ is a sugar moiety it can be, for example a monosaccharide such as a glucuronyl, glucosyl or galactosyl group or a di- or trisaccharide.

When $R^{35}$ is a sugar moiety glucuronyl or a derivative thereof is preferred.

When $R^{35}$ is a mono-, di-, tri- or tetra-peptide it is preferably derived from a natural alpha amino acid for example such as glycine, valine, lysine, alanine or serine.

In another embodiment of the present invention $R^{35}$ is an amino acid group derived from serine, threonine, arginine, glycine, alanine, β-alanine or lysine.

According to another aspect of the present invention there is provided the use of a compound of the formula I:

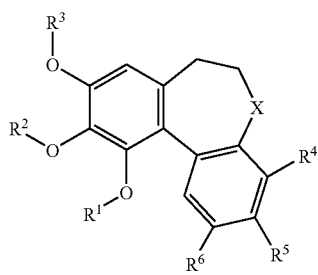

(I)

wherein

X is —C(O)—, —C(S)—, —C=NOH, or —CH($R^7$)— wherein $R^7$ is hydrogen, hydroxy, $C_{1-7}$alkoxy, —$NR^8R^9$ (wherein $R^8$ is a group —$Y^1R^{10}$ (wherein $Y^1$ is a direct bond, —C(O)—, —C(S)—, —S—, —C(O)O—, —C(O)$NR^{11}$—, —$SO_2$— or —$SO_2NR^{12}$— (wherein $R^{11}$ and $R^{12}$, which may be the same or different, each independently represents hydrogen, $C_{1-3}$alkyl or $C_{1-3}$alkoxy$C_{2-3}$alkyl) and $R^{10}$ is selected from one of the following four groups:

1) hydrogen, $C_{1-7}$alkyl or $C_{3-7}$cycloalkyl
(which alkyl or cycloalkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, phenyl, nitro, sulphate, phosphate and a group —$Y^2R^{13}$ (wherein $Y^2$ is —$NR^{14}$C(O)— or —O—C(O)— (wherein $R^{14}$ represents hydrogen, $C_{1-3}$alkyl or $C_{1-3}$alkoxy$C_{2-3}$alkyl) and $R^{13}$ is $C_{1-7}$alkyl, $C_{3-7}$cycloalkyl or a group $R^{15}$ wherein $R^{15}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{16}R^{17}$ and —$NR^{18}COR^{19}$ (wherein $R^{16}$, $R^{17}$, $R^{18}$ and $R^{19}$, which may be the same or different, each represents hydrogen, $C_{1-3}$alkyl or $C_{1-3}$alkoxy$C_{2-3}$alkyl)));

2) $R^{15}$ wherein $R^{15}$ is as defined hereinbefore;
3) $C_{2-7}$alkenyl$R^{15}$ (wherein $R^{15}$ is as defined hereinbefore); and
4) $C_{3-7}$alkynyl$R^{15}$ (wherein $R^{15}$ is as defined hereinbefore));

and $R^9$ is hydrogen, $C_{1-7}$alkyl or $C_{3-7}$cycloalkyl, which alkyl or cycloalkyl group may bear one or more substituents selected from $C_{1-4}$alkoxy and phenyl);

$R^1$, $R^2$ and $R^3$ are each independently
hydrogen, $PO_3H_2$, sulphate, $C_{3-7}$cycloalkyl, $C_{2-7}$alkenyl, $C_{2-7}$alkynyl, $C_{1-7}$alkanoyl, a group $R^{20}C_{1-7}$alkyl (wherein $R^{20}$ is phenyl which may bear one or more substituents selected from $C_{1-4}$alkyl, $C_{1-4}$alkoxy, $C_{1-4}$aminoalkyl and $C_{1-4}$hydroxyalkoxy), $C_{1-7}$alkyl or $C_{1-7}$alkylsulphonyl
(which alkyl or alkylsulphonyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^2R^{21}$ (wherein $Y^2$ is —$NR^{22}$C(O)— or —O—C(O)— (wherein $R^{22}$ represents hydrogen, $C_{1-3}$alkyl or $C_{1-3}$alkoxy$C_{2-3}$alkyl) and $R^{21}$ is $C_{1-7}$alkyl, $C_{3-7}$cycloalkyl or a group $R^{23}$ wherein $R^{23}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{24}R^{25}$ and —$NR^{26}COR^{27}$ (wherein $R^{24}$, $R^{25}$, $R^{26}$ and $R^{27}$, which may be the same or different, each represents hydrogen, $C_{1-3}$alkyl or $C_{1-3}$alkoxy$C_{2-3}$alkyl)));

with the proviso that at least two of $R^1$, $R^2$ and $R^3$ are $C_{1-7}$alkyl;

$R^4$, $R^5$ and $R^6$ are each independently selected from:
hydrogen, —$OPO_3H_2$, cyano, halogeno, nitro, amino, carboxy, hydroxy, $C_{1-7}$alkoxy, $C_{1-7}$alkanoyl, $C_{1-7}$thioalkoxy, $C_{1-7}$alkyl,
(which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, sulphate, phosphate and a group —$Y^3R^{28}$ (wherein $Y^3$ is —$NR^{29}$C(O)— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl))), and a group —$Y^4R^{35}$ (wherein $Y^4$ is —C(O)—, —OC(O)—, —O—, —SO—, —SO$_2$—, —OSO$_2$—, —NR$^{36}$—, —NR$^{37}$C(O)—, —OC(O)O—, —C(O)NR$^{38}$— or —NR$^{39}$C(O)O— (wherein $R^{36}$, $R^{37}$, $R^{38}$ and $R^{39}$, which may be the same or different, each represents hydrogen, $C_{1-3}$alkyl or $C_{1-3}$alkoxy$C_{2-3}$alkyl) and $R^{35}$ is a sugar moiety, a mono-peptide, a di-peptide, a tri-peptide, a tetra-peptide, sulphate, $C_{1-7}$alkyl, $C_{1-7}$alkoxy, $C_{1-7}$alkanoyl, amino$C_{1-7}$alkylamino, $C_{1-7}$alkylamino$C_{1-7}$alkylamino, di($C_{1-7}$alkyl)amino$C_{1-7}$alkylamino, $C_{1-7}$alkylphosphate (which alkyl, alkoxy, alkanoyl, aminoalkylamino, alkylaminoalkylamino, dialkylaminoalkylamino, or alkylphosphate may bear one or more substituents selected from:

halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —Y$^5$R$^{40}$ (wherein $Y^5$ is —NR$^{41}$C(O)—, —C(O)NR$^{42}$—, —C(O)—O— or —O—C(O)— (wherein $R^{41}$ and $R^{42}$ which may be the same or different each represents hydrogen, $C_{1-3}$alkyl or $C_{1-3}$alkoxy$C_{2-3}$alkyl) and $R^{40}$ is $C_{1-7}$alkyl, $C_{3-7}$cycloalkyl, carboxy$C_{1-7}$alkyl or a group $R^{43}$ wherein $R^{43}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —CONR$^{44}$R$^{45}$ and —NR$^{46}$COR$^{47}$ (wherein $R^{44}$, $R^{45}$, $R^{46}$ and $R^{47}$, which may be the same or different, each represents hydrogen, $C_{1-3}$alkyl or $C_{1-3}$alkoxy$C_{2-3}$alkyl))), $R^{48}$ (wherein $R^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, phenyl, cyano, —CONR$^{49}$R$^{50}$ and —NR$^{51}$COR$^{52}$ (wherein $R^{49}$, $R^{50}$, $R^{51}$ and $R^{52}$, which may be the same or different, each represents hydrogen, $C_{1-3}$alkyl or $C_{1-3}$alkoxy$C_{2-3}$alkyl)), or $R^{53}$ (wherein $R^{53}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl and $R^{54}$ (wherein $R^{54}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl)));

with the proviso that $R^5$ is not hydroxy, alkoxy, substituted alkoxy, —OPO$_3$H$_2$, —O—$C_{1-7}$alkanoyl or benzyloxy;

and salts thereof, pharmaceutically acceptable salts thereof, solvates and hydrates thereof, and prodrugs thereof for example esters, amides and sulphides, in the manufacture of a medicament for use in the production of a vascular damaging effect in warm-blooded animals such as humans.

According to another aspect of the present invention there is provided a compound of the formula IIa:

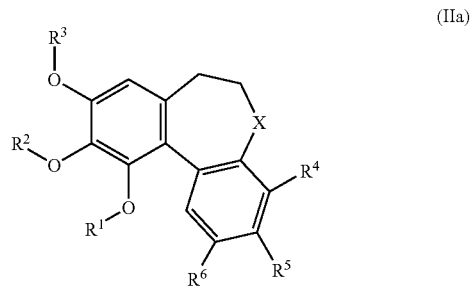

(IIa)

wherein

X is —C(O)—, —C(S)—, —C=NOH, or —CH(R$^7$)— wherein $R^7$ is hydrogen, hydroxy, $C_{1-7}$alkoxy, —OR$^8$ or —NR$^8$R$^9$ (wherein $R^8$ is a group —Y$^1$R$^{10}$ (wherein $Y^1$ is a direct bond, —C(O)—, —C(S)—, —S—, —C(O)O—, —C(O)NR$^{11}$—, —SO$_2$— or —SO$_2$NR$^{12}$— (wherein $R^{11}$ and $R^{12}$, which may be the same or different, each independently represents hydrogen, $C_{1-3}$alkyl or $C_{1-3}$alkoxy$C_{2-3}$alkyl) and $R^{10}$ is selected from one of the following nine groups:

1) hydrogen, $C_{1-7}$alkyl, $C_{3-7}$cycloalkyl, $C_{1-4}$alkylY$^8$C$_{1-4}$alkyl wherein $Y^8$ is as defined hereinafter, or phenyl, (which alkyl, cycloalkyl, alkylY$^8$alkyl or phenyl group may bear one or more substituents selected from:

halogeno, amino, $C_{1-4}$alkylamino, di($C_{1-4}$alkyl)amino, hydroxy, carboxy, carbamoyl, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, phenyl, nitro, sulphate, phosphate, $Z^1$ (wherein $Z^1$ represents a 5–6 membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-7}$alkanoyl, cyano$C_{1-4}$alkyl, $C_{1-4}$alkoxy$C_{1-4}$alkyl, $C_{1-4}$alkylsulphonyl$C_{1-4}$alkyl and $Z^2$ (wherein $Z^2$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-4}$alkanoyl, cyano$C_{1-4}$alkyl, $C_{1-4}$alkoxy$C_{1-4}$alkyl and $C_{1-4}$alkylsulphonyl$C_{1-4}$alkyl)), $C_{1-4}$alkylZ$^1$ (wherein $Z^1$ is as defined hereinbefore), and a group —Y$^2$R$^{13}$ (wherein $Y^2$ is —NR$^{14}$C(O)— or —O—C(O)— (wherein $R^{14}$ represents hydrogen, $C_{1-3}$alkyl or $C_{1-3}$alkoxy$C_{2-3}$alkyl) and $R^{13}$ is $C_{1-7}$alkyl, $C_{3-7}$cycloalkyl or a group $R^{15}$ wherein $R^{15}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{16}R^{17}$ and —$NR^{18}COR^{19}$ (wherein $R^{16}$, $R^{17}$, $R^{18}$ and $R^{19}$, which may be the same or different, each represents hydrogen, $C_{1-3}$alkyl or $C_{1-3}$alkoxy$C_{2-3}$alkyl)));

2) $R^{15}$ wherein $R^{15}$ is as defined hereinbefore;
3) $C_{2-7}$alkenyl$R^{15}$ (wherein $R^{15}$ is as defined hereinbefore);
4) $C_{3-7}$alkynyl$R^{15}$ (wherein $R^{15}$ is as defined hereinbefore));
5) $Z^1$ (wherein $Z^1$ is as defined hereinbefore);
6) $C_{1-7}$alkyl$Z^1$ (wherein $Z^1$ is as defined hereinbefore);
7) $C_{1-7}$alkyl$Y^8Z^1$ (wherein $Z^1$ is as defined hereinbefore and $Y^8$ is —C(O)—, —$NR^{59}$C(O)—, —$NR^{59}$C(O)$C_{1-4}$alkyl-, —C(O)$NR^{60}$— or —C(O)$NR^{60}C_{1-4}$alkyl-, (wherein $R^{59}$ and $R^{60}$, which may be the same or different, each represents hydrogen, $C_{1-3}$alkyl, $C_{1-3}$hydroxyalkyl or $C_{1-3}$alkoxy$C_{2-3}$alkyl));
8) $(C_{1-7}$alkyl$)_cY^9Z^3$ (wherein c is 0 or 1, $Z^3$ is an amino acid group and $Y^9$ is a direct bond, —C(O)— or —$NR^{61}$— (wherein $R^{61}$ is hydrogen, $C_{1-3}$alkyl or $C_{1-3}$alkoxy$C_{2-3}$alkyl)); and
9) $C_{1-7}$alkyl$R^{15}$ (wherein $R^{15}$ is as defined hereinbefore);

and $R^9$ is hydrogen, $C_{1-7}$alkyl or $C_{3-7}$cycloalkyl, which alkyl or cycloalkyl group may bear one or more substituents selected from $C_{1-4}$alkoxy and phenyl);

$R^1$, $R^2$ and $R^3$ are each independently
hydrogen, $PO_3H_2$, sulphate, $C_{3-7}$cycloalkyl, $C_{2-7}$alkenyl, $C_{2-7}$alkynyl, $C_{1-7}$alkanoyl, a group $R^{20}C_{1-7}$alkyl (wherein $R^{20}$ is phenyl which may bear one or more substituents selected from $C_{1-4}$alkyl, $C_{1-4}$alkoxy, $C_{1-4}$aminoalkyl and $C_{1-4}$hydroxyalkoxy), $C_{1-7}$alkyl or $C_{1-7}$alkylsulphonyl
(which alkyl or alkylsulphonyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^2R^{21}$ (wherein $Y^2$ is —$NR^{22}$C(O)— or —O—C(O)— (wherein $R^{22}$ represents hydrogen, $C_{1-3}$alkyl or $C_{1-3}$alkoxy$C_{2-3}$alkyl) and $R^{21}$ is $C_{1-7}$alkyl, $C_{3-7}$cycloalkyl or a group $R^{23}$ wherein $R^{23}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{24}R^{25}$ and —$NR^{26}COR^{27}$ (wherein $R^{24}$, $R^{25}$, $R^{26}$ and $R^{27}$, which may be the same or different, each represents hydrogen, $C_{1-3}$alkyl or $C_{1-3}$alkoxy$C_{2-3}$alkyl)));

with the proviso that at least two of $R^1$, $R^2$ and $R^3$ are $C_{1-7}$alkyl;

$R^4$ is hydrogen, cyano, halogeno, nitro, amino, hydroxy, $C_{1-7}$alkoxy, $C_{1-7}$thioalkoxy, $C_{1-7}$alkanoyl or $C_{1-7}$alkyl,
(which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^3R^{28}$ (wherein $Y^3$ is —$NR^{29}$C(O)— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl)));

$R^5$ and $R^6$ are each independently selected from
hydrogen, —$OPO_3H_2$, phosphonate, cyano; halogeno, nitro, amino, carboxy, carbamoyl, hydroxy, $C_{1-7}$alkoxy, $C_{1-7}$alkanoyl, $C_{1-7}$thioalkoxy, $C_{1-7}$alkyl,
(which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, sulphate, phosphate and a group —$Y^3R^{28}$ (wherein $Y^3$ is —$NR^{29}$C(O)— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl))), and a group —$Y^4R^{35}$
(wherein $Y^4$ is —C(O)—, —OC(O)—, —O—, —SO—, —$SO_2$—, —$OSO_2$—, —$NR^{36}$—, —$C_{1-4}$alkyl$NR^{36}$—, —$C_{1-4}$alkylC(O)—, —$NR^{37}$C(O)—, —OC(O)O—, —C(O)$NR^{38}$— or —$NR^{39}$C(O)O— (wherein $R^{36}$, $R^{37}$, $R^{38}$ and $R^{39}$, which may be the same or different, each represents hydrogen, $C_{1-3}$alkyl or $C_{1-3}$alkoxy$C_{2-3}$alkyl) and $R^{35}$ is a sugar moiety, a mono-peptide, a di-peptide, a tri-peptide, a tetra-peptide, sulphate, hydroxy, amino, $C_{1-7}$alkyl, $C_{1-7}$alkoxy, $C_{1-7}$alkanoyl, $C_{1-7}$alkylamino, di($C_{1-7}$alkyl)amino, amino$C_{1-7}$alkylamino, $C_{1-7}$alkylamino$C_{1-7}$alkylamino, $C_{1-7}$alkanoylamino$C_{1-7}$alkyl, di($C_{1-7}$alkyl)amino$C_{1-7}$alkylamino, $C_{1-7}$alkylphosphate, $C_{1-7}$alkylphosphonate, $C_{1-7}$alkylcarbamoyl$C_{1-7}$alkyl,
(which alkyl, alkoxy, alkanoyl, alkylamino, dialkylamino, aminoalkylamino, alkylaminoalkylamino, alkanoylaminoalkyl, dialkylaminoalkylamino, alkylphosphate, alkylphosphonate or alkylcarbamoylalkyl, may bear one or more substituents selected from:
halogeno, amino, $C_{1-4}$alkylamino, di($C_{1-4}$alkyl)amino, hydroxy, $C_{1-4}$hydroxyalkyl, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^5R^{40}$ (wherein $Y^5$ is —NR$^{41}$C(O)—, —C(O)NR$^{42}$—, —C(O)—O— or —O—C(O)— (wherein R$^{41}$ and R$^{42}$ which may be the same or different each represents hydrogen, C$_{1-3}$alkyl or C$_{1-3}$alkoxyC$_{2-3}$alkyl) and R$^{40}$ is C$_{1-7}$alkyl, C$_{3-7}$cycloalkyl, carboxyC$_{1-7}$alkyl or a group R$^{43}$ wherein R$^{43}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, C$_{1-4}$alkyl, C$_{1-4}$haloalkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, cyano, —CONR$^{44}$R$^{45}$ and —NR$^{46}$COR$^{47}$ (wherein R$^{44}$, R$^{45}$, R$^{46}$ and R$^{47}$, which may be the same or different, each represents hydrogen, C$_{1-3}$alkyl or C$_{1-3}$alkoxyC$_{2-3}$alkyl))), R$^{48}$ (wherein R$^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, C$_{1-4}$alkyl, C$_{1-4}$haloalkyl, C$_{1-4}$alkoxy, C$_{1-4}$hydroxyalkyl, C$_{1-4}$aminoalkyl, C$_{1-4}$alkylamino, di(C$_{1-4}$alkyl)amino, di(C$_{1-4}$ alkyl)aminoC$_{1-4}$alkyl, di(C$_{1-4}$hydroxyalkyl) aminoC$_{1-4}$alkyl, di(C$_{1-4}$aminoalkyl)aminoC$_{1-4}$alkyl, C$_{1-4}$hydroxyalkoxy, carboxy, C$_{1-4}$carboxyalkyl, phenyl, cyano, —CONR$^{49}$R$^{50}$, —NR$^{51}$COR$^{52}$ (wherein R$^{49}$, R$^{50}$, R$^{51}$ and R$^{52}$, which may be the same or different, each represents hydrogen, C$_{1-3}$alkyl or C$_{1-3}$alkoxyC$_{2-3}$alkyl) and C$_{1-4}$alkylR$^{53}$ (wherein R$^{53}$ is as defined hereinafter), C$_{1-7}$alkylR$^{48}$ (wherein R$^{48}$ is as defined hereinbefore), R$^{53}$ (wherein R$^{53}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, C$_{1-4}$alkyl, C$_{1-4}$hydroxyalkyl, C$_{1-4}$alkoxy, C$_{1-4}$carboxyalkyl, C$_{1-4}$aminoalkyl, di(C$_{1-4}$alkyl)aminoC$_{1-4}$alkyl, C$_{1-4}$alkoxyC$_{1-4}$alkyl, C$_{1-4}$alkylsulphonylC$_{1-4}$alkyl and R$^{54}$ (wherein R$^{54}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, C$_{1-4}$alkyl, C$_{1-4}$hydroxyalkyl, C$_{1-4}$alkoxy, C$_{1-4}$alkoxyC$_{1-4}$alkyl and C$_{1-4}$alkylsulphonylC$_{1-4}$alkyl)), or (CH$_2$)$_a$Y$^6$(CH$_2$)$_b$R$^{53}$ (wherein R$^{53}$ is as defined hereinbefore, a is 0, or an integer 1–4, b is 0 or an integer 1–4 and Y$^6$ represents a direct bond, —O—, —C(O)—, —NR$^{55}$—, —NR$^{56}$C(O)— or —C(O)NR$^{57}$— (wherein R$^{55}$, R$^{56}$, and R$^{57}$, which may be the same or different, each represents hydrogen, C$_{1-3}$alkyl or C$_{1-3}$alkoxyC$_{2-3}$alkyl), and wherein one or more of the (CH$_2$)$_a$ or (CH$_2$)$_b$ groups may bear one or more substituents selected from hydroxy, amino and halogeno));

with the proviso that R$^5$ is not hydroxy, alkoxy, substituted alkoxy (wherein R$^5$ is Y$^4$R$^{35}$ and Y$^4$ is —O— and R$^{35}$ is C$_{1-7}$alkyl bearing one or more substituents selected from the list given hereinbefore), —OPO$_3$H$_2$, —O—C$_{1-7}$alkanoyl or benzyloxy;

with the further proviso that at least one of R$^5$ or R$^6$ is a group —Y$^4$R$^{35}$ (wherein Y$^4$ and R$^{35}$ are as defined hereinbefore) but with the further provisos that when R$^5$ is —Y$^4$R$^{35}$ and R$^6$ is hydrogen, hydroxy, methoxy or methoxycarbonyl, —Y$^4$R$^{35}$ is not selected from cases wherein:

Y$^4$ is —C(O)—, —OC(O)—, —O—, —SO—, —OSO$_2$—, —NR$^{36}$—, —NR$^{37}$C(O)— or —C(O)NR$^{38}$— (wherein R$^{36}$, R$^{37}$ and R$^{38}$, which may be the same or different, each represents hydrogen, C$_{1-3}$alkyl or C$_{1-3}$alkoxyC$_{2-3}$alkyl) and R$^{35}$ is a glycine, valine or lysine group, a dipeptide of glycine and valine groups, C$_{1-7}$alkyl, C$_{1-7}$alkoxy, C$_{1-7}$alkanoyl, (which alkyl, alkoxy or alkanoyl may bear one or more substituents selected from: halogeno, hydroxy, and a group —Y$^5$R$^{40}$ (wherein Y$^5$ is —O—C(O)— and R$^{40}$ is C$_{1-7}$alkyl)), or R$^{48}$ (wherein R$^{48}$ is a tetrazolyl group (which may or may not be substituted as hereinbefore defined), a phenyl group or a benzyl group which phenyl or benzyl group may bear one or more substituents selected from C$_{1-4}$alkyl); and that when R$^6$ is —Y$^4$R$^{35}$ and R$^5$ is hydrogen, hydroxy, methoxy or methoxycarbonyl, —Y$^4$R$^{35}$ is not selected from cases wherein:

Y$^4$ is —C(O)—, —O— or —OSO$_2$— and R$^{35}$ is C$_{1-7}$alkyl, C$_{1-7}$alkoxy (which alkyl, alkoxy or alkanoyl may bear one or more substituents selected from: halogeno), R$^{48}$ (wherein R$^{48}$ is a benzyl group which benzyl group may bear one or more substituents selected from C$_{1-4}$alkyl), or R$^{53}$ (wherein R$^{53}$ is piperidinyl);

and salts thereof, pharmaceutically acceptable salts thereof, solvates and hydrates thereof, and prodrugs thereof.

According to a further aspect of the present invention there is provided a compound of the formula IIa:

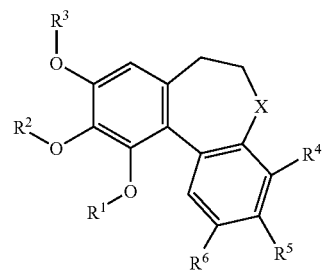

(IIa)

wherein

X is —C(O)—, —C(S)—, —C=NOH, or —CH(R$^7$)— wherein R$^7$ is hydrogen, hydroxy, C$_{1-7}$alkoxy, —OR$^8$ or —NR$^8$R$^9$ (wherein R$^8$ is a group —Y$^1$R$^{10}$ (wherein Y$^1$ is a direct bond, —C(O)—, —C(S)—, —S—, —C(O)O—, —C(O)NR$^{11}$—, —SO$_2$— or —SO$_2$NR$^{12}$— (wherein R$^{11}$ and R$^{12}$, which may be the same or different, each independently represents hydrogen, C$_{1-3}$alkyl or C$_{1-3}$alkoxyC$_{2-3}$alkyl) and R$^{10}$ is selected from one of the following nine groups:

1) hydrogen, C$_{1-7}$alkyl, C$_{3-7}$cycloalkyl, C$_{1-4}$alkylY$^8$ C$_{1-4}$alkyl wherein Y$^8$ is as defined hereinafter, or phenyl, (which alkyl, cycloalkyl, alkylY$^8$alkyl or phenyl group may bear one or more substituents selected from: halogeno, amino, C$_{1-4}$alkylamino, di(C$_{1-4}$alkyl)amino, hydroxy, carboxy, carbamoyl, C$_{1-4}$alkoxy, C$_{1-4}$alkylsulphanyl, $C_{1-4}$alkylsulphonyl, $C_{1-4}$alkoxycarbonylamino, $C_{1-4}$alkanoyl, phenyl, nitro, sulphate, phosphate, $Z^1$ (wherein $Z^1$ represents a 5–6 membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-7}$alkanoyl, cyano$C_{1-4}$alkyl, $C_{1-4}$alkoxy$C_{1-4}$alkyl, $C_{1-4}$alkylsulphonyl$C_{1-4}$alkyl and $Z^2$ (wherein $Z^2$ is a 5–6-membered saturated heterocyclic group (linked via carbon or nitrogen) with 1–2 heteroatoms, selected independently from O, S and N, which etherocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-7}$alkanoyl, cyano$C_{1-4}$alkyl, $C_{1-4}$alkoxy$C_{1-4}$alkyl and $C_{1-4}$alkylsulphonyl$C_{1-4}$alkyl)), $C_{1-4}$alkyl$Z^1$ (wherein $Z^1$ is as defined hereinbefore), and a group —$Y^2R^{13}$ (wherein $Y^2$ is —$NR^{14}C(O)$— or —O—C(O)— (wherein $R^{14}$ represents hydrogen, $C_{1-3}$alkyl or $C_{1-3}$alkoxy$C_{2-3}$alkyl) and $R^{13}$ is $C_{1-7}$alkyl, $C_{3-7}$cycloalkyl or a group $R^{15}$ wherein $R^{15}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{16}R^{17}$ and —$NR^{18}COR^{19}$ (wherein $R^{16}$, $R^{17}$, $R^{18}$ and $R^{19}$, which may be the same or different, each represents hydrogen, $C_{1-3}$alkyl or $C_{1-3}$alkoxy$C_{2-3}$alkyl)));

2) $R^{15}$ wherein $R^{15}$ is as defined hereinbefore;
3) $C_{2-7}$alkenyl$R^{15}$ (wherein $R^{15}$ is as defined hereinbefore);
4) $C_{3-7}$alkynyl$R^{15}$ (wherein $R^{15}$ is as defined hereinbefore));
5) $Z^1$ (wherein $Z^1$ is as defined hereinbefore);
6) $C_{1-7}$alkyl$Z^1$ (wherein $Z^1$ is as defined hereinbefore);
7) $C_{1-7}$alkyl$Y^8Z^1$ (wherein $Z^1$ is as defined hereinbefore and $Y^8$ is —C(O)—, —$NR^{59}C(O)$—, —$NR^{59}C(O)C_{1-4}$alkyl-, —C(O)$NR^{60}$— or —C(O)$NR^{60}C_{1-4}$alkyl-, (wherein $R^{59}$ and $R^{60}$, which may be the same or different, each represents hydrogen, $C_{1-3}$alkyl, $C_{1-3}$hydroxyalkyl or $C_{1-3}$alkoxy$C_{2-3}$alkyl));
8) $(C_{1-7}$alkyl$)_cY^9Z^3$ (wherein c is 0 or 1, $Z^3$ is an amino acid group and $Y^9$ is a direct bond, —C(O)— or —$NR^{61}$— (wherein $R^{61}$ is hydrogen, $C_{1-3}$alkyl or $C_{1-3}$alkoxy$C_{2-3}$alkyl)); and
9) $C_{1-7}$alkyl$R^{15}$ (wherein $R^{15}$ is as defined hereinbefore); and $R^9$ is hydrogen, $C_{1-7}$alkyl or $C_{3-7}$cycloalkyl, which alkyl or cycloalkyl group may bear one or more substituents selected from $C_{1-4}$alkoxy and phenyl);

$R^1$, $R^2$ and $R^3$ are each independently hydrogen, $PO_3H_2$, sulphate, $C_{3-7}$cycloalkyl, $C_{2-7}$alkenyl, $C_{2-7}$alkynyl, $C_{1-7}$alkanoyl, a group $R^{20}C_{1-7}$alkyl (wherein $R^{20}$ is phenyl which may bear one or more substituents selected from $C_{1-4}$alkyl, $C_{1-4}$alkoxy, $C_{1-4}$aminoalkyl and $C_{1-4}$hydroxyalkoxy), $C_{1-7}$alkyl or $C_{1-7}$alkylsulphonyl (which alkyl or alkylsulphonyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^2R^{21}$ (wherein $Y^2$ is —$NR^{22}C(O)$— or —O—C(O)— (wherein $R^{22}$ represents hydrogen, $C_{1-3}$alkyl or $C_{1-3}$alkoxy$C_{2-3}$alkyl) and $R^{21}$ is $C_{1-7}$alkyl, $C_{3-7}$cycloalkyl or a group $R^{23}$ wherein $R^{23}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{24}R^{25}$ and —$NR^{26}COR^{27}$ (wherein $R^{24}$, $R^{25}$, $R^{26}$ and $R^{27}$, which may be the same or different, each represents hydrogen, $C_{1-3}$alkyl or $C_{1-3}$alkoxy$C_{2-3}$alkyl)));

with the proviso that at least two of $R^1$, $R^2$ and $R^3$ are $C_{1-7}$alkyl;

$R^4$ is hydrogen, cyano, halogeno, nitro, amino, hydroxy, $C_{1-7}$alkoxy, $C_{1-7}$thioalkoxy, $C_{1-7}$alkanoyl or $C_{1-7}$alkyl,
(which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^3R^{28}$ (wherein $Y^3$ is —$NR^{29}C(O)$— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl)));

$R^5$ and $R^6$ are each independently selected from
hydrogen, —$OPO_3H_2$, phosphonate, cyano, halogeno, nitro, amino, cyano, carbamoyl, hydroxy, $C_{1-7}$alkoxy, $C_{1-7}$alkanoyl, $C_{1-7}$thioalkoxy, $C_{1-7}$alkyl,
(which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, sulphate, phosphate and a group —$Y^3R^{28}$ (wherein $Y^3$ is —$NR^{29}C(O)$— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl))), and a group —$Y^4R^{35}$ (wherein $Y^4$ is —C(O)—, —OC(O)—, —O—, —SO—, —SO$_2$—, —OSO$_2$—, —NR$^{36}$—, —C$_{1-4}$alkylNR$^{36}$—, —C$_{1-4}$alkylC(O)—, —NR$^{37}$C(O)—, —OC(O)O—, —C(O)NR$^{38}$— or —NR$^{39}$C(O)O— (wherein R$^{36}$, R$^{37}$, R$^{38}$ and R$^{39}$, which may be the same or different, each represents hydrogen, C$_{1-3}$alkyl or C$_{1-3}$alkoxyC$_{2-3}$alkyl) and R$^{35}$ is a sugar moiety, a mono-peptide, a di-peptide, a tri-peptide, a tetra-peptide, sulphate, hydroxy, amino, C$_{1-7}$alkyl, C$_{1-7}$alkoxy, C$_{1-7}$alkanoyl, C$_{1-7}$alkylamino, di(C$_{1-7}$alkyl)amino, aminoC$_{1-7}$alkylamino, C$_{1-7}$alkylaminoC$_{1-7}$alkylamino, C$_{1-7}$alkanoylaminoC$_{1-7}$alkyl, di(C$_{1-7}$alkyl)aminoC$_{1-7}$alkylamino, C$_{1-7}$alkylphosphate, C$_{1-7}$alkylphosphonate, C$_{1-7}$alkylcarbamoylC$_{1-7}$alkyl, (which alkyl, alkoxy, alkanoyl, alkylamino, dialkylamino, aminoalkylamino, alkylaminoalkylamino, alkanoylaminoalkyl, dialkylaminoalkylamino, alkylphosphate, alkylphosphonate or alkylcarbamoylalkyl, may bear one or more substituents selected from:

halogeno, amino, C$_{1-4}$alkylamino, di(C$_{1-4}$alkyl)amino, hydroxy, C$_{1-4}$hydroxyalkyl, C$_{1-4}$alkoxy, C$_{1-4}$alkylsulphanyl, C$_{1-4}$alkylsulphonyl, C$_{1-4}$alkoxycarbonylamino, C$_{1-4}$alkanoyl, carboxy, phenyl, nitro, sulphate, phosphate and a group —Y$^5$R$^{40}$ (wherein Y$^5$ is —NR$^{41}$C(O)—, —C(O)NR$^{42}$—, —C(O)—O— or —O—C(O)— (wherein R$^{41}$ and R$^{42}$ which may be the same or different each represents hydrogen, C$_{1-3}$alkyl or C$_{1-3}$alkoxyC$_{2-3}$alkyl) and R$^{40}$ is C$_{1-7}$alkyl, C$_{3-7}$cycloalkyl, carboxyC$_{1-7}$alkyl or a group R$^{43}$ wherein R$^{43}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, C$_{1-4}$alkyl, C$_{1-4}$haloalkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, cyano, —CONR$^{44}$R$^{45}$ and —NR$^{46}$COR$^{47}$ (wherein R$^{44}$, R$^{45}$, R$^{46}$ and R$^{47}$, which may be the same or different, each represents hydrogen, C$_{1-3}$alkyl or C$_{1-3}$alkoxyC$_{2-3}$alkyl))), R$^{48}$ (wherein R$^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, C$_{1-4}$alkyl, C$_{1-4}$haloalkyl, C$_{1-4}$alkoxy, C$_{1-4}$hydroxyalkyl, C$_{1-4}$aminoalkyl, C$_{1-4}$alkylamino, di(C$_{1-4}$alkyl)amino, di(C$_{1-4}$alkyl)aminoC$_{1-4}$alkyl, di(C$_{1-4}$hydroxyalkyl)aminoC$_{1-4}$alkyl, di(C$_{1-4}$aminoalkyl)aminoC$_{1-4}$alkyl, C$_{1-4}$hydroxyalkoxy, carboxy, C$_{1-4}$carboxyalkyl, phenyl, cyano, —CONR$^{49}$R$^{50}$, —NR$^{51}$COR$^{52}$ (wherein R$^{49}$, R$^{50}$, R$^{51}$ and R$^{52}$, which may be the same or different, each represents hydrogen, C$_{1-3}$alkyl or C$_{1-3}$alkoxyC$_{2-3}$alkyl) and C$_{1-4}$alkylR$^{53}$ (wherein R$^{53}$ is as defined hereinafter), C$_{1-7}$alkylR$^{48}$ (wherein R$^{48}$ is as defined hereinbefore), R$^{53}$ (wherein R$^{53}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, C$_{1-4}$alkyl, C$_{1-4}$hydroxyalkyl, C$_{1-4}$alkoxy, C$_{1-4}$carboxyalkyl, C$_{1-4}$aminoalkyl, di(C$_{1-4}$alkyl)aminoC$_{1-4}$alkyl, C$_{1-4}$alkoxyC$_{1-4}$alkyl, C$_{1-4}$alkylsulphonylC$_{1-4}$alkyl and R$^{54}$ (wherein R$^{54}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, C$_{1-4}$alkyl, C$_{1-4}$hydroxyalkyl, C$_{1-4}$alkoxy, C$_{1-4}$alkoxyC$_{1-4}$alkyl and C$_{1-4}$alkylsulphonylC$_{1-4}$alkyl)), or (CH$_2$)$_a$Y$^6$(CH$_2$)$_b$R$^{53}$ (wherein R$^{53}$ is as defined hereinbefore, a is 0, or an integer 1–4, b is 0 or an integer 1–4 and Y$^6$ represents a direct bond, —O—, —C(O)—, —NR$^{55}$—, —NR$^{56}$C(O)— or —C(O)NR$^{57}$— (wherein R$^{55}$, R$^{56}$, and R$^{57}$, which may be the same or different, each represents hydrogen, C$_{1-3}$alkyl or C$_{1-3}$alkoxyC$_{2-3}$alkyl), and wherein one or more of the (CH$_2$)$_a$ or (CH$_2$)$_b$ groups may bear one or more substituents selected from hydroxy, amino and halogeno));

with the proviso that R$^5$ is not hydroxy, alkoxy, substituted alkoxy (wherein R$^5$ is Y$^4$R$^{35}$ and Y$^4$ is —O— and R$^{35}$ is C$_{1-7}$alkyl bearing one or more substituents selected from the list given hereinbefore), —OPO$_3$H$_2$, —O—C$_{1-7}$alkanoyl or benzyloxy;

with the further proviso that at least one of R$^5$ or R$^6$ is a group —Y$^4$R$^{35}$ (wherein Y$^4$ and R$^{35}$ are as defined hereinbefore) but with the further provisos that when R$^5$ is —Y$^4$R$^{35}$ and R$^6$ is hydrogen, hydroxy, methoxy or methoxycarbonyl, —Y$^4$R$^{35}$ is not selected from cases wherein:

Y$^4$ is —C(O)—, —OC(O)—, —O—, —SO—, —OSO$_2$—, —NR$^{36}$—, —NR$^{37}$C(O)— or —C(O)NR$^{38}$— (wherein R$^{36}$, R$^{37}$ and R$^{38}$, which may be the same or different, each represents hydrogen, C$_{1-3}$alkyl or C$_{1-3}$alkoxyC$_{2-3}$alkyl) and R$^{35}$ is a mono-peptide, a di-peptide, a tri-peptide, a tetra-peptide, C$_{1-7}$alkyl, C$_{1-7}$alkoxy, C$_{1-7}$alkanoyl, (which alkyl, alkoxy or alkanoyl may bear one or more substituents selected from: halogeno, hydroxy, and a group —Y$^5$R$^{40}$ (wherein Y$^5$ is —O—C(O)— and R$^{40}$ is C$_{1-7}$alkyl)), or R$^{48}$ (wherein R$^{48}$ is a tetrazolyl group (which may or may not be substituted as hereinbefore defined), a phenyl group or a benzyl group which phenyl or benzyl group may bear one or more substituents selected from C$_{1-4}$alkyl); and that when R$^6$ is —Y$^4$R$^{35}$ and R$^5$ is hydrogen, hydroxy, methoxy or methoxycarbonyl, —Y$^4$R$^{35}$ is not selected from cases wherein:

Y$^4$ is —C(O)—, —O— or —OSO$_2$— and R$^{35}$ is C$_{1-7}$alkyl, C$_{1-7}$alkoxy (which alkyl, alkoxy or alkanoyl may bear one or more substituents selected from: halogeno), R$^{48}$ (wherein R$^{48}$ is a benzyl group which benzyl group may bear one or more substituents selected from C$_{1-4}$alkyl), or R$^{53}$ (wherein R$^{53}$ is piperidinyl);

and salts thereof, pharmaceutically acceptable salts thereof, solvates and hydrates thereof, and prodrugs thereof.

According to a further aspect of the present invention there is provided the use of a compound of the formula IIa as defined hereinbefore, and salts thereof, pharmaceutically acceptable salts thereof, solvates and hydrates thereof, and prodrugs thereof, in the manufacture of a medicament for use in the production of a vascular damaging effect in warm-blooded animals such as humans.

According to another aspect of the present invention there is provided the use of a compound of the formula IIb:

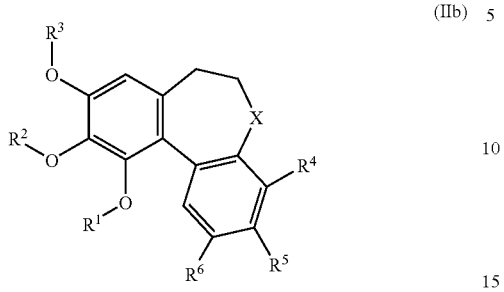

wherein

X is —C(O)—, —C(S)—, or —CH($R^7$)— wherein $R^7$ is hydrogen, hydroxy or —$NR^8R^9$ (wherein $R^8$ is a group —$Y^1R^{10}$ (wherein $Y^1$ is a direct bond, —C(O)—, —C(S)—, —C(O)O—, —C(O)$NR^{11}$—, —$SO_2$— or —$SO_2NR^{12}$— (wherein $R^{11}$ and $R^{12}$, which may be the same or different, each independently represents hydrogen, $C_{1-3}$alkyl or $C_{1-3}$alkoxy$C_{2-3}$alkyl) and $R^{10}$ is selected from one of the following two groups:

1) hydrogen, $C_{1-7}$alkyl or $C_{3-7}$cycloalkyl
 (which alkyl or cycloalkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, phenyl, nitro, sulphate, phosphate and a group —$Y^2R^{13}$ (wherein $Y^2$ is —$NR^{14}$C(O)— or —O—C(O)— (wherein $R^{14}$ represents hydrogen, $C_{1-3}$alkyl or $C_{1-3}$alkoxy$C_{2-3}$alkyl) and $R^{13}$ is $C_{1-7}$alkyl, $C_{3-7}$cycloalkyl or a group $R^{15}$ wherein $R^{15}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{16}R^{17}$ and —$NR^{18}COR^{19}$ (wherein $R^{16}$, $R^{17}$, $R^{18}$ and $R^{19}$, which may be the same or different, each represents hydrogen, $C_{1-3}$alkyl or $C_{1-3}$alkoxy$C_{2-3}$alkyl))); and 2) $R^{15}$ wherein $R^{15}$ is as defined hereinbefore;

and $R^9$ is hydrogen, $C_{1-7}$alkyl or $C_{3-7}$cycloalkyl, which alkyl or cycloalkyl group may bear one or more substituents selected from $C_{1-4}$alkoxy and phenyl);

$R^1$, $R^2$ and $R^3$ are each independently hydrogen, $PO_3H_2$, sulphate, $C_{3-7}$cycloalkyl, $C_{2-7}$alkenyl, $C_{2-7}$alkynyl, $C_{1-7}$alkanoyl, a group $R^{20}C_{1-7}$alkyl (wherein $R^{20}$ is phenyl which may bear one or more substituents selected from $C_{1-4}$alkyl, $C_{1-4}$alkoxy, $C_{1-4}$aminoalkyl and $C_{1-4}$hydroxyalkoxy), $C_{1-7}$alkyl or $C_{1-7}$alkylsulphonyl
 (which alkyl or alkylsulphonyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^2R^{21}$ (wherein $Y^2$ is —$NR^{22}$C(O)— or —O—C(O)— (wherein $R^{22}$ represents hydrogen, $C_{1-3}$alkyl or $C_{1-3}$alkoxy$C_{2-3}$alkyl) and $R^{21}$ is $C_{1-7}$alkyl, $C_{3-7}$cycloalkyl or a group $R^{23}$ wherein $R^{23}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{24}R^{25}$ and —$NR^{26}COR^{27}$ (wherein $R^{24}$, $R^{25}$, $R^{26}$ and $R^{27}$, which may be the same or different, each represents hydrogen, $C_{1-3}$alkyl or $C_{1-3}$alkoxy$C_{2-3}$alkyl)));

with the proviso that at least two of $R^1$, $R^2$ and $R^3$ are $C_{1-7}$alkyl;

$R^4$ is hydrogen, cyano, halogeno, nitro, amino, hydroxy, $C_{1-7}$alkoxy, $C_{1-7}$thioalkoxy, $C_{1-7}$alkanoyl or $C_{1-7}$alkyl,
 (which alkyl group may bear one or more substituents selected from:
  halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^3R^{28}$ (wherein $Y^3$ is —$NR^{29}$C(O)— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl)));

$R^5$ and $R^6$ are each independently selected from hydrogen, —$OPO_3H_2$, cyano, halogeno, nitro, amino, carboxy, hydroxy, $C_{1-7}$alkoxy, $C_{1-7}$alkanoyl, $C_{1-7}$thioalkoxy, $C_{1-7}$alkyl,
 (which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, sulphate, phosphate and a group —$Y^3R^{28}$ (wherein $Y^3$ is —$NR^{29}$C(O)— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl)), and a group —$Y^4R^{35}$
 (wherein $Y^4$ is —C(O)—, —OC(O)—, —O—, —SO—, —$SO_2$—, —$OSO_2$—, —$NR^{36}$—, —$NR^{37}$C(O)—, —OC(O)O—, —C(O)$NR^{38}$— or —$NR^{39}$C(O)O— (wherein $R^{36}$, $R^{37}$, $R^{38}$ and $R^{39}$, which may be the same or different, each represents hydrogen, $C_{1-3}$alkyl or $C_{1-3}$alkoxy$C_{2-3}$alkyl) and $R^{35}$ is a sugar moiety, a mono-peptide, a di-peptide, a tri-peptide, a tetra-peptide, sulphate, $C_{1-7}$alkyl, $C_{1-7}$alkoxy, $C_{1-7}$alkanoyl, amino$C_{1-7}$alkylamino, $C_{1-7}$alkylamino$C_{1-7}$alkylamino, di($C_{1-7}$alkyl)amino$C_{1-7}$alkylamino, $C_{1-7}$alkylphosphate (which alkyl, alkoxy, alkanoyl, aminoalkylamino, alkylaminoalkylamino, dialkylaminoalkylamino, or alkylphosphate may bear one or more substituents selected from:

halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^5R^{40}$ (wherein $Y^5$ is —$NR^{41}C(O)$—, —$C(O)NR^{42}$—, —$C(O)$—$O$— or —$O$—$C(O)$— (wherein $R^{41}$ and $R^{42}$ which may be the same or different each represents hydrogen, $C_{1-3}$alkyl or $C_{1-3}$alkoxy$C_{2-3}$alkyl) and $R^{40}$ is $C_{1-7}$alkyl, $C_{3-7}$cycloalkyl, carboxy$C_{1-7}$alkyl or a group $R^{43}$ wherein $R^{43}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{44}R^{45}$ and —$NR^{46}COR^{47}$ (wherein $R^{44}$, $R^{45}$, $R^{46}$ and $R^{47}$, which may be the same or different, each represents hydrogen, $C_{1-3}$alkyl or $C_{1-3}$alkoxy$C_{2-3}$alkyl))), $R^{48}$ (wherein $R^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, phenyl, cyano, —$CONR^{49}R^{50}$ and —$NR^{51}COR^{52}$ (wherein $R^{49}$, $R^{50}$, $R^{51}$ and $R^{52}$, which may be the same or different, each represents hydrogen, $C_{1-3}$alkyl or $C_{1-3}$alkoxy$C_{2-3}$alkyl)), or $R^{53}$ (wherein $R^{53}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl, $C_{1-4}$alkylsulphonyl$C_{1-4}$alkyl and $R^{54}$ (wherein $R^{54}$ is a 5–6-membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl)));

with the proviso that $R^5$ is not hydroxy, alkoxy, substituted alkoxy, —$OPO_3H_2$, —$O$—$C_{1-7}$alkanoyl or benzyloxy;

with the further proviso that at least one of $R^5$ or $R^6$ is a group —$Y^4R^{35}$ (wherein $Y^4$ and $R^{35}$ are as defined hereinbefore) but with the further provisos that when $R^5$ is —$Y^4R^{35}$ and $R^6$ is hydrogen or methoxy —$Y^4R^{35}$ is not selected from cases wherein:

$Y^4$ is —$C(O)$—, —$OC(O)$—, —$O$—, —$SO$—, —$OSO_2$—, —$NR^{36}$—, —$NR^{37}C(O)$— or —$C(O)NR^{38}$— (wherein $R^{36}$, $R^{37}$ and $R^{38}$, which may be the same or different, each represents hydrogen, $C_{1-3}$alkyl or $C_{1-3}$alkoxy$C_{2-3}$alkyl) and $R^{35}$ is a mono-peptide, a di-peptide, a tri-peptide, a tetra-peptide, $C_{1-7}$alkyl, $C_{1-7}$alkoxy, $C_{1-7}$alkanoyl, (which alkyl, alkoxy or alkanoyl may bear one or more substituents selected from: halogeno, hydroxy, and a group —$Y^5R^{40}$ (wherein $Y^5$ is —$C(O)$—$O$— or —$O$—$C(O)$— and $R^{40}$ is $C_{1-7}$alkyl)), or $R^{48}$ (wherein $R^{48}$ is a phenyl group or a benzyl group which phenyl or benzyl group may bear one or more substituents selected from $C_{1-7}$alkyl); and that when $R^6$ is —$Y^4R^{35}$ and $R^5$ is hydrogen, hydroxy or methoxy —$Y^4R^{35}$ is not selected from cases wherein:

$Y^4$ is —$C(O)$—, —$O$— or —$OSO_2$— and $R^{35}$ is $C_{1-7}$alkyl, $C_{1-7}$alkoxy (which alkyl, alkoxy or alkanoyl may bear one or more substituents selected from: halogeno), $R^{48}$ (wherein $R^{48}$ is a benzyl group which phenyl or benzyl group may bear one or more substituents selected from $C_{1-7}$alkyl), or $R^{53}$ (wherein $R^{53}$ is piperidinyl);

and salts thereof, pharmaceutically acceptable salts thereof, solvates and hydrates thereof, and prodrugs thereof for example esters, amides and sulphides, in the manufacture of a medicament for use in the production of a vascular damaging effect in warm-blooded animals such as humans.

According to a further aspect of the present invention there is provided a compound of the formula IIb as defined hereinbefore, and salts thereof, pharmaceutically acceptable salts thereof, solvates and hydrates thereof, and prodrugs thereof for example esters, amides and sulphides.

Preferred compounds of the present invention include:

(5S)-5-(acetylamino)-9,10,11-trimethoxy-6,7-dihydro-5H-dibenzo[a,c]cyclohepten-3-yl 3-{[(2R)-2,6-diaminohexanoyl]amino}propanoate, (5S)-5-(acetylamino-9,10,11-trimethoxy-6,7-dihydro-5H-dibenzo[a,c]cyclohepten-3-yl 3-[(2-aminoacetyl)amino]propanoate, N-([(5S)-5-(acetylamino)-9,10,11-trimethoxy-6,7-dihydro-5H-dibenzo[a,c]cyclohepten-3-yl]oxymethyl)-2-morpholinoacetamide, (2S,3S,4S,5R,6R)-6-{[(5S)-5-(acetylamino)-9,10,11-trimethoxy-6,7-dihydro-5H-dibenzo[a,c]cyclohepten-3-yl]oxy}-3,4,5-trihydroxytetrahydro-2H-pyran-2-carboxylic acid, N-[(5S)-3-(4-{4-methylpiperazin-1-ylmethyl}phenylcarbonyloxy)-9,10,11-trimethoxy-6,7-dihydro-5H-dibenzo[a,c]cyclohepten-5-yl]acetamide, N-[(5S)-3-(4-{morpholinomethyl}phenylcarbonyloxy)-9,10,11-trimethoxy-6,7-dihydro-5H-dibenzo[a,c]cyclohepten-5-yl]acetamide, (5S)-5-(acetylamino)-9,10,11-trimethoxy-6,7-dihydro-5H-dibenzo[a,c]cyclohepten-3-yl 3-[4-methylpiperazin-1-ylcarbonyl]propanoate, 5-[{(5S)-5-(acetylamino)-9,10,11-trimethoxy-6,7-dihydro-5H-dibenzo[a,c]cyclohepten-3-yl}oxycarbonyl]pentanoic acid, 4-(3-[(5S)-5-(acetylamino)-9,10,11-trimethoxy-6,7-dihydro-5H-dibenzo[a,c]cyclohepten-3-yl]oxy-3-oxopropyl) benzoic acid and (2S)-N-[(5S)-5-(acetylamino)-9,10,11-trimethoxy-6,7-dihydro-5H-dibenzo[a,c]cyclohepten-3-yl]-2-amino-3-hydroxypropanamide, and salts thereof, pharmaceutically acceptable salts thereof, solvates and hydrates thereof, and prodrugs thereof.

More preferred compounds of the present invention include:
(5S)-5-(acetylamino)-9,10,11-trimethoxy-6,7-dihydro-5H-dibenzo[a,c]cyclohepten-3-yl 3-{[(2R)-2,6-diaminohexanoyl]amino}propanoate,
(5S)-5-(acetylamino)-9,10,11-trimethoxy-6,7-dihydro-5H-dibenzo[a,c]cyclohepten-3-yl 3-[(2-aminoacetyl)amino]propanoate,
N-[(5S)-3-(4-{4-methylpiperazin-1-ylmethyl}phenylcarbonyloxy)-9,10,11-trimethoxy-6,7-dihydro-5H-dibenzo[a,c]cyclohepten-5-yl]acetamide,
N-[(5S)-3-(4-{morpholinomethyl}phenylcarbonyloxy)-9,10,11-trimethoxy-6,7-dihydro-5H-dibenzo[a,c]cyclohepten-5-yl]acetamide,
(5S)-5-(acetylamino)-9,10,11-trimethoxy-6,7-dihydro-5H-dibenzo[a,c]cyclohepten-3-yl 3-[4-methylpiperazin-1-ylcarbonyl]propanoate,
5-[{(5S)-5-(acetylamino)-9,10,11-trimethoxy-6,7-dihydro-5H-dibenzo[a,c]cyclohepten-3-yl}oxycarbonyl]pentanoic acid,
4-(3-[(5S)-5-(acetylamino)-9,10,11-trimethoxy-6,7-dihydro-5H-dibenzo[a,c]cyclohepten-3-yl]oxy-3-oxopropyl) benzoic acid and
(2S)-N-[(5S)-5-(acetylamino)-9,10,11-trimethoxy-6,7-dihydro-5H-dibenzo[a,c]cyclohepten-3-yl]-2-amino-3-hydroxypropanamide, and salts thereof, pharmaceutically acceptable salts thereof, solvates and hydrates thereof, and prodrugs thereof.

Especially preferred compounds of the present invention include:
N-[(5S)-3-(4-{4-methylpiperazin-1-ylmethyl}phenylcarbonyloxy)-9,10,11-trimethoxy-6,7-dihydro-5H-dibenzo[a,c]cyclohepten-5-yl]acetamide and
(2S)-N-[(5S)-5-(acetylamino)-9,10,11-trimethoxy-6,7-dihydro-5H-dibenzo[a,c]cyclohepten-3-yl]-2-amino-3-hydroxypropanamide, and salts thereof, pharmaceutically acceptable salts thereof, solvates and hydrates thereof, and prodrugs thereof.

In another embodiment of the present invention preferred compounds include (2S)-N-[(5S)-5-(acetylamino)-9,10,11-trimethoxy-6,7-dihydro-5H-dibenzo[a,c]cyclohepten-3-yl]-2-amino-5-[(2-nitroethanimidoyl)amino]pentanamide, and salts thereof, pharmaceutically acceptable salts thereof, solvates and hydrates thereof, and prodrugs thereof.

In one embodiment of the invention preferred compounds include those in which $R^1$, $R^2$ and $R^3$ are each alkyl, $Y^4$ is NH and $R^{35}$ is an acyl group derived from a natural alpha-amino acid such as glycine, L-alanine or L-serine.

In one embodiment of the invention more preferred compounds include compounds wherein $R^1$, $R^2$ and $R^3$ are each methyl, $R^4$ is hydrogen and X is —CH(NHC(O)CH$_3$)—.

In another embodiment of the invention particular compounds include compounds wherein $R^1$, $R^2$ and $R^3$ are each alkyl and $R^{35}$ is aminoC$_{1-7}$alkylamino, C$_{1-7}$alkylamino C$_{1-7}$alkylamino, di(C$_{1-7}$alkyl)aminoC$_{1-7}$alkylamino, 1-piperazinyl or 4-(piperidino)piperidin-1-yl.

In another embodiment of the invention further particular compounds include compounds wherein $R^1$, $R^2$ and $R^3$ are each alkyl, $R^4$ is hydrogen and X is —CH(NHC(O)CH$_3$)—.

In another embodiment of the invention more particular compounds include compounds wherein $R^1$, $R^2$ and $R^3$ are each alkyl and $R^4$ and $R^6$ are each hydrogen.

In another embodiment of the invention especially preferred compounds include compounds wherein $R^1$, $R^2$ and $R^3$ are each methyl and $R^{35}$ is a substituted acyl group. Preferred compounds of the present invention include:

N-[3-(alanylamino)-9,10,11-trimethoxy-6,7-dihydro-5H-dibenzo[a,c]cyclohepten-5-yl]acetamide and salts thereof, pharmaceutically acceptable salts thereof, solvates and hydrates thereof, and prodrugs thereof for example esters, amides and sulphides. A preferred compound for use in the manufacture of a medicament for use in the production of a vascular damaging effect in warm-blooded animals such as humans is N-[3-amino-9,10,11-trimethoxy-6,7-dihydro-5H-dibenzo[a,c]cyclohepten-5-yl]acetamide.

For the avoidance of doubt it is to be understood that where in this specification a group is qualified by 'hereinbefore defined' or 'defined hereinbefore', or 'hereinafter defined' or 'defined hereinafter', the said group encompasses the first occurring and broadest definition as well as each and all of the preferred definitions for that group.

In this specification unless stated otherwise the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–7 carbon atoms, preferably 1–4 carbon atoms. The term "alkoxy" as used herein, unless stated otherwise includes "alkyl"—O— groups in which "alkyl" is as hereinbefore defined. The term "aryl" as used herein unless stated otherwise includes reference to a $C_{6-10}$aryl group which may, if desired, carry one or more substituents selected from halogeno, alkyl, haloalkyl, alkoxy, hydroxy, amino, nitro and cyano, (wherein alkyl, haloalkyl and alkoxy are as hereinbefore and hereinafter defined). The term "aryloxy" as used herein unless otherwise stated includes "aryl"—O—groups in which "aryl" is as hereinbefore defined. The term "sulphonyloxy" as used herein refers to alkylsulphonyloxy and arylsulphonyloxy groups in which "alkyl" and "aryl" are as hereinbefore defined. The term "heteroaryl" as used herein unless stated otherwise includes reference to a $C_{6-10}$aryl group containing one or more ring heteroatoms selected from O, N and S which heteroaryl group may, if desired, carry one or more substituents selected from halogeno, alkyl, haloalkyl, alkoxy, hydroxy, amino, nitro and cyano, (wherein alkyl, haloalkyl and alkoxy are as hereinbefore and hereinafter defined). The term "alkanoyl" as used herein unless otherwise stated includes formyl and alkylC═O groups in which "alkyl" is as defined hereinbefore, for example C$_2$alkanoyl is ethanoyl and refers to CH$_3$C═O, C$_1$alkanoyl is formyl and refers to CHO. In this specification unless stated otherwise the term "alkenyl" includes both straight and branched chain alkenyl groups but references to individual alkenyl groups such as 2-butenyl are specific for the straight chain version only. Unless otherwise stated the term "alkenyl" advantageously refers to chains with 2–7 carbon atoms, preferably 2–4 carbon atoms. In this specification unless stated otherwise the term "alkynyl" includes both straight and branched chain alkynyl groups but references to individual alkynyl groups such as 2-butynyl are specific for the straight chain version only. Unless otherwise stated the term "alkynyl" advantageously refers to chains with 2–7 carbon atoms, preferably 2–4 carbon atoms. The term "halogeno" means fluoro, chloro, bromo or iodo unless otherwise stated. A haloalkyl group is an alkyl group as defined hereinbefore substituted with one or more halogeno groups for example trifluoromethyl and dichloromethyl. A hydroxyalkyl group is an alkyl group as defined hereinbefore substituted with one or more hydroxy groups.

In this specification unless stated otherwise the term "acyl" refers to a group linked via a carbonyl group. "Acyl" includes a group —C(O)—$R^{58}$ wherein $R^{58}$ is an alkyl, aryl or heteroaryl group as hereinbefore defined, or —C(O)—$R^{58}$ is derived from an amino acid.

In this specification mono-peptide means an amino acid including α-amino acids β-amino acids and γ-amino acids. The amino acids may be L-isomers or D-isomers, preferably L-isomers. Preferred amino acids include glycine, alanine, valine, leucine, isoleucine, methionine, proline, phenylalanine, tryptophan, serine, threonine, cysteine, tyrosine, asparaginine, glutamine, aspartic acid, glutamic acid, lysine, arginine, histidine, β-alanine and ornithine. More preferred amino acids include serine, threonine, arginine, glycine, alanine, β-alanine and lysine. Especially preferred amino acids include serine, threonine, arginine, alanine and β-alanine.

An aromatic heterocyclic group includes those selected from pyridyl, pyrimidyl, furyl, thienyl, pyrrolyl, pyrazolyl, indolyl, benzofuryl, benzothienyl, benzothiazolyl, oxazolyl, isoxazolyl, thiazolyl, isothiazolyl, imidazolyl, triazolyl, quinolyl and isoquinolyl.

For the avoidance of any doubt, it is to be understood that when $Y^1$ is, for example, a group of formula —C(O)$NR^{11}$—, it is the nitrogen atom bearing the $R^{11}$ group which is attached to the group $R^{10}$ and the carbonyl group (C(O)) is attached to the nitrogen atom which is linked to the hepten ring. A similar convention applies to the other two atom $Y^1$ linking groups such as —$SO_2NR^{12}$—. An analogous convention applies to other groups. It is further to be understood that when $Y^1$ represents —C(O)$NR^{11}$— and $R^{11}$ is $C_{1-3}$alkoxy$C_{2-3}$alkyl it is the $C_{2-3}$-alkyl moiety which is linked to the nitrogen atom of $Y^1$ and an analogous convention applies to other groups.

For the avoidance of any doubt it is to be understood that when $Y^1$ is, for example, a group of formula —OC(O)— it is the oxygen atom which is bound to the substituted group and the carbonyl group (C(O)) which is bound to $R^{13}$ and an analogous convention applies to other groups.

For the avoidance of any doubt it is to be understood that when $Y^4$ is, for example, a group of formula —$NR^{39}$C(O)O— it is the nitrogen atom which is bound to the benz ring and the oxygen atom which is bound to $R^{35}$ and an analogous convention applies to other groups.

For the avoidance of any doubt it is to be understood that when $R^{35}$ is a group $C_{1-7}$alkyl$R^{48}$ it is the alkyl chain which is linked to $Y^4$, similarly when $R^{35}$ is a group $(CH_2)_aY^6(CH_2)_bR^{53}$ it is the $(CH_2)_a$ group which is linked to $Y^4$ and a similar convention applies to other groups.

For the avoidance of any doubt it is to be understood that when a group carries a $C_{1-4}$alkylamino substituent it is the amino moiety which is attached to the group whereas when a group carries a $C_{1-4}$aminoalkyl substituent it is the $C_{1-4}$alkyl moiety which is attached to the group and an analogous convention applies to other substituents.

Within the present invention it is to be understood that a compound of the formula I or a salt thereof may exhibit the phenomenon of tautomerism and that the formulae drawings within this specification can represent only one of the possible tautomeric forms. It is to be understood that the invention encompasses any tautomeric form which has vascular damaging activity and is not to be limited merely to any one tautomeric form utilised within the formulae drawings. The formulae drawings within this specification can represent only one of the possible tautomeric forms and it is to be understood that the specification encompasses all possible tautomeric forms of the compounds drawn not just those forms which it has been possible to show graphically herein.

It will be appreciated that compounds of the formula I or a salt thereof may possess an asymmetric carbon atom. Such an asymmetric carbon atom is also involved in the tautomerism described above, and it is to be understood that the present invention encompasses any chiral form (including both pure enantiomers and racemic mixtures), as well as any tautomeric form, which has vascular damaging activity, and is not to be limited merely to any one tautomeric form or chiral form utilised within the formulae drawings. It is to be understood that the invention encompasses all optical and diastereomers which have vascular damaging activity.

It is also to be understood that certain compounds of the formula I and salts thereof can exist in solvated as well as unsolvated forms such as, for example, hydrated forms. It is to be understood that the invention encompasses all such solvated forms which have vascular damaging activity.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

Compounds of Formula I may be prepared by any process known to a person skilled in the art. Such processes include, for example, solid phase synthesis. Compounds of Formula I may be prepared by a number of processes as generally described hereinbelow and more specifically in the Examples hereinafter. In the general preparations described hereinafter it may be necessary to employ protecting groups which are then removed during the final stages of the synthesis. The appropriate use of such protecting groups and processes for their removal will be readily apparent to those skilled in the art. Processes for the preparation of novel compounds of formula I, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus, the following processes (a) to (i) and (i) to (iii) constitute further features of the present invention.

Synthesis of Compounds of Formula I (a) Thus according to a further aspect of the invention a compound of formula I, in which $R^5$ or $R^6$ is a group $Y^4R^{35}$ (wherein $R^{35}$ is as defined hereinbefore and $Y^4$ is a group —OC(O)— or —NHC(O)—), can be prepared from a compound of formula III or IV:

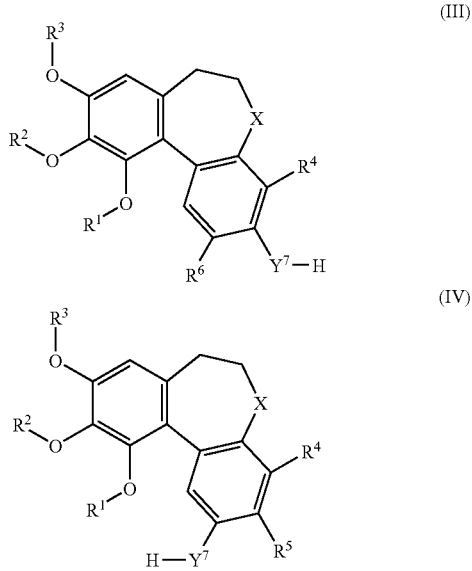

(wherein X, $R^1$, $R^2$, $R^3$, $R^4$, $R^5$, $R^6$ are as defined hereinbefore and $Y^7$ is —O— or —NH—), as appropriate, by standard acylation or coupling conditions including, for example, treatment of a compound of formula III or IV with a substituted carboxylic acid in the presence of a coupling agent such as dicyclohexylcarbodiimide or 1-(3-dimethylaminopropyl)-3-ethylcarbodiimide and, optionally, a base such as an organic base for example triethylamine in a solvent such as an aprotic solvent for example dimethylformamide or in a chlorinated solvent for example trichloromethane or dichloromethane at a temperature in the range from about −30° C. to about 60° C., conveniently at or near ambient temperature.

(b) In another general example a compound of formula I, in which $R^5$ or $R^6$ is a group $Y^4R^{35}$ (wherein $R^{35}$ is $C_{1-7}$alkoxy which may be substituted as defined hereinbefore and $Y^4$ is a group —OC(O)— or —NHC(O)—), can be prepared from a compound of formula III and IV, as appropriate, by standard acylation reactions including, for example, treatment of a compound of formula III or IV with a substituted alkylchloroformate in the presence of a base such as an organic base for example, triethylamine or N-methylmorpholine in a solvent such as an ether solvent for example tetrahydrofuran or in a chlorinated solvent for example dichloromethane at a temperature in the range from about −20° C. to the reflux temperature of the solvent.

(c) In a further general example a compound of formula I, in which $R^5$ or $R^6$ is a group $Y^4R^{35}$ (wherein $R^{35}$ is amino$C_{1-7}$alkylamino, $C_{1-7}$alkylamino$C_{1-7}$alkylamino, di($C_{1-7}$alkyl)amino$C_{1-7}$alkylamino and may be substituted as defined hereinbefore, or is $R^{53}$ (wherein $R^{53}$ is as defined hereinbefore) and $Y^4$ is a group —OC(O)— or —NHC(O)—), can be prepared from a compound of formula III or IV, as appropriate, by standard acylation reactions including, for example, treatment of a compound of formula III or IV with a substituted alkylisocyanate or a carbamoyl chloride in the presence of a base such as an organic base for example triethylamine, pyridine or N-methylmorpholine in a solvent such as an ether solvent for example tetrahydrofuran or in a chlorinated solvent for example dichloromethane at a temperature in the range from about −20° C. to the reflux temperature of the solvent.

(d) In a further example a compound of formula I, in which $R^5$ or $R^6$ is a group $Y^4R^{35}$ (wherein $R^{35}$ is a sugar moiety and $Y^4$ is a group —O— or —NH—), can be prepared from a compound of formula III or IV, as appropriate, by standard glycosylation reactions including for example treatment of a compound of formula III or IV with a suitably protected 1-bromo sugar in a solvent such as a chlorinated solvent for example trichloromethane or an aromatic solvent for example toluene at a temperature in the range from about 0° C. to the reflux temperature of the solvent, followed by deprotection. Suitable protecting groups include acetyl groups for the sugar hydroxyl groups and esters for sugar carboxylic acids.

(e) In a further example a compound of formula I in which $R^5$ or $R^6$ is a group $Y^4R^{35}$ (wherein $R^{35}$ is sulphate and $Y^4$ is a group —O— or —NH—), can be prepared from a compound of formula III or IV, as appropriate, by standard sulphonylation reactions including for example treatment of a compound of formula III or IV with chlorosulphonic acid in the presence of a base such as dimethylaniline in a chlorinated solvent such as trichloromethane at a temperature in the range from about −20° C. to about 60° C., or more preferably with chlorosulphonic acid in pyridine at a temperature in the range from about −20° C. to about 60° C.

(f) In a further example a compound of formula I in which $R^5$ or $R^6$ is a group $Y^4R^{35}$ (wherein $R^{35}$ is $C_{1-7}$alkylphosphate and may be substituted as defined hereinbefore and $Y^4$ is a group —O— or —NH—), can be prepared from a compound of formula III or IV, as appropriate, by standard phosphorylation reactions including for example treatment of a compound of formula III or IV with phosphorous oxychloride in the presence of a base such as triethylamine in a chlorinated solvent such as trichloromethane at a temperature in the range from about −20° C. to about 60° C., followed by treatment with an alcohol, or more preferably with alkyl dichlorophosphate in the presence of a base such as lithiumHMDS in THF at a temperature in the range from about −20° C. to about 60° C., followed by treatment with water.

(g) Compounds of formula I in which $R^5$ is amino can be prepared from carboxylic acids of formula V:

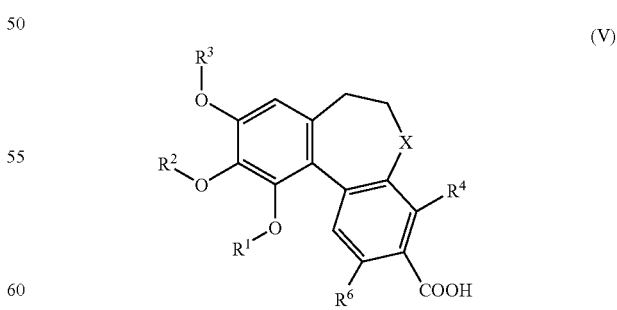

(wherein X, $R^1$, $R^2$, $R^3$, $R^4$ and $R^6$ are as defined hereinbefore) via Curtius rearrangement and hydrolysis (V. Fernholz Justus Liebigs Ann., 1950, 568, 63–72).

(h) Compounds of formula I may also be prepared from other compounds of formula I by chemical modification.

Examples of such chemical modifications that may be applied are standard alkylation, arylation, heteroarylation, acylation, thioacylation, sulphonylation, sulphation, phosphorylation, aromatic halogenation and coupling reactions. These reactions may be used to add new substituents or to modify existing substituents. Alternatively, existing substituents in compounds of formula I may be modified by, for example, oxidation, reduction, elimination, hydrolysis or other cleavage reaction to yield other compounds of formula I.

(i) A compound of formula I in which $R^5$ or $R^6$ is chloro may be prepared from a compound of formula III or IV by standard processes such as the Sandmeyer reaction.

Thus for example a compound of formula I containing an amino group may be acylated on the amino group by treatment with, for example, an acyl halide or anhydride in the presence of a base, for example a tertiary amine base such as triethylamine, in for example, a solvent such as a hydrocarbon solvent e.g. dichloromethane at a temperature in the range for example –30° C. to 120° C., conveniently at or near ambient temperature.

In another general example of an interconversion process an amino group in a compound of formula I may be sulphonylated by treatment with, for example, an alkyl or aryl sulphonyl chloride or an alkyl or aryl sulphonic anhydride in the presence of a base, for example a tertiary amine base such as triethylamine, in for example a solvent such as a hydrocarbon solvent e.g. dichloromethane at a temperature in the range for example –30° C. to 120° C., conveniently at or near ambient temperature.

In a further general example a compound of formula I containing a hydroxy group can be converted into the corresponding dihydrogenphosphate ester by treatment with for example di-tert-butyl diisopropylphosphoramidite or di-tert-butyl diethylphosphoramidite in the presence of a suitable catalyst for example tetrazole in a solvent such as an ether solvent for example tetrahydrofuran at a temperature in the range –40° C. to 40° C., conveniently at or near ambient temperature, followed by treatment with an oxidising agent for example 3-chloroperoxy benzoic acid at a temperature in the range –78° C. to 40° C. preferably –40° C. to 10° C. The resulting intermediate phosphate triester is treated with an acid for example trifluoroacetic acid in a solvent such as a chlorinated solvent e.g. dichloromethane at a temperature in the range –30° C. to 40° C. conveniently at or near 0° C. to give the compound of formula I containing a dihydrogenphosphate ester.

In a further general example a compound of formula I containing an amide can be hydrolysed by treatment with for example an acid such as hydrochloric acid in a solvent such as an alcohol, for example methanol at an elevated temperature conveniently at the reflux temperature.

In another general example an O-alkyl group may be cleaved to the corresponding alcohol (OH) by reaction with boron tribromide in a solvent such as a chlorinated solvent e.g. dichloromethane as a low temperature e.g. around –78° C.

In a further general example compounds of formula I may be alkylated by reaction with a suitable alkylating agent such as an alkyl halide, an alkyl toluenesulphonate, an alkyl methanesulphonate or an alkyl triflate. The alkylation reaction can be carried out in the presence of a base for example an inorganic base such as a carbonate e.g. caesium or potassium carbonate, a hydride such as sodium hydride or an alkoxide such as potassium t-butoxide in a suitable solvent such as an aprotic solvent e.g. dimethylformamide or an ether solvent such as tetrahydrofuran at a temperature of around –10° C. to 80° C.

Synthesis of Intermediates (i) Compounds of formula III or IV, used as starting materials for the preparation of compounds of the invention are either known or can be prepared from known compounds by the application of standard procedures of organic synthesis known in the art. For example a compound of formula VI:

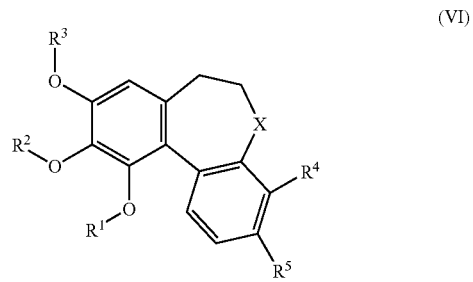

(VI)

(wherein X, $R^1$, $R^2$, $R^3$, $R^4$ and $R^5$ are as defined hereinbefore), can be converted into a compound of formula IV where $Y^7$ is NH by the sequential application of standard nitration conditions followed by reduction of the incorporated nitro group under standard reduction conditions. Suitable nitration conditions include, for example, treatment with concentrated nitric acid in a solvent such as glacial acetic acid at a temperature from about –40° C. to about 40° C. Suitable reduction conditions include, for example, treatment with tin(II) chloride in a solvent such as hydrochloric acid, with or without an alcoholic cosolvent, at a temperature between ambient temperature and about 100° C.

(ii) Compounds of formulae III or IV can also be prepared from other compounds of formulae III or IV by chemical modification. For example a compound of formula IV in which $Y^7$ is NH can be converted into the corresponding compound in which $Y^7$ is O by treatment with sodium nitrite in sulphuric acid at around 0° C. followed by heating to around 100° C.

Preparation of a compound of formula I as a single enantiomer or, where appropriate, diastereomer may be effected by synthesis from an enantiomerically pure starting material or intermediate or by resolution of the final product in a conventional manner.

Acid addition salts of the compounds of formula I are prepared in a conventional manner by treating a solution or suspension of the free base I with about one equivalent of a pharmaceutically acceptable acid. Salts of compounds of formula I derived from inorganic or organic bases are prepared in a conventional manner by treating a solution or suspension of the free acid I with about one equivalent of a pharmaceutically acceptable organic or inorganic base. Alternatively both acid addition salts and salts derived from bases may be prepared by treatment of the parent compound with the appropriate ion-exchange resin in a standard fashion. Conventional concentration and recrystallisation techniques are employed in isolating the salts.

(iii) Compounds of formula V may be prepared from the corresponding colchicine derivatives by treatment with sodium methoxide in methanol followed by ester hydrolysis with aqueous acid or aqueous base (V. Fernholz Justus Liebigs Ann., 1950, 568, 63–72). Compounds of formula VI may be prepared by any of the methods described for compounds of formula I.

Many of the intermediates defined herein, for example, those of the formula III, IV, V, and VI are novel and these are provided as a further feature of the invention. The preparation of these compounds is as described herein and/or is by methods well known to persons skilled in the art of organic chemistry.

Compounds according to the invention are able to destroy vasculature that has been newly formed such as tumour vasculature while leaving unaffected normal, mature vasculature. The identification of compounds which selectively, and preferably potently, damage newly-formed vasculature is desirable and is the subject of the present invention. The ability of the compounds to act in this way may be assessed, for example, using one or more of the procedures set out below:

(a) Activity Against Tumour Vasculature Measured by Radioactive Tracer

This assay demonstrates the ability of compounds to damage selectively tumour vasculature.

Subcutaneous CaNT tumours were initiated by injecting 0.05 ml of a crude tumour cell suspension, approximately $10^6$ cells, under the skin overlying the rear dorsum of 12–16 week-old mice. The animals were selected for treatment after approximately 3–4 weeks, when their tumours reached a geometric mean diameter of 5.5–6.5 mm. Compounds were dissolved in sterile saline and injected intraperitoneally in a volume of 0.1 ml per 10 g body weight. Tumour perfusion was measured 6 hours after intraperitoneal administration in tumour, kidney, liver, skin, muscle, gut and brain by the $^{86}$RbCl extraction technique (Sapirstein, Amer. Jnl. Physiol., 1958, 193, 161–168). Tissue radioactivity measured 1 minute after an intravenous injection of $^{86}$RbCl was used to calculate relative blood flow as a proportion of cardiac output (Hill and Denekamp, Brit. Jnl. Radiol., 1982, 55, 905–913). Five animals were used in control and treated groups. Results were expressed as a percentage of the blood flow in the corresponding tissues in vehicle treated animals.

(b) Activity Against Tumour Vasculature Measured by Fluorescent Dye

This assay demonstrates the ability of compounds to damage tumour vasculature.

Tumour functional vascular volume of CaNT tumour-bearing mice was measured using the fluorescent dye Hoechst 33342 according to the method of Smith et al (Brit. Jnl. Cancer 1988, 57, 247–253). Five animals were used in control and treated group. The fluorescent dye was dissolved in saline at 6.25 mg/ml and injected intravenously at 10 mg/kg 24 hours after intraperitoneal drug treatment. One minute later, animals were killed and tumours excised and frozen; 10 µm sections were cut at 3 different levels and observed under UV illumination using an Olympus microscope equipped with epifluorescence. Blood vessels were identified by their fluorescent outlines and vascular volume was quantified using a point scoring system based on that described by Chalkley, (Jnl. Natl. Cancer Inst., 1943, 4, 47–53). All estimates were based on counting a minimum of 100 fields from sections cut at the 3 different levels.

The ability of the compounds to bind to preparations of mammalian tubulin can be evaluated by a number of methods available in the literature, for example by following temperature initiated tubulin polymerisation by turbidity in the absence and presence of the compound (for example O. Boye et al Med. Chem. Res., 1991, 1, 142–150).

The activity of N-[3-amino-9,10,11-trimethoxy-6,7-dihydro-5H-dibenzo[a,c]cyclohepten-5-yl]acetamide, (V. Fernholz Justus Liebigs Ann., 1950, 568, 63–72), against tumour vasculature was measured by the fluorescent dye method described above. This compound decreased perfused vascular volume by 88% relative to control when dosed at 50 mg/kg intraperitoneally. The $IC_{50}$ of this compound in a tubulin polymerisation assay was 58 micromolar (O. Boye et al Med. Chem. Res., 1991, 1, 142–150).

The activity of compounds Examples 2 and 3 (described hereinafter) against tumour vasculature was measured by the fluorescent dye method described hereinbefore.

| Compound of Example | % Decrease in vascular volume |
|---|---|
| 2 | 95 |
| 3 | 45 |

(c) HUVEC Detachment Assay

This assay examined the effects of compounds on the adherence of HUVECs to tissue culture plasticware.

HUVECs were plated in 0.2% gelatin-coated 12 well tissue culture plates at a concentration of $3\times10^4$ cells per well in 1 ml TCS medium. After 24 hours, when the cells were at ~30% confluency, the cells were dosed with compound for 40 minutes at 37° C., 5% $CO_2$. After this incubation the medium containing drug was pipetted off, and the cells were then gently washed in 2 mls of HBSS (Hanks' Balanced Salt Solution purchased from Life Technologies Ltd, Paisley UK; Catalogue # 24020-083) to remove any detached cells. The washing solution was then removed, and the adherent cells remaining were trypsinised using 300 µl of 1×Trypsin-EDTA solution (Life Technologies Ltd, Paisley, UK; Catalogue # 43500-019) at ambient temperature for 2 minutes. The trypsinised cells were then made up to 1 ml with TCS Biologicals medium, then centrifuged at 2000 rpm for 2 minutes. The cell pellet was then resuspended in a volume of 50 µl of TCS Biologicals medium. Total cell counts were obtained by counting the cells on a haemocytometer. The amount of cell detachment was calculated by comparing the number of cells remaining attached following treatment with the number in undosed control wells.

(d) Hras5 Necrosis Model

NIH 3T3 fibroblasts transfected with Harvey ras, clone 5, (Hras5 cells) were kept in continual passage in Dulbecco's modified Eagles medium (DMEM) containing 10% foetal bovine serum (FBS) and 1% glutamine, at 37° C. in a humidified incubator gassed with 7.5% carbon dioxide and 92.5% oxygen. Cells were implanted subcutaneously into the left flank of male nude mice (8–10 weeks of age) at an inoculum of $2\times10^5$ cells/mouse. Tumours were measured using calipers and randomised into groups of 2–4 mice between days 9–14 after implant. Mice were dosed with compounds, either intravenously or intraperitoneally, once on day of randomisation and culled 24 hours after dosing. Compounds were dissolved in 20% hydroxypropyl beta cyclodextrin in physiological saline at pH 7 and dosed in a volume of 0.1 ml per 10 g body weight. Tumours were excised, weighed and placed in buffered formalin. Area of necrosis in individual tumours was assessed from a haematoxylin/eosin stained-slide by a pathologist and scored from 0, meaning no significant change, to 10, meaning 91–100% necrosis.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for nasal administration or administration by inhalation, for example as a powder or solution, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly, the optimum dosage may be determined by the practitioner who is treating any particular patient.

According to a further aspect of the present invention there is provided a compound of the formula I or a pharmaceutically acceptable salt thereof as defined hereinbefore for use in a method of treatment of the human or animal body by therapy.

A further feature of the present invention is a compound of formula I, or a pharmaceutically acceptable salt thereof, for use as a medicament, conveniently a compound of formula I, or a pharmaceutically acceptable salt thereof, for use as a medicament for producing a vascular damaging effect in a warm-blooded animal such as a human being.

Thus according to a further aspect of the invention there is provided the use of a compound of the formula I, or a pharmaceutically acceptable salt thereof in the manufacture of a medicament for use in the production of a vascular damaging effect in a warm-blooded animal such as a human being.

According to a further feature of the invention there is provided a method for producing a vascular damaging effect in a warm-blooded animal, such as a human being, in need of such treatment which comprise administering to said animal an effective amount of a compound of formula I or a pharmaceutically acceptable salt thereof as defined hereinbefore.

The antiangiogenic treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic treatment defined hereinbefore may be: surgery, radiotherapy or chemotherapy. Such chemotherapy may include the following categories of therapeutic agent:

(i) other antiangiogenic agents that work by different mechanisms from those defined hereinbefore (for example linomide, inhibitors of integrin $\alpha v \beta 3$ function, angiostatin, endostatin, razoxin, thalidomide) and including vascular endothelial growth factor (VEGF) receptor tyrosine kinase inhibitors (RTKIs) (for example those described in International Patent Applications Publication Nos. WO 97/22596, WO 97/30035, WO 97/32856 and WO 98/13354 the entire disclosure of which documents is incorporated herein by reference);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example epidermal growth factor (EGF), platelet derived growth factor and hepatocyte growth factor such inhibitors include growth factor antibodies, growth factor receptor antibodies, tyrosine kinase inhibitors and serine/threonine kinase inhibitors);

(iii) biological response modifiers (for example interferon);

(iv) antibodies (for example edrecolomab); and (v) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); enzymes (for example asparaginase); thymidylate synthase inhibitors (for example raltitrexed); topoisomerase inhibitors (for example epipodophyllotoxins like etoposide and teniposide, amsacrine, topotecan, irinotecan).

As stated above the compounds defined in the present invention are of interest for their vascular damaging effects. Such compounds of the invention are expected to be useful in the prophylaxis and treatment of a wide range of disease states where inappropriate angiogenesis occurs including cancer, diabetes, psoriasis, rheumatoid arthritis, Kaposi's sarcoma, haemangioma, acute and chronic nephropathies, atheroma, arterial restenosis, autoimmune diseases, acute inflammation, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin.

In addition to their use in therapeutic medicine, the compounds of formula I and their pharmaceutically acceptable salts are also useful as pharmacological tools in the development and standardisation of in vitro and in vivo test systems for the evaluation of the effects of vascular damaging agents in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon or nitrogen;

(iii) yields are given for illustration only and are not necessarily the maximum attainable;

(iv) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(v) intermediates were not generally fully characterised and purity was assessed by thin layer chromatography (TLC), high-performance liquid chromatography (HPLC), infra-red (IR) or NMR analysis;

| Abbreviations | |
|---|---|
| 1,3-Dicyclohexylcarbodiimide | DCCI |
| 4-Dimethylaminopyridine | DMAP |
| Tetrahydrofuran | THF |
| Diethyl azodicarboxylate | DEAD |
| N,N-Dimethylformamide | DMF |
| 1-(3-Dimethylaminopropyl)-3-ethylcarbodiimide hydrochloride | EDCI |
| Dimethyl sulphoxide | DMSO |
| Trifluoroacetic acid | TFA |
| 1,1,1,3,3-hexamethyldisilazane | HMDS |

EXAMPLE 1

N-[3-((N-benzyloxycarbonylalanyl)amino)-9,10,11-trimethoxy-6,7-dihydro-5H-dibenzo[a,c]cyclohepten-5-yl]acetamide A solution of N-benzyloxycarbonyl-(L)-alanine (63 mg, 0.28 mmol) in dichloromethane (4 ml) at −20° C. was treated with N-[3-amino-9,10,11-trimethoxy-6,7-dihydro-5H-dibenzo[a,c]cyclohepten-5-yl]acetamide (100 mg, 0.28 mmol), (V. Fernholz Justus Liebigs Ann., 1950, 568, 63–72), and 1,3-dicylcohexylcarbodiimide (134 mg, 0.31 mmol) and the solution stirred for 16 hours at ambient temperature. Solvent was evaporated under reduced pressure and the residue chromatographed on silica gel, eluting with ethyl acetate to give a white solid which was triturated with diethyl ether. The title compound (85 mg) was obtained as a white solid.

m.p. 140–141° C.

m/e 561

EXAMPLE 2

N-[3-(alanylamino)-9,10,11-trimethoxy-6,7-dihydro-5H-dibenzo[a,c]cyclohepten-5-yl]acetamide A solution of N-[3-((N-benzyloxycarbonylalanyl)amino)-9,10,11-trimethoxy-6,7-dihydro-5H-dibenzo[a,c]cyclohepten-5-yl]acetamide (70 mg, 0.125 mmol), (prepared as described in Example 1), in ethanol (2 ml) was hydrogenated at atmospheric pressure over 5% palladium on carbon (10 mg) for 2 hours. Ethanol (3 ml) was added and the solution was filtered through diatomaceous earth and the filtrate concentrated under reduced pressure. Trituration with ethyl acetate/diethyl ether gave the title compound (35 mg) as a white solid.

m.p. 170–173° C.

m/e 427

EXAMPLE 3

N-[3-(4-(1-piperidinyl)piperidinylcarbonyloxy)-9,10,11-trimethoxy-6,7-dihydro-5H-dibenzo[a,c]cyclohepten-5-yl]acetamide A solution of N-acetyl-colchinol (300 mg, 0.84 mmol), (J. Cech F. Santacy Collect. Czech Comm 1949, 4, 532–539), in pyridine (5 ml) was treated with 4-piperidinopiperidine carbamoyl chloride (346 mg, 1.5 mmol), (K. H. Henegar et al. J. Org. Chem., 1997, 62, 6588–6597) and the solution heated at reflux for 1 hour. The cooled mixture was filtered and the filtrate concentrated under reduced pressure. The residue was purified on silica gel eluting with methanol to give the title compound (180 mg) as a white solid.

m.p. 168–175° C.

m/e 551

EXAMPLE 4

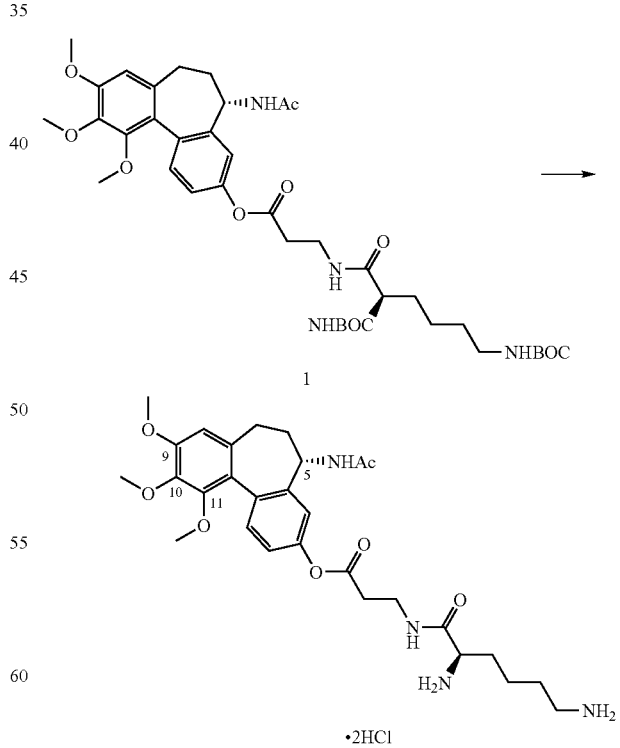

A solution of (5S)-5-(acetylamino)-9,10,11-trimethoxy-6,7-dihydro-5H-dibenzo[a,c]cyclohepten-3-yl 3-{[(2R)-2,6-di(tertbutoxycarbonylamino)hexanoyl]amino}propanoate (1)

(0.123 g; 0.162 mmol) in dichloromethane (10 ml) was treated with a 4.8M solution of hydrogen chloride in ether (170 μl; 0.81 mmol). The mixture was stirred at ambient temperature for 1 hour and the resulting precipitate was filtered, washed with ether and dried to give (5S)-5-(acetylamino)-9,10,11-trimethoxy-6,7-dihydro-5H-dibenzo[a,c]cyclohepten-3-yl 3-{[(2R)-2,6-diaminohexanoyl]amino}propanoate as a white solid.

Yield: 84%

$^1$H NMR spectrum (DMSOd$_6$): 1.39 (m, 2H); 1.58 (m, 2H); 1.74 (m, 2H); 1.89 (s, 3H); 1.89 (m, 1H); 2.02 (m, 1H); 2.15 (m, 1H); 2.5 (m, 1H, signal obscured partially by DMSO peak); 2.74 (m, 2H); 2.84 (t, 2H); 3.52 (m, 5H); 3.78 (s, 3H); 3.78 (m, 1H); 3.84 (s, 3H); 4.55 (m, 1H); 6.80 (s, 1H); 7.1–7.15 (m, 2H); 7.35 (dd, 1H); 8.01 (br s, 2H); 8.32 (m, 2H); 8.53 (d, 1H); 8.96 (t, 1H).

MS-ESI: 557 [MH]$^+$

| Elemental analysis: | Found | C 53.8 | H 6.8 | N 8.7 |
| C$_{29}$H$_{40}$N$_4$O$_7$; 0.8 H$_2$O, 2 HCl | Requires | C 53.9 | H 7.2 | N 8.1% |

The starting material was prepared as follows:

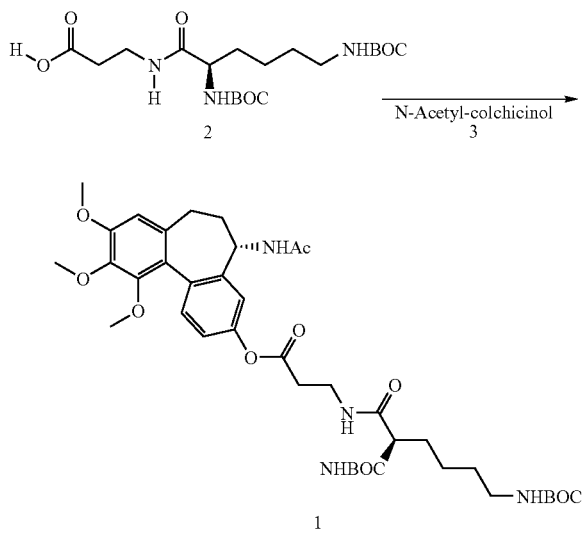

A mixture of 3-{[(2R)-2,6-di(tertbutoxycarbonylamino)hexanoyl]amino}propanoic acid (2) (0.178 g; 0.5 mmol), DCCI (0.124 g; 0.6 mmol), DMAP (0.013 g; 0.1 mmol) and N-acetyl-colchicinol (0.25 g; 1.2 mmol) in dichloromethane was stirred under argon atmosphere at ambient temperature for 5 hours. After filtration of the insoluble material the residue was purified by flash chromatography eluting with dichloromethane/ethanol (95/5) to give (1).

Yield: 32%

$^1$H NMR spectrum (DMSOd$_6$): 1.15–1.6 (m, 6H); 1.36 (s, 18H); 1.87 (s, 3H); 1.87 (m, 1H); 2.05 (m, 1H); 2.15 (m, 1H); 2.50 (m, 1H, signal obscured partially by DMSO peak); 2.75 (t, 2H); 2.86 (m, 2H); 3.85 (m, 2H); 3.51 (s, 3H); 3.78 (s, 3H); 3.84 (s, 3H); 3.85 (m, 1H); 4.55 (m, 1H); 3.7–3.8 (m, 2H); 6.8 (s, 1H); 7.08 (s, 1H); 7.1 (m, 1H); 7.32 (dd, 1H); 8.01 (t, 1H); 8.35 (d, 1H).

EXAMPLE 5

A solution of (5S)-5-(acetylamino)-9,10,11-trimethoxy-6,7-dihydro-5H-dibenzo[a,c]cyclohepten-3-yl 3-[(2-tertbutoxycarbonylaminoacetyl)amino]propanoate (4) (0.36 g; 0.61 mmol) in dichloromethane (5 ml) was treated with a 4.8M solution of hydrogen chloride in ether (1 ml). The mixture was stirred at ambient temperature for 1 hour. After dilution with ether, the resulting precipitate was filtered, washed with ether and dried to give (5S)-5-(acetylamino)-9,10,11-trimethoxy-6,7-dihydro-5H-dibenzo[a,c]cyclohepten-3-yl 3-[(2-aminoacetyl)amino]propanoate.

Yield: 98%

$^1$H NMR spectrum (DMSOd$_6$): 1.90 (m, 1H); 1.90 (s, 3H); 2.05 (m, 1H); 2.3 (m, 1H); 2.9 (m, 1H, signal obscured partially by DMSO peak); 2.84 (t, 2H); 3.52 (s, 3H); 3.52 (m, 2H); 3.6 (m, 2H, signal obscured partially by H$_2$O peak); 3.8 (s, 3H); 3.86 (s, 3H); 4.55 (m, 1H); 6.82 (s, 1H); 7.13 (m, 2H); 7.37 (dd, 1H); 8.1 (br s, 2H); 8.46 (d, 1H); 8.67 (t, 1H).

MS-ESI: 486 [MH]$^+$

| Elemental analysis: | Found | C 54.8 | H 6.2 | N 7.7 |
| C$_{25}$H$_{31}$N$_3$O$_7$; 0.8 H$_2$O, 1.3 HCl | Requires | C 54.8 | H 6.3 | N 7.6% |

The starting material was prepared as follows:

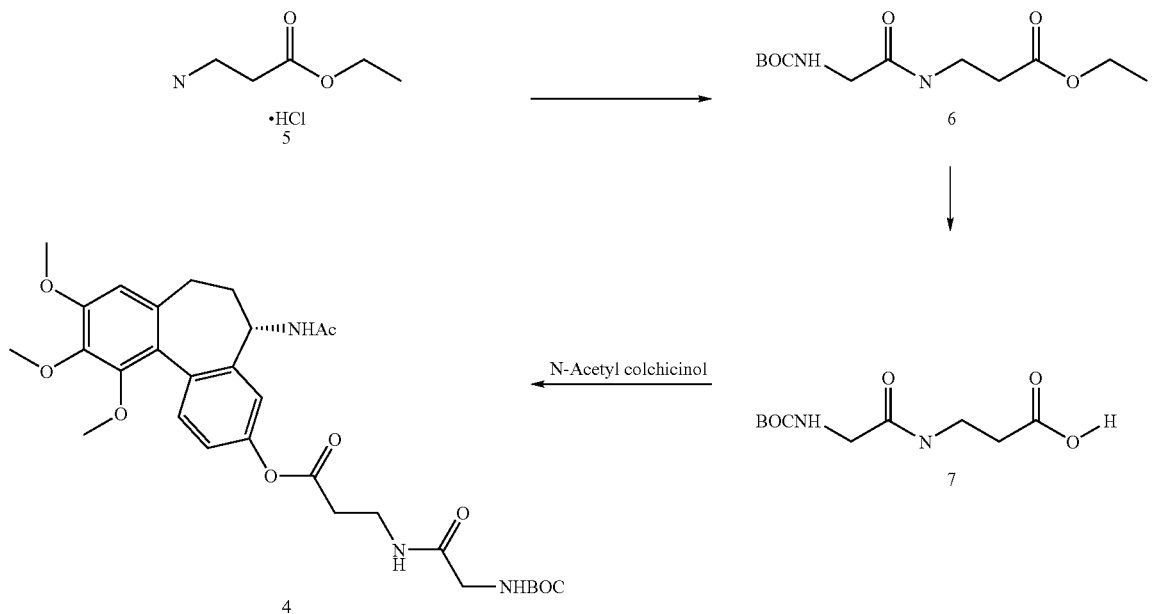

A solution of β-alanine ethyl ester hydrochloride salt (5) (3.07 g; 0.02 mmol), N-(tertbutoxycarbonyl)glycine (3.5 g; 0.02 mmol), DCCI (4.12 g; 0.02 mmol) and 4-methylmorpholine (2.2 ml) in dichloromethane (60 ml) was stirred overnight under argon atmosphere at ambient temperature. After filtration the residue was purified by flash chromatography eluting with dichloromethane/ethanol (96/4) to give ethyl 3-[(2-tertbutoxycarbonylaminoacetyl)amino]propanoate (6).

Yield: 62%

$^1$H NMR spectrum (CDCl$_3$): 1.27 (t, 3H); 1.45 (s, 9H); 3.55 (m, 2H); 3.77 (d, 2H); 4.15 (q, 2H); 5.3 (br s, 2H); 6.56 (br s, 2H).

A solution of (6) at 0° C. (3.43 g; 0.012 mmol) in methanol (40 ml) was treated with 2N sodium hydroxide (6.9 ml; 0.013 mmol). The mixture was stirred at ambient temperature for 90 minutes. After evaporation of the methanol and removal of the insoluble material by filtration, the solution was adjusted to pH5 with 6N hydrochloric acid. The mixture was extracted with dichloromethane and the organic layer evaporated to dryness to give 3-[(2-tertbutoxycarbonylaminoacetyl)amino]propanoic acid (7).

Yield: 16%

$^1$H NMR spectrum (CDCl$_3$+CD$_3$CO$_2$D): 1.44 (s, 9H); 2.61 (t, 2H); 3.5 (m, 2H); 3.80 (m, 2H).

A mixture of N-acetyl-colchicinol (0.357 g; 1 mmol), DCCI (0.248 g; 1.2 mmol), DMAP (0.025 g; 0.2 mmol) and (7) (0.246 g; 1 mmol) in dichloromethane (7 ml) was stirred under argon atmosphere for 5 hours. After removal of the insoluble material by filtration the residue was purified by flash chromatography eluting with dichloromethane/ethanol (92/8) to give (4) as a foam.

Yield: 61%

$^1$H NMR spectrum (DMSOd$_6$): 1.4 (s, 9H); 1.89 (s, 3H); 1.89 (m, 1H); 2.07 (m, 1H); 2.18 (m, 1H); 2.5 (m, 1H, signal obscured partially by DMSO peak); 2.77 (t, 2H); 3.45 (m, 2H); 3.52 (s, 3H); 3.5 (m, 2H); 3.8 (s, 3H); 3.85 (s, 3H); 4.55 (m, 1H); 6.81 (s, 1H); 6.97 (t, 1H); 7.11 (m, 2H); 7.35 (dd, 1H); 8.01 (t, 1H); 8.38 (d, 1H).

EXAMPLE 6

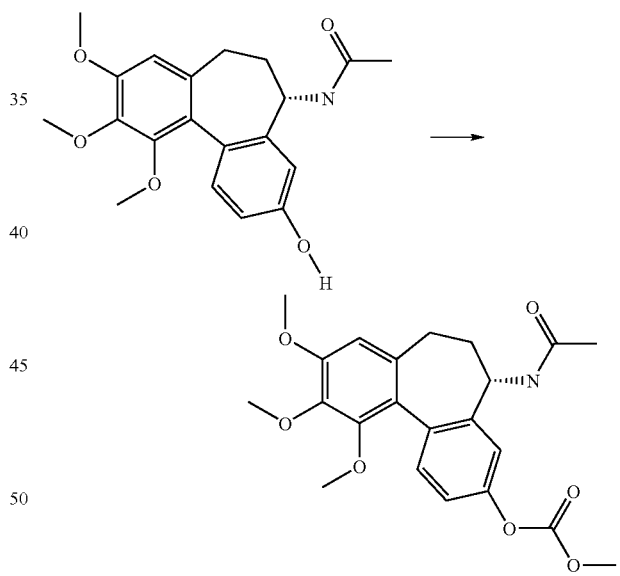

Triethylamine (70 μl; 0.5 mmol) and methyl chloroformate (39 μl; 0.5 mmol) were added to a solution of N-acetyl-colchicinol (0.178 g; 0.5 mmol) in THF (3 ml). The mixture was stirred at ambient temperature for 90 minutes. After removal of the insoluble material by filtration the residue was purified by flash chromatography eluting with dichloromethane/ethanol (98/2) to give (5S)-5-(acetylamino)-9,10,11-trimethoxy-6,7-dihydro-5H-dibenzo[a,c]cyclohepten-3-yl methyl carbonate.

Yield: 75%

$^1$H NMR spectrum (DMSOd$_6$): 1.87 (s, 3H); 1.87 (m, 1H); 2.05 (m, 1H); 2.17 (m, 1H); 2.5 (m, 1H, signal obscured partially by DMSO peak); 3.52 (s, 3H); 3.78 (s, 3H); 3.84 (s, 3H); 3.85 (s, 3H); 4.52 (m, 1H); 6.8 (s, 1H); 7.16–7.18 (m, 2H); 7.36 (dd, 1H); 8.38 (d, 1H).

MS-ESI: 438 [MH]+

| Elemental analysis: | Found | C 61.7 | H 6.2 | N 3.3 |
| --- | --- | --- | --- | --- |
| C22H25NO7; 0.7 H2O | Requires | C 61.6 | H 6.2 | N 3.4% |

EXAMPLE 7

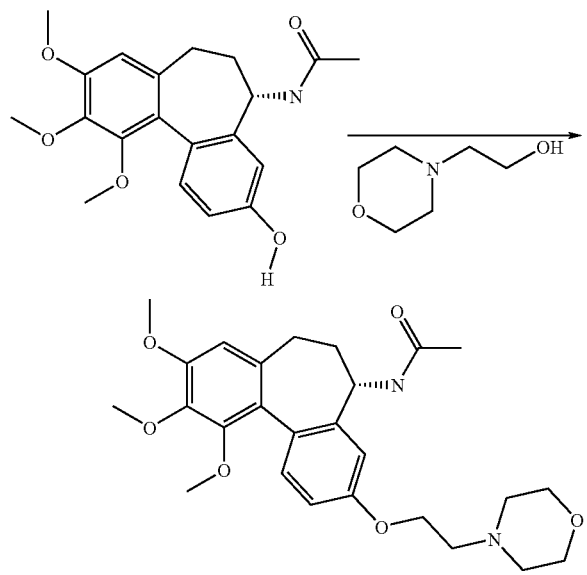

DEAD (0.118 g; 0.75 mmol), triphenylphosphine (0.196 g; 0.75 mmol) and 4-(2-hydroxyethyl)morpholine (61 µl; 0.5 mmol) were added to a solution of N-acetyl-colchicinol (0.178 g; 0.5 mmol) in dichloromethane (5 ml) under argon atmosphere. The mixture was stirred at ambient temperature for 6 hours. After evaporation the residue was purified by flash chromatography eluting with a gradient of 2–10% ethanol/dichloromethane to give N-[(5S)-3-(2-morpholinoethoxy)-9,10,11-trimethoxy-6,7-dihydro-5H-dibenzo[a,c]cyclohepten-5-yl]acetamide.

Yield: 37%

$^1$H NMR spectrum (DMSOd$_6$): 1.85 (m, 1H); 1.87 (s, 3H); 2.05 (m, 1H); 2.15 (m, 1H); 2.39 (m, 2H); 2.5 (m, 3H, signal obscured partially by DMSO peak); 2.72 (t, 2H); 3.46 (s, 3H); 3.54–3.6 (s, 4H); 3.77 (s, 3H); 3.82 (s, 3H); 4.09–4.12 (m, 2H); 4.55 (m, 1H); 6.76 (s, 1H); 6.86–6.90 (m, 2H); 7.23 (dd, 2H); 8.35 (d, 1H).

MS-ESI: 471 [MH]+

| Elemental analysis: | Found | C 66.4 | H 7.3 | N 6.0 |
| --- | --- | --- | --- | --- |
| C26H34N2O6 | Requires | C 66.6 | H 7.3 | N 6.3% |

EXAMPLE 8

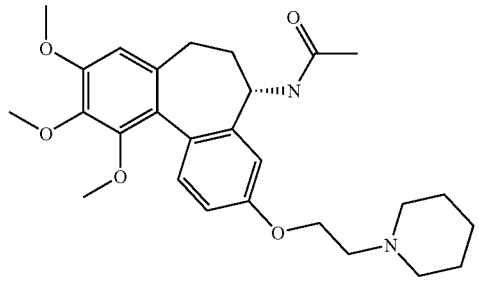

Using an analogous procedure to that described for Example 7, N-acetyl-colchicinol was reacted with 4-(2-hydroxyethyl)piperidine to give N-[(5S)-3-(2-piperidinoethoxy)-9,10,11-trimethoxy-6,7-dihydro-5H-dibenzo[a,c]cyclohepten-5-yl]acetamide.

Yield: 20%

$^1$H NMR spectrum (DMSOd$_6$): 1.39 (m, 2H); 1.49 (m, 4H); 1.80 (m, 1H); 1.88 (s, 3H); 2.05 (m, 1H); 2.15 (m, 1H); 2.45 (m, 4H); 2.5 (m, 1H, signal obscured partially by DMSO peak); 2.67 (m, 2H); 3.46 (s, 3H); 3.77 (s, 3H); 3.82 (s, 3H); 4.08 (t, 2H); 4.55 (m, 1H); 6.76 (s, 1H); 6.86–6.9 (m, 2H); 7.22 (dd, 1H); 8.35 (d, 1H).

MS-ESI: 469 [MH]+

| Elemental analysis: | Found | C 68.7 | H 7.8 | N 5.9 |
| --- | --- | --- | --- | --- |
| C27H36N2O5; 0.2 H2O | Requires | C 68.5 | H 8.0 | N 6.1% |

EXAMPLE 9

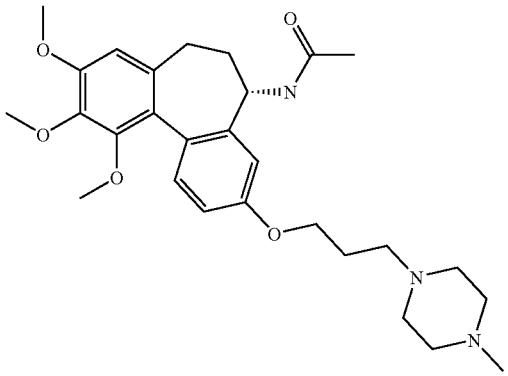

Using an analogous procedure to that described for Example 7, N-acetyl-colchicinol was reacted with 4-(3-hydroxypropyl)-1-methylpiperazine to give N-[(5S)-3-(3-(4-methylpiperazin-1-yl)propoxy)-9,10,11-trimethoxy-6,7-dihydro-5H-dibenzo[a,c]cyclohepten-5-yl]acetamide.

Yield: 22%

$^1$H NMR spectrum (DMSO d$_6$): 1.88 (s, 3H); 1.85–1.9 (m, 3H); 2.04–2.16 (m, 5H); 2.32–2.53 (m, 11H, signals obscured partially by DMSO peak); 3.47 (s, 3H); 3.78 (s, 3H); 3.83 (s, 3H); 4.03 (t, 2H); 4.55 (m, 1H); 6.72 (s, 1H); 6.85 (dd, 1H); 6.9 (m, 1H); 7.23 (d, 1H); 8.23 (d, 1H).

MS-ESI: 498 [MH]+

| Elemental analysis: | Found | C 64.8 | H 8.0 | N 8.1 |
| $C_{28}H_{39}N_3O_5$; 0.8 $H_2O$ | Requires | C 64.7 | H 7.7 | N 8.2% |

0.1 dichloromethane

EXAMPLE 10

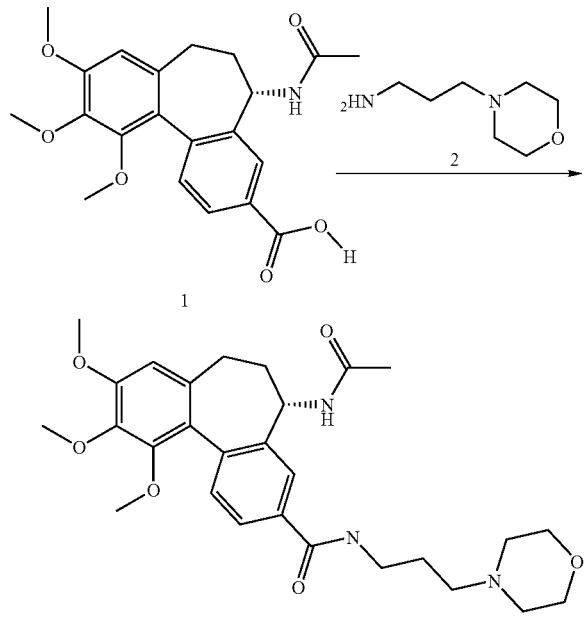

A solution of N-[(5S)-3-carboxy-9,10,11-trimethoxy-6,7-dihydro-5H-dibenzo[a,c]cyclohepten-5-yl]acetamide (0.3 g; 0.779 mmol), (Med. Chem. Res. 1991, 142), DCCI (0.322 g; 1.55 mmol), DMAP (0.069 g; 0.389 mmol) and 4-(3-aminopropyl)morpholine (170 µl; 1.17 mmol) in dichloromethane (6 ml) was stirred under argon atmosphere overnight. After removal of the insoluble material by filtration, the residue was purified on reverse phase silica eluting with a gradient of 40–50% methanol/ammonium carbonate buffer (2 g/l, pH7). The appropriate fractions were evaporated to dryness and triturated in ether to give (5S)-5-(acetylamino)-9,10,11-trimethoxy-N-(3-morpholinopropyl)-6,7-dihydro-5H-dibenzo[a,c]cycloheptene-3-carboxamide as a white solid.

Yield: 30%

$^1$H NMR spectrum (DMSOd$_6$): 1.7 (m, 2H); 1.91 (s, 3H); 1.91 (m, 1H); 2.05 (m, 1H); 2.2 (m, 1H); 2.37 (m, 6H); 2.5 (m, 3H, signal obscured partially by DMSO peak); 3.51 (s, 3H); 3.58 (m, 4H); 3.8 (s, 3H); 3.86 (s, 3H); 4.58 (m, 1H); 6.83 (s, 1H); 7.39 (dd, 1H); 7.74 (m, 1H); 7.84 (s, 1H); 8.51 (m, 2H).

MS-ESI: 512 [MH]$^+$

| Elemental analysis: | Found | C 64.8 | H 7.3 | N 8.1 |
| $C_{28}H_{37}N_3O_6$; 0.4 $H_2O$ | Requires | C 64.5 | H 7.3 | N 8.0% |

EXAMPLE 11

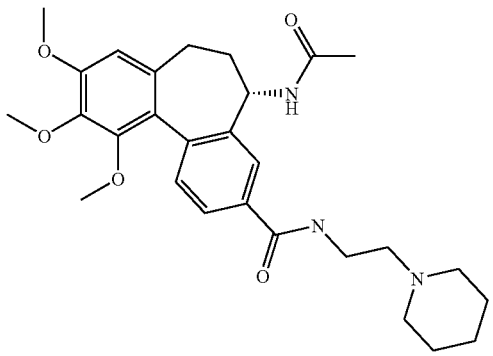

Using an analogous procedure to that described for Example 10, N-[(5S)-3-carboxy-9,10,11-trimethoxy-6,7-dihydro-5H-dibenzo[a,c]cyclohepten-5-yl]acetamide was reacted with 1-(2-aminoethyl)piperidine to give (5S)-5-(acetylamino)-9,10,11-trimethoxy-N-(2-piperidinoethyl)-6,7-dihydro-5H-dibenzo[a,c]cycloheptene-3-carboxamide.

Yield: 43%

$^1$H NMR spectrum (DMSOd$_6$): 1.38 (m, 2H); 1.49 (m, 4H); 1.89 (s, 3H); 1.89 (m, 1H); 2.05 (m, 1H); 2.18 (, 1H); 2.4–2.5 (m, 4H); 2.5 (m, 1H, signal obscured partially by DMSO peak); 3.38 (m, 4H); 3.49 (s, 3H); 3.79 (s, 3H); 3.84 (s, 3H); 4.58 (m, 1H); 6.81 (s, 1H); 7.37 (d, 1H); 7.71 (m, 1H); 7.81 (s, 1H); 8.35 (t, 1H); 8.49 (d, 1H).

MS-ESI: 496 [MH]$^+$

| Elemental analysis: | Found | C 66.4 | H 7.6 | N 8.3 |
| $C_{28}H_{37}N_3O_5$; 0.6 $H_2O$ | Requires | C 66.1 | H 7.7 | N 8.3% |

EXAMPLE 12

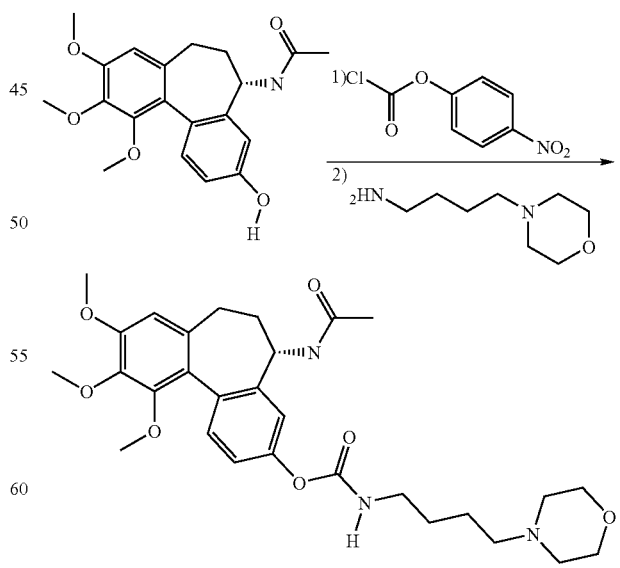

A solution of N-acetyl-colchicinol (0.357 g; 1 mmol), 4-nitrophenyl chloroformate (0.262 g; 1.3 mmol) and triethylamine (182 µl; 1.3 mmol) in dichloromethane (10 ml)

was stirred, under argon atmosphere, at ambient temperature for 90 minutes. 4-(4-Aminobutyl)morpholine (0.237 g; 1.5 mmol) was then added and the mixture was further stirred for 4 hours. After evaporation to dryness the residue was purified by flash chromatography eluting with a gradient of 0–12% ethanol/dichloromethane to give (5S)-5-(acetylamino)-9,10,11-trimethoxy-6,7-dihydro-5H-dibenzo[a,c]cyclohepten-3-yl N-(4-morpholinobutyl)carbamate as a white foam.

Yield: 24%

$^1$H NMR spectrum (DMSOd$_6$): 1.49 (m, 4H); 1.86 (s, 3H); 1.86 (m, 1H); 2.05 (m, 1H); 2.18 (m, 1H); 2.26–2.34 (m, 6H); 2.5 (m, 1H, signal obscured partially by DMSO peak); 3.08 (m, 2H); 3.51 (s, 3H); 3.57 (m, 4H); 3.78 (s, 3H); 3.84 (s, 3H); 4.55 (m, 1H); 6.79 (s, 1H); 7.02 (m, 2H); 7.29 (d, 1H); 7.78 (t, 1H); 8.39 (d, 1H).

MS-ESI: 542 [MH]$^+$

| Elemental analysis: | Found | C 63.5 | H 7.3 | N 7.7 |
|---|---|---|---|---|
| $C_{29}H_{39}N_3O_7$; 0.4 $H_2O$ | Requires | C 63.4 | H 7.3 | N 7.7% |

EXAMPLE 13

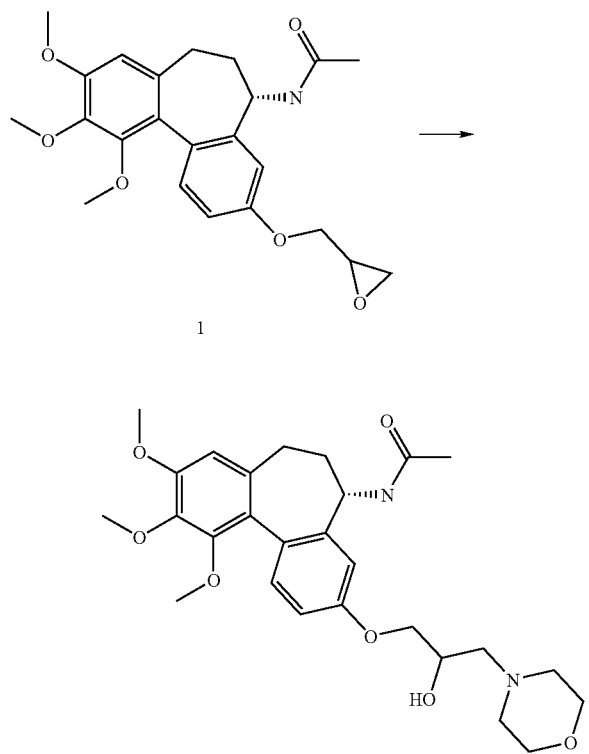

A solution of N-[(5S)-3-(2,3-epoxypropoxy)-9,10,11-trimethoxy-6,7-dihydro-5H-dibenzo[a,c]cyclohepten-5-yl]acetamide (1) (0.092 g; 0.22 mmol) and morpholine (40 µl; 0.44 mmol) in methanol was heated at reflux for 4 hours. After evaporation to dryness the residue was purified by flash chromatography eluting with dichloromethane/ethanol (90/10) to give N-[(5S)-3-(2-hydroxy-3-morpholinopropoxy)-9,10,11-trimethoxy-6,7-dihydro-5H-dibenzo[a,c]cyclohepten-5-yl]acetamide as a yellow foam.

Yield: 55%

$^1$H NMR spectrum (DMSOd$_6$): 1.88 (s, 3H); 1.88 (m, 1H); 2.05 (m, 1H); 2.15 (m, 1H); 2.42–2.5 (m, 4H); 2.5 (m, 1H, signal obscured partially by DMSO peak); 3.33–3.4 (m, 4H); 3.46 (s, 3H); 3.57 (m, 2H); 3.77 (s, 3H); 3.82 (s, 3H); 3.90 (m, 1H); 3.99 (m, 2H); 4.52 (m, 1H); 4.9 (t, 1H); 6.76 (s, 1H); 6.86–6.9 (m, 2H); 7.23 (d, 1H); 8.37 (d, 1H).

MS-ESI: 501 [MH]$^+$

| Elemental analysis: | Found | C 64.8 | H 7.3 | N 5.6 |
|---|---|---|---|---|
| $C_{27}H_{36}N_2O_7$ | Requires | C 64.5 | H 7.5 | N 5.5% |

The starting material was prepared as follows:

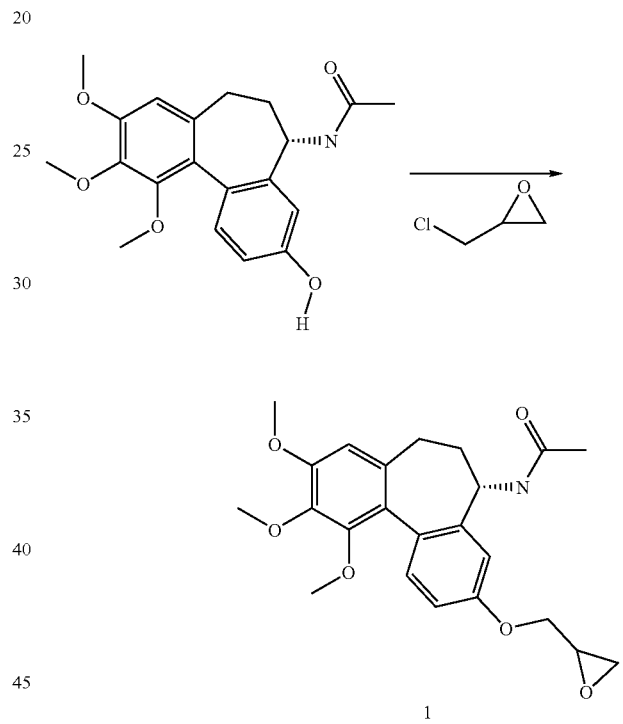

A solution of N-acetyl-colchicinol (0.179 g; 0.5 mmol), potassium carbonate (0.083 g; 0.6 mmol) and epichlorohydrin (0.059 g; 0.75 mmol) in DMF (2 ml) was heated at 80° C. for 5 hours. The mixture was poured into saturated sodium hydrogen carbonate and extracted with ethyl acetate. The organic phase was washed with brine, dried (MgSO$_4$) and evaporated to give an oil which was purified by flash chromatography eluting with a 2–4% gradient of ethanol/dichloromethane to give (1).

Yield: 46%

$^1$H NMR spectrum (DMSOd$_6$): 1.88 (s, 3H); 1.84 'm, 1H); 2.05 (m, 1H); 2.15 (m, 1H); 2.5 (m, 1H partially obscured by DMSO peak); 2.75 (m, 1H); 2.88 (m, 1H); 3.42 (m, 1H); 3.46 (s, 3H); 3.77 (s, 3H); 3.82 (s, 3H); 3.87 (m, 1H); 4.35 (m, 1H); 4.52 (m, 1H); 6.76 (s, 1H); 6.88–6.94 (m, 2H); 7.24 (d, 1H); 8.35 (d, 1H).

EXAMPLE 14

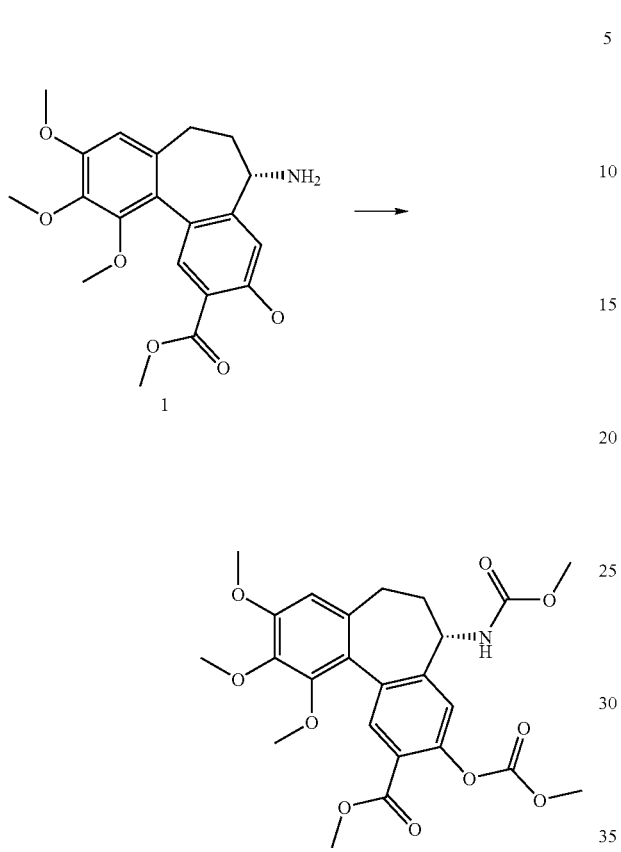

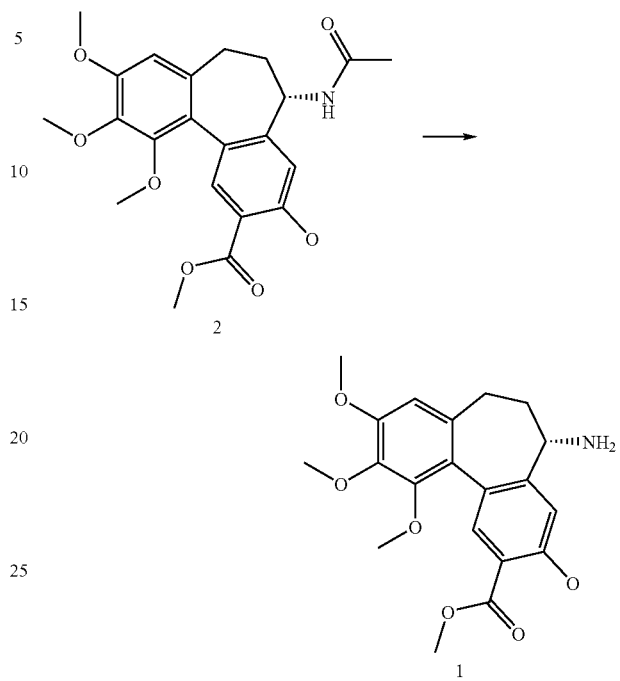

A solution of methyl (5S)-9,10,11-trimethoxy-5-amino-3-hydroxy-6,7-dihydro-5H-dibenzo[a,c]cyclohepten-2-carboxylate (1) (0.373 g; 1 mmol) methyl chloroformate (0.17 ml; 2.2 mmol) and triethylamine was stirred at ambient temperature overnight. After evaporation to dryness, the residue was purified by flash chromatography, eluting with ethanol/dichloromethane (2/98) and further purified by preparative HPLC on reverse phase silica eluting with methanol/ammonium carbonate buffer (2 g/l pH7) (50/50) to give methyl (5S)-9,10,11-trimethoxy-5-[(methoxycarbonyl)amino]-3-[(methoxycarbonyl)oxy]-6,7-dihydro-5H-dibenzo[a,c]cycloheptene-2-carboxylate.

Yield: 48%

$^1$H NMR spectrum (DMSOd$_6$): 1.84–2.09 (m, 2H); 2.19–2.31 (m, 1H); 2.57 (m, 1H, partially obscured by DMSO peak); 3.50 (s, 3H); 3.55 (s, 3H); 3.81 (s, 3H); 3.82 (s, 3H); 3.86 (s, 3H); 3.87 (s, 3H); 4.28–4.389 (m, 1H); 6.85 (s, 1H); 7.24 (s, 1H); 7.88–7.97 (m, 1H); 7.91 (s, 1H).

MS-ESI: 512 [MNa]$^+$

| Elemental analysis: | Found | C 58.7 | H 5.7 | N 3.0 |
| $C_{24}H_{27}NO_{10}$ | Requires | C 58.9 | H 5.6 | N 2.9% |

The starting material was prepared as follows:

A solution of methyl (5S)-9,10,11-trimethoxy-5-acetylamino-3-hydroxy-6,7-dihydro-5H-dibenzo[a,c]cycloheptene-2-carboxylate (2) (Collect. Czech. Chem. Communi. 64, 217 (1999)) in a mixture of 6N hydrochloric acid and methanol (30/70) was heated at reflux for 8 hours. The mixture was adjusted to pH8 by addition of sodium carbonate. Extraction with dichloromethane and purification by flash chromatography (elution with dichloromethane/methanol (94/6)) gave (1) as a foam.

$^1$H NMR spectrum (DMSOd$_6$): 1.61 (m, 1H); 2.04 (m, 1H); 2.28 (m, 1H); 2.45 (m, 1H); 3.50 (s, 3H); 3.54 (m, 1H); 3.77 (s, 3H); 3.83 (s, 3H); 3.90 (s, 3H); 6.77 (s, 1H); 7.30 (s, 1H); 7.73 (s, 1H); 1.57 (br s, 1H).

EXAMPLE 15

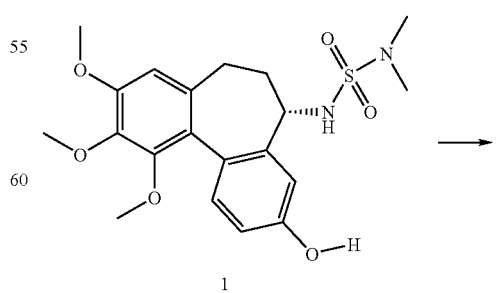

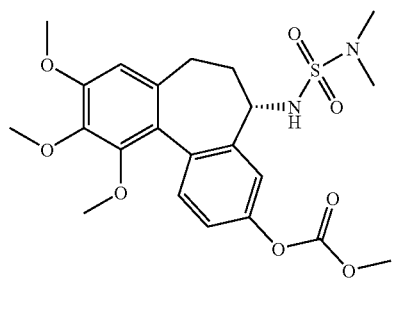

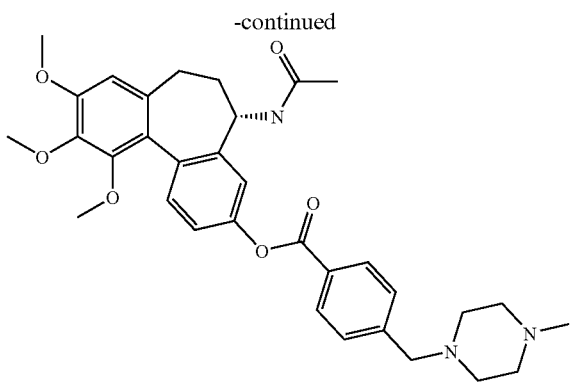

A solution of (5S)-5-{[(dimethylamino)sulphonyl]amino}-9,10,11-trimethoxy-6,7-dihydro-5H-dibenzo[a,c]cyclohepten-3-ol (1) (0.9; 0.71 mmol), methyl chloroformate (0.061 ml; 0.782 mmol) and triethylamine (0.109 ml; 0.782 mmol) in acetonitrile (8 ml) was stirred under argon atmosphere at 40° C. for 4 hours. After evaporation to dryness, the residue was purified by flash chromatography eluting with ethanol/dichloromethane (2/98) to give (5S)-5-{[(dimethylamino)sulphonyl]amino}-9,10,11-trimethoxy-6,7-dihydro-5H-dibenzo[a,c]cyclohepten-3-yl methyl carbonate.

Yield: 32%

$^1$H NMR spectrum (DMSOd$_6$): 1.93–2.03 (m, 2H); 2.12–2.17 (m, 1H); 2.46 (s, 6H); 2.45–2.55 (m, 1H); 3.46 (s, 3H); 3.79 (s, 3H); 3.85 (s, 3H); 3.87 (s, 3H); 3.94–4.10 (m, 1H); 6.82 (s, 1H); 7.21 (d, 1H); 7.37 (d, 1H); 7.43 (s, 1H); 7.93 (br s, 1H).

MS-ESI: 503 [MNa]$^+$

| Elemental analysis | Found | C 55.2 | H 6.1 | N 5.8 | S 6.3 |
|---|---|---|---|---|---|
| C$_{22}$H$_{28}$N$_2$O$_8$S | Requires | C 55.0 | H 5.9 | N 5.8 | S 6.7% |

EXAMPLE 16

A solution of N-[(5S)-3-(4-chloromethylphenylcarbonyloxy)-9,10,11-trimethoxy-6,7-dihydro-5H-dibenzo[a,c]cyclohepten-5-yl]acetamide (1) (0.308 g; 0.604 mmol), 1-methylpiperazine (0.088 ml; 0.785 mmol) and sodium iodide (0.02 g; 0.121 mmol) in acetonitrile (10 ml) was stirred under argon atmosphere overnight. After evaporation to dryness, the residue was purified by flash chromatography eluting with a 5–12% gradient of methanol/dichloromethane. After evaporation of the appropriate fractions, the solid was triturated in ether/pentane to give N-[(5S)-3-(4-{4-methylpiperazin-1-ylmethyl}phenylcarbonyloxy)-9,10,11-trimethoxy-6,7-dihydro-5H-dibenzo[a,c]cyclohepten-5-yl]acetamide as a solid.

Yield: 75%

$^1$H NMR spectrum (DMSOd$_6$): 1.86 (s, 3H); 1.83–1.98 (m, 1H); 2.00–2.26 (m, 2H); 2.31 (br s, 3H); 2.4–2.6 (m, 8H); 2.53–2.59 (m, 1H); 3.54 (s, 3H); 3.62 (s, 2H); 3.80 (s, 3H); 3.85 (s, 3H); 4.53–4.64 (m, 1H); 6.82 (s, 1H); 7.20–7.25 (m, 2H); 7.41 (d, 1H); 7.56 (d, 2H); 8.13 (d, 2H); 8.39 (d, 1H).

MS-ESI: 574 [MH]$^+$

The starting material was prepared as follows

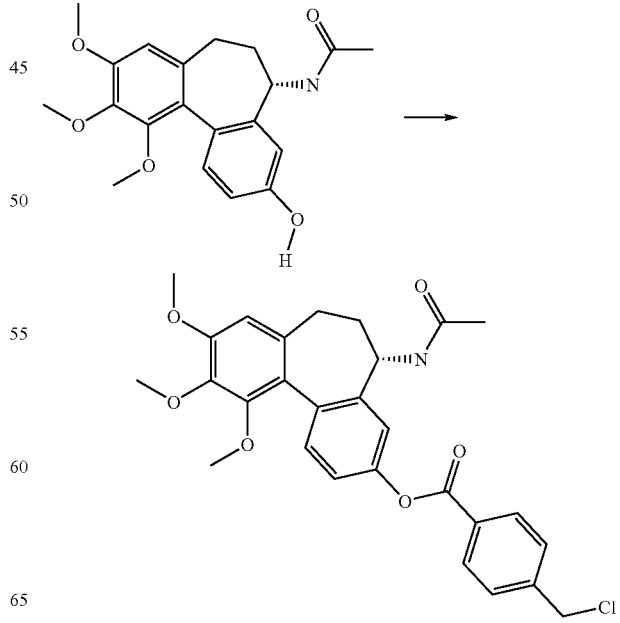

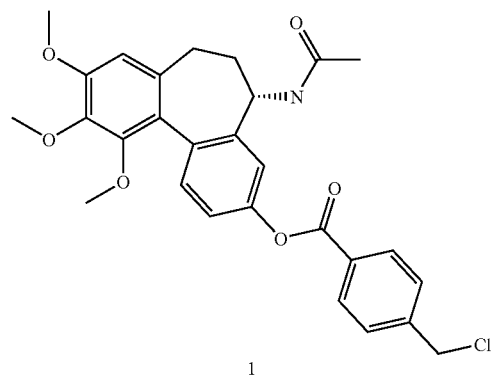

A solution of N-acetyl-colchicinol (0.357 g; 1 mmol), EDCI (0.23 g; 1.2 mmol), DMAP (0.025 g; 0.2 mmol) and 4-chloromethylbenzoic acid (0.205 g; 1.2 mmol) in dichloromethane (8 ml) was stirred under argon atmosphere overnight. After evaporation to dryness, the residue was purified by flash chromatography eluting with dichloromethane/ethanol (98/2) to give (1).

Yield: 72%

$^1$H NMR spectrum (DMSOd$_6$): 1.86 (s, 3H); 1.91 (m, 1H); 1.04–2.14 (m, 1H); 2.14–2.67 (m, 1H); 2.57 (m, 1H; partially obscured by DMSO peak); 3.54 (s, 3H); 3.80 (s, 3H); 3.86 (s, 3H); 4.54–4.64 (m, 1H); 4.91 (s, 2H); 6.83 (s, 1H); 7.21–7.28 (m, 2H); 7.42 (d, 1H); 7.70 (d, 2H); 8.14 (d, 2H); 8.40 (d, 1H).

EXAMPLE 17

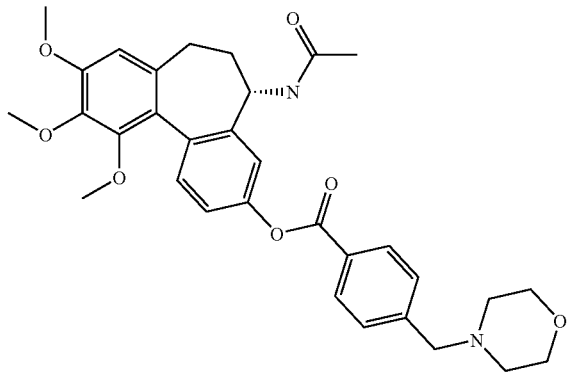

Using an analogous procedure to that described for Example 16, N-[(5S)-3-(4-chloromethylphenylcarbonyloxy)-9,10,11-trimethoxy-6,7-dihydro-5H-dibenzo[a,c]cyclohepten-5-yl]acetamide was reacted with morpholine to give N-[(5S)-3-(4-{morpholinomethyl}phenylcarbonyloxy)-9,10,11-trimethoxy-6,7-dihydro-5H-dibenzo[a,c]cyclohepten-5-yl]acetamide.

Yield: 86%

$^1$H NMR spectrum (DMSOd$_6$): 1.90 (s, 3H); 1.88–2.01 (m, 1H); 2.06–2.30 (m, 2H); 2.43 (br s, 4H); 2.54–2.63 (m, 1H); 3.30 (m, 2H); 3.58 (s, 3H); 3.62–3.67 (m, 6H); 3.84 (s, 3H); 3.89 (s, 3H); 4.57–4.67 (m, 1H); 3.86 (s, 1H); 7.23–7.30 (m, 2H); 7.45 (d, 1H); 7.61 (d, 1H); 8.17 (d, 1H); 8.43 (d, 1H).

MS-ESI: 561 [MH]$^+$

| Elemental analysis | Found | C 66.1 | H 6.5 | N 4.9 |
| --- | --- | --- | --- | --- |
| C$_{32}$H$_{36}$N$_2$O$_7$ ; 0.3 dichloromethane | Requires | C 66.2 | H 6.3 | N 4.8% |

EXAMPLE 18

CHIRAL

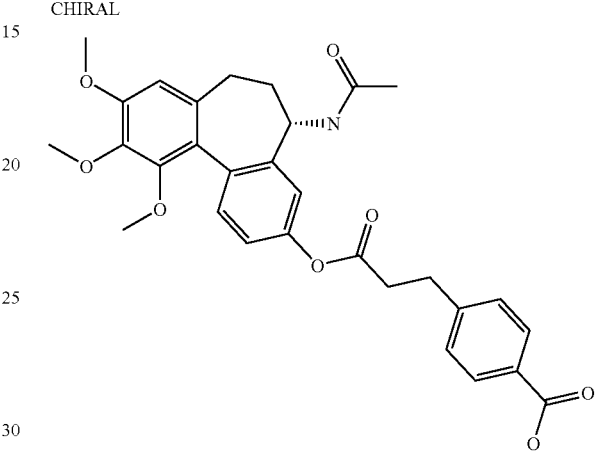

A solution of N-acetyl-colchicinol (0.357 g; 1 mmol), EDCI (0.23 g; 1.2 mmol), DMAP (0.025 g; 0.2 mmol) and 3-(4-carboxyphenyl)propionic acid (0.233 g; 1.2 mmol) was stirred at ambient temperature overnight. After removal of the solvent by evaporation, the residue was purified by preparative HPLC on reverse phase silica eluting with methanol/ammonium carbonate buffer (2 g/l pH7) (50/50) to give 4-(3-[(5S)-5-(acetylamino)-9,10,11-trimethoxy-6,7-dihydro-5H-dibenzo[a,c]cyclohepten-3-yl]oxy-3-oxopropyl) benzoic acid.

Yield: 70%

$^1$H NMR spectrum (DMSOd$_6$): 1.82–1.93 (m, 4H); 1.97–2.22 (m, 2H); 2.39–2.63 (m, 1H); 2.93–2.99 (m, 2H); 2.99–3.06 (m, 2H); 3.51 (s, 3H); 3.78 (s, 3H); 3.84 (s, 3H); 3.47–3.56 (m, 1H); 6.89 (s, 1H); 6.94 (d, 1H); 6.99 (dd, 1H); 7.30–7.37 (m, 3H); 7.85 (d, 2H); 8.46 (d, 1H).

MS-ESI: 534 [MH]$^+$

EXAMPLE 19

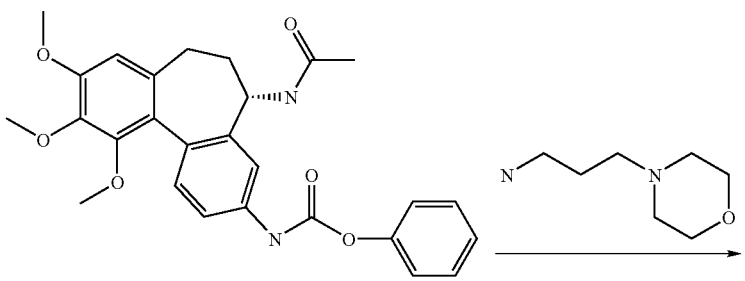

-continued

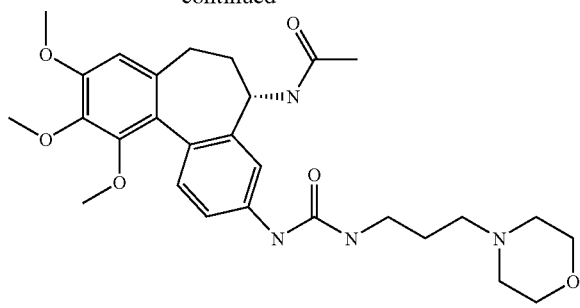

A solution of N-[(5S)-3-phenoxycarbonylamino-9,10,11-trimethoxy-6,7-dihydro-5H-dibenzo[a,c]cyclohepten-5-yl]acetamide (1) (0.1 g; 0.21 mmol) and 4-(3-aminopropyl)morpholine (0.095 g; 0.66 mmol) in DMSO (1 ml) was stirred at ambient temperature for 1 hour. The mixture was purified by preparative HPLC on reverse phase silica eluting with methanol/ammonium carbonate buffer (2 g/l, pH7) (40/60) to give, after evaporation, N-[(5S)-9,10,11-trimethoxy-3-([(3-morpholinopropyl)amino]carbonylamino)-6,7-dihydro-5H-dibenzo[a,c]cyclohepten-5-yl]acetamide as a foam.

Yield: 84%

$^1$H NMR spectrum (DMSOd$_6$): 1.6 (m, 2H); 1.88 (s, 3H); 1.90 (m, 1H); 2.0–2.2 (m, 2H); 2.3–2.4 (m, 6H); 2.45 (m, 1H, signal obscured by DMSO peak); 3.15 (m, 2H); 3.47 (s, 3H); 3.6 (m, 4H); 3.78 (s, 3H); 3.83 (d, 3H); 4.47 (m, 1H); 6.13 (t, 1H); 6.76 (s, 1H); 7.16 (d, 1H); 7.29 (d, 1H); 7.37 (dd, 1H); 8.37 (d, 1H); 8.47 (s, 1H).

MS-ESI: 527 [MH]$^+$

| Elemental analysis: | Found | C 63.4 | H 7.4 | N 10.6 |
|---|---|---|---|---|
| C$_{28}$H$_{38}$N$_4$O$_6$; 0.1 H$_2$O | Requires | C 63.6 | H 7.3 | N 10.6% |

The starting material was prepared as follows:

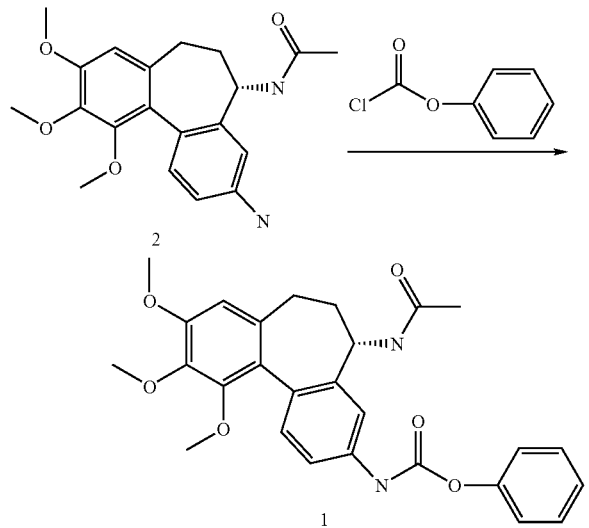

Pyridine (570 µl; 7 mmol) and phenyl chloroformate (720 µl; 10.3 mmol) were added to a solution of N-[(5S)-3-amino-9,10,11-trimethoxy-6,7-dihydro-5H-dibenzo[a,c]cyclohepten-5-yl]acetamide (2) cooled at 0° C. (2 g; 5.6 mmol) in THF (40 ml), under argon atmosphere. The mixture was stirred at 0° C. for 5 minutes and then at ambient temperature for 1 hour. The mixture was extracted with ethyl acetate. The organic phase was washed with 1M hydrochloric acid, saturated sodium hydrogen carbonate and brine. After evaporation to dryness the solid was triturated with ether and hexane to give (1) as a solid.

Yield: 89%

$^1$H NMR spectrum (DMSOd$_6$): 1.82 (s, 3H); 1.85 (m, 1H); 2.10 (m, 2H); 2.5 (m, 1H, signal obscured by DMSO peak); 3.47 (s, 3H); 3.77 (s, 3H); 3.82 (s, 3H); 4.48 (m, 1H); 6.77 (s, 1H); 7.20–7.50 (m, 7H); 7.55 (s, 1H); 8.38 (d, 1H); 9.31 (s, 1H).

EXAMPLE 20

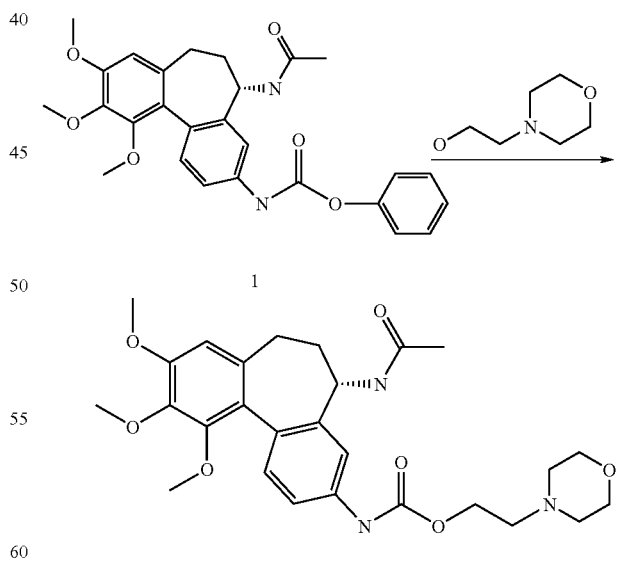

Using an analogous procedure to that described for Example 19, N-[(5S)-3-phenoxycarbonylamino-9,10,11-trimethoxy-6,7-dihydro-5H-dibenzo[a,c]cyclohepten-5-yl]acetamide (1) was reacted with 4-(2-hydroxyethyl)morpholine and the mixture was heated at 60° C. for 2 hours to give N-[(5S)-3-(2-morpholinoethoxycarbonylamino)-9,10,11- trimethoxy-6,7-dihydro-5H-dibenzo[a,c]cyclohepten-5-yl]acetamide.

Yield: 84%

$^1$H NMR spectrum (DMSOd$_6$): 1.89 (s, 3H); 1.90 (m, 1H); 2.0–2.2 (m, 2H); 2.4–2.45 (m, 4H); 2.46 (m, 1H, signal obscured by DMSO peak); 2.6 (t, 2H); 3.42 (s, 3H); 3.59 (m, 4H); 3.78 (s, 3H); 3.84 (s, 3H); 4.22 (m, 2H); 4.44 (m, 1H); 6.78 (s, 1H); 7.22 (d, 1H); 7.39 (dd, 1H); 7.50 (s, 1H); 8.39 (d, 1H); 9.73 (s, 1H).

MS-ESI: 514 [MH]$^+$

| Elemental analysis: | Found | C 60.4 | H 6.6 | N 8.0 |
|---|---|---|---|---|
| C$_{27}$H$_{35}$N$_3$O$_7$; 1.1 H$_2$O | Required | C 60.8 | H 7.0 | N 7.9% |

EXAMPLE 21

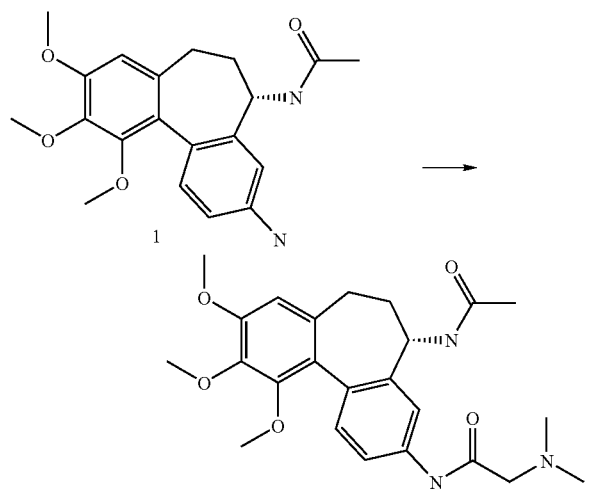

A solution of N-[(5S)-3-amino-9,10,11-trimethoxy-6,7-dihydro-5H-dibenzo[a,c]cyclohepten-5-yl]acetamide (1) (0.2 g; 0.56 mmol), N,N-dimethylglycine (0.058 g; 0.56 mmol), EDCI (0.14 g; 0.73 mmol) and DMAP (0.014 g; 0.11 mmol) in dichloromethane (8 ml) was stirred at ambient temperature overnight. The mixture was washed with water and the organic phase was evaporated and purified by preparative HPLC on reverse phase silica eluting with methanol/ammonium carbonate buffer (2 g/l, pH7) (40/60) to give, after evaporation, N-[(5S)-3-(N,N-dimethylaminoacetylamino)-9,10,11-trimethoxy-6,7-dihydro-5H-dibenzo[a,c]cyclohepten-5-yl]acetamide as a white foam.

Yield: 57%

$^1$H NMR spectrum (DMSOd$_6$): 1.90 (s, 3H); 1.93 (m, 1H); 2.0–2.2 (m, 2H); 2.31 (s, 6H); 2.5 (m, 1H, signal partially obscured by DMSO peak); 3.09 (d, 1H); 3.10 (d,1H); 3.48 (s, 3H); 3.79 (s, 3H); 3.84 (s, 3H); 4.5 (m, 1H); 6.78 (s, 1H); 7.25 (d, 1H); 7.6 (m, 2H); 8.4 (d, 1H); 9.73 (s, 1H).

MS-ESI: 442 [MH]$^+$

| Elemental analysis: | Found | C 63.0 | H 7.0 | N 9.2 |
|---|---|---|---|---|
| C$_{24}$H$_{31}$N$_3$O$_5$; 0.8 H$_2$O | Required | C 63.2 | H 7.2 | N 9.2% |

EXAMPLE 22

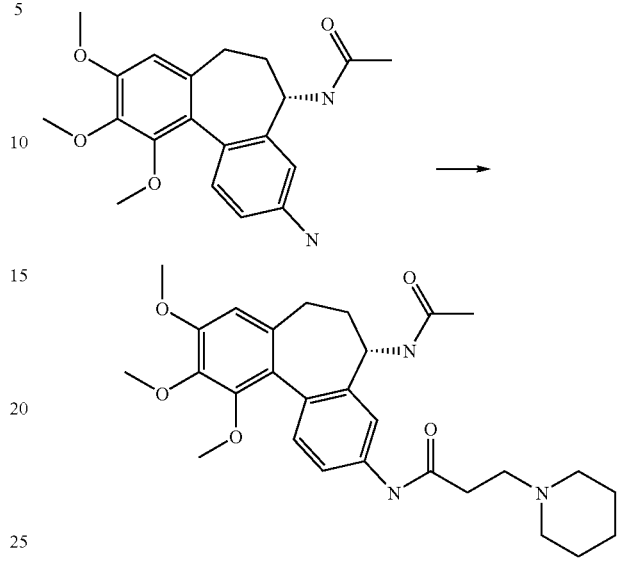

Using an analogous procedure to that described for Example 21, N-[(5S)-3-amino-9,10,11-trimethoxy-6,7-dihydro-5H-dibenzo[a,c]cyclohepten-5-yl]acetamide was reacted with 1-piperidinepropionic acid to give N-[(5S)-3-(3-piperidinopropanoylamino)-9,10,11-trimethoxy-6,7-dihydro-5H-dibenzo[a,c]cyclohepten-5-yl]acetamide.

Yield: 61%

$^1$H NMR spectrum (DMSOd$_6$): 1.40 (m, 2H); 1.55 (m, 4H); 1.89 (s, 3H); 1.90 (m, 1H); 2.0–2.2 (m, 2H); 2.4 (br s, 4H); 2.45 (m, 2H); 2.5 (m, 1H, signal obscured by DMSO peak); 2.62 (m, 2H); 3.47 (s, 3H); 3.79 (s, 3H); 3.84 (s, 3H); 4.45 (m, 1H); 6.78 (s, 1H); 7.24 (d, 1H); 7.5 (s, 1H); 7.58 (dd, 1H); 8.40 (d, 1H).

MS-ESI: 496 [MH]$^+$

| Elemental analysis: | Found | C 65.7 | H 7.4 | N 8.2 |
|---|---|---|---|---|
| C$_{28}$H$_{37}$N$_3$O$_5$ | Required | C 65.7 | H 7.6 | N 8.2% |

EXAMPLE 23

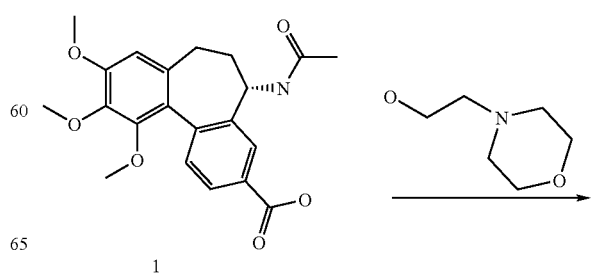

-continued

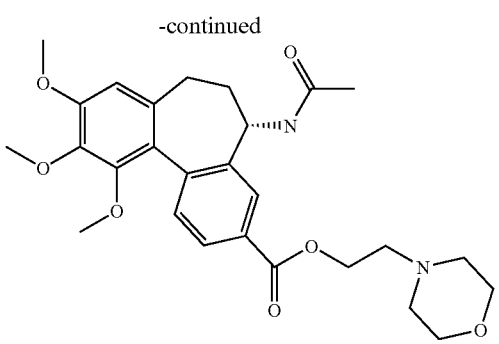

A solution of N-[(5S)-3-carboxy-9,10,11-trimethoxy-6,7-dihydro-5H-dibenzo[a,c]cyclohepten-5-yl]acetamide (1) (0.385 g; 1 mmol), EDCI (0.248 g; 1.3 mmol), DMAP (0.248 g; 0.2 mmol) and 4-(2-hydroxyethyl)morpholine (127 μl; 1.05 mmol) was stirred at ambient temperature overnight. After evaporation to dryness the residue was purified by preparative HPLC on reverse phase silica eluting with a 40–60% gradient of methanol/ammonium carbonate buffer (2 g/l, pH7) to give, after evaporation, N-[(5S)-3-(2-morpholinoethoxycarbonyl)-9,10,11-trimethoxy-6,7-dihydro-5H-dibenzo[a,c]cyclohepten-5-yl]acetamide as a solid.

Yield: 47%

$^1$H NMR spectrum (DMSOd$_6$): 1.88 (s, 3H); 1.88–2.05 (m, 2H); 2.2 (m, 1H); 2.5 (m, 5H, signal obscured by DMSO peak); 2.7 (m, 2H); 3.5 (s, 3H); 3.6 (m, 4H); 3.79 (s, 3H); 3.85 (s, 3H); 4.4 (m, 2H); 4.55 (m, 1H); 6.82 (s, 1H); 7.47 (d, 1H); 7.89 (dd, 1H); 7.95 (d, 1H); 8.58 (d, 1H).

MS-ESI: 499 [MH]$^+$

| Elemental analysis: | Found | C 63.2 | H 6.7 | N 5.5 |
| $C_{27}H_{34}N_2O_7$; 0.6 $H_2O$ | Required | C 65.0 | H 6.9 | N 5.6% |

EXAMPLE 24

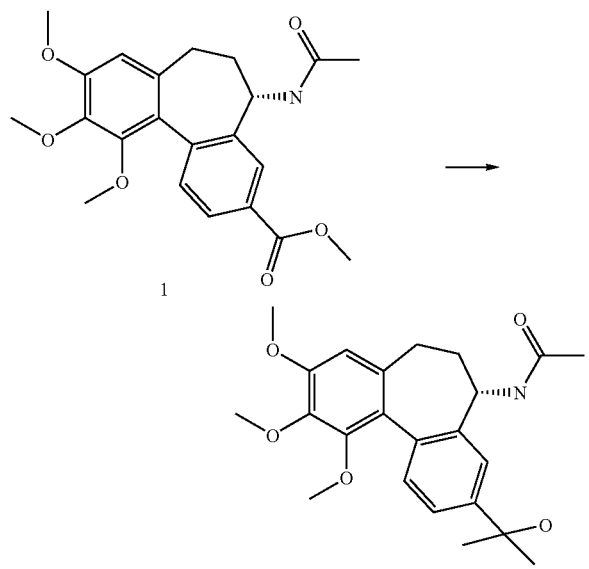

A solution of methyllithium in ether (1.6 M; 2.14 ml; 3.4 mmol) was added at –78° C. under argon atmosphere to dry THF (5 ml). After 5 minutes a solution of N-[(5S)-3-(methoxycarbonyl)-9,10,11-trimethoxy-6,7-dihydro-5H-dibenzo[a,c]cyclohepten-5-yl]acetamide (1) (0.274 g; 0.68 mmol) in THF (11 ml) was added. The mixture was stirred at –78° C. for 30 minutes, allowed to warm up and further stirred at ambient temperature for 90 minutes. After removal of the solvents by evaporation, the residue was taken up in an aqueous ammonium chloride/ethyl acetate mixture and extracted. The organic phase was evaporated and purified by flash chromatography eluting with ethyl acetate to give N-[(5S)-3-(1-hydroxy-1-methylethyl)-9,10,11-trimethoxy-6,7-dihydro-5H-dibenzo[a,c]cyclohepten-5-yl]acetamide as a white foam.

Yield: 45%

$^1$H NMR spectrum (DMSOd$_6$): 1.45 (s, 3H); 1.48 (s, 3H); 1.86 (m, 1H); 1.88 (s, 3H); 2.03 (m, 1H); 2.15 (m, 1H); 2.5 (m, 1H, signal obscured by DMSO peak); 3.5 (s, 3H); 3.77 (s, 3H); 3.83 (s, 3H); 6.77 (s, 1H); 7.23 (d, 1H); 7.35 (dd, 1H); 7.5 (d, 1H); 8.43 (d, 1H).

MS-ESI: 422.1 [MNa]$^+$

| Elemental analysis: | Found | C 66.5 | H 7.3 | N 3.5 |
| $C_{23}H_{29}NO_5$; 0.8 $H_2O$ | Required | C 66.7 | H 7.5 | N 3.4% |

EXAMPLES 25 AND 26

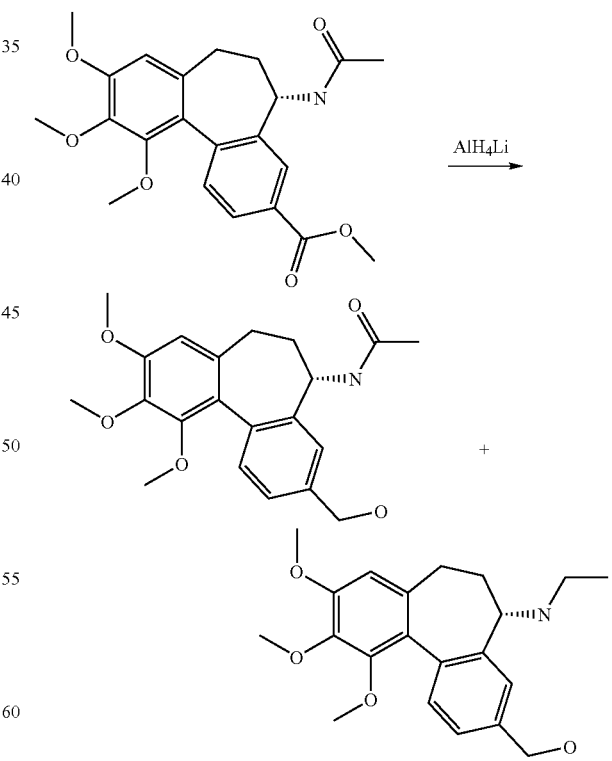

A suspension of (5S)-5-(acetylamino)-9,10,11-trimethoxy-6,7-dihydro-5H-dibenzo[a,c]cycloheptene-3-carboxylate (2.28 ml; 5.7 mmol) and lithium aluminium hydride (0.216 g; 22.8 mmol) in a mixture of THF (10 ml)

and ether (60 ml) was stirred at reflux under argon atmosphere overnight. After addition of water (60 ml), the mixture was stirred for 2 hours. The resulting solid was filtered and the filtrate was evaporated and purified by flash chromatography eluting with a 5–10% gradient of methanol/ dichloromethane to give, after evaporation, N-[(5S)-3-hydroxymethyl-9,10,11-trimethoxy-6,7-dihydro-5H-dibenzo [a,c]cyclohepten-5-yl]acetamide (yield: 33%) and [(5S)-5-(ethylamino)-9,10,11-trimethoxy-6,7-dihydro-5H-dibenzo [a,c]cyclohepten-3-yl]methanol (yield: 47%).

EXAMPLE 25

$^1$H NMR spectrum (DMSOd$_6$): 1.86 (m, 1H); 1.87 (s, 3H); 2.01 (m, 1H); 2.14 (m, 1H); 2.48 (m, 1H, signal obscured by DMSO peak); 3.46 (s, 3H); 3.77 (s, 3H); 3.83 (s, 3H); 4.54 (m, 3H); 5.21 (t, 1H); 6.78 (s, 1H); 7.27 (m, 2H); 7.32 (s, 1H); 8.42 (d, 1H).

MS-ESI: 394.1 [MH]$^+$

| Elemental analysis: | Found | C 66.0 | H 6.8 | N 3.7 |
|---|---|---|---|---|
| C$_{21}$H$_{25}$NO$_5$; 0.5 H$_2$O | Requires | C 66.3 | H 6.9 | N 3.7% |

EXAMPLE 26

$^1$H NMR spectrum (DMSOd$_6$): 1.90 (s, 3H); 1.90 (m, 1H); 2.01 (m, 1H); 2.20 (m, 1H); 2.5 (m, 1H, signal obscured by DMSO peak); 3.53 (s, 3H); 3.78 (s, 3H); 3.85 (s, 3H); 4.53 (m, 1H); 6.84 (s, 1H); 7.50 (d, 1H); 7.72 (d, 1H); 7.77 (dd, 1H); 8.45 (d, 1H).

MS-ESI: 389 [MNa]$^+$

EXAMPLE 27

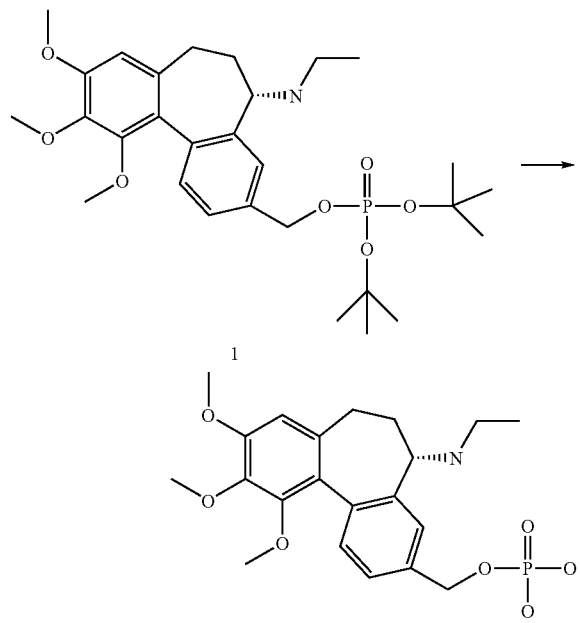

A solution of (5S)-5-(ethylamino)-9,10,11-trimethoxy-6, 7-dihydro-5H-dibenzo[a,c]cyclohepten-3-yl ditertbutyl phosphate (1) (0.215 g; 0.391 mmol) in 1M hydrogen chloride solution in 1,4-dioxane (2 ml) was stirred at ambient temperature overnight. After addition of ether (20 ml) the resulting precipitate was filtered, washed with ether and dried to give (5S)-5-(ethylamino)-9,10,11-trimethoxy-6,7-dihydro-5H-dibenzo[a,c]cyclohepten-3-yl dihydrogen phosphate.

Yield: 88%

$^1$H NMR spectrum (DMSOd$_6$): 1.04 (t, 3H); 1.78 (m, 1H); 2.0 (m, 1H); 2.32 (m, 1H); 2.5 (m, 3H, signals obscured by DMSO peak); 3.48 (s, 3H); 3.5 (m, 1H,); 3.78 (s, 3H); 3.84 (s, 3H); 4.79 (m, 3H); 6.78 (s, 1H); 7.27 (s, 2H); 7.66 (s, 1H).

MS-ESI: 460 [MH]$^+$

The starting material was prepared as follows:

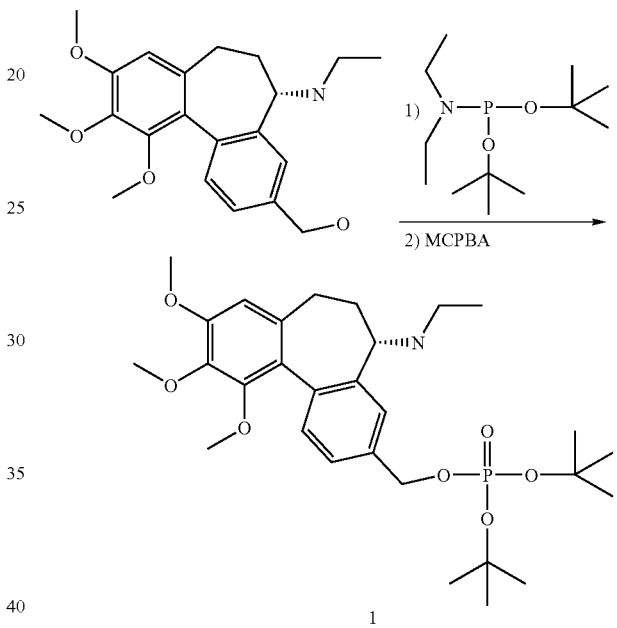

1H-Tetrazole (0.182 g; 2.6 mmol) was added, under argon atmosphere, to a solution of [(5S)-5-(ethylamino)-9,10,11-trimethoxy-6,7-dihydro-5H-dibenzo[a,c]cyclohepten-3-yl] methanol, (prepared as described in Example 26), (0.3 g; 0.84 mmol) and di-tert-butyl diethylphosphoramidite (0.33 g; 1.34 mmol) in dry THF (5.5 ml). After 5 minutes, the solution was cooled to −78° C. and a solution of m-chloroperbenzoic acid (0.375 g; 1.68 mmol) in dichloromethane (3 ml) was added in portions. The mixture was allowed to warm to ambient temperature and further stirred for 5 minutes. After addition of aqueous ammonium hydrogen carbonate and aqueous sodium sulphite, the organic solvent was removed by evaporation and the residue was taken up in dichloromethane. The organic phase was washed with water, dried and evaporated. The residue was purified by flash chromatography eluting with ethyl acetate/methanol (95/5) to give (1) as a foam.

Yield: 54%.

$^1$H NMR spectrum (DMSOd$_6$): 1.03 (t, 3H); 1.43 (s, 18H); 1.72 (m, 1H); 2.0 (m, 1H); 2.35 (m, 1H); 2.50 (m, 3H, signal obscured by DMSO peak); 3.2–3.6 (m, 1H signal obscured by H$_2$O peak); 3.50 (s, 3H); 3.78 (s, 3H); 3.84 (s, 3H); 4.99 (m, 2H); 6.80 (s, 1H); 7.35 (m, 2H).

EXAMPLE 28

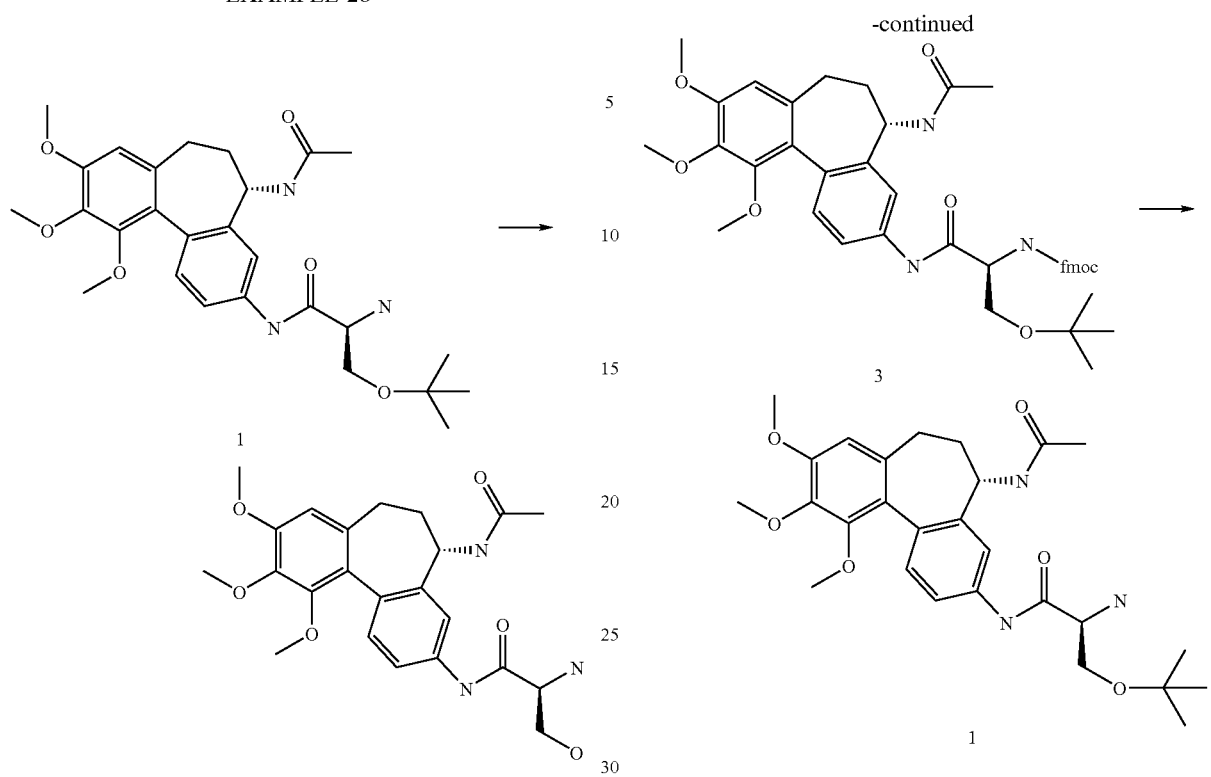

12N Hydrochloric acid (5 ml) was added to a solution of (2S)-N-[(5S)-5-(acetylamino)-9,10,11-trimethoxy-6,7-dihydro-5H-dibenzo[a,c]cyclohepten-3-yl]-2-amino-3-tertbutoxypropanamide (1) (0.35 g; 0.7 mmol) in 1,4-dioxane (5 ml). The mixture was heated at 60° C. under argon atmosphere for 1 hour. After dilution with ether, the resulting precipitate was filtered, washed with ether and dried to give (2S)-N-[(5S)-5-(acetylamino)-9,10,11-trimethoxy-6,7-dihydro-5H-dibenzo[a,c]cyclohepten-3-yl]-2-amino-3-hydroxypropanamide as a white solid.

Yield: 65%

$^1$H NMR spectrum (DMSOd$_6$): 1.90 (s, 3H); 1.95 (, 1H); 2.05 (m, 1H); 2.18 (m, 1H); 2.50 (m, 1H, signal obscured by DMSO peak); 3.48 (s, 3H); 3.79 (s, 3H); 3.84 (s, 3H); 3.88 (m, 2H); 4.05 (m, 1H); 4.45 (m, 1H); 6.8 (s, 1H); 7.29 (d, 1H); 7.58 (d, 1H); 7.65 (dd, 1H); 8.32 (br s, 3H); 8.47 (d, 1H).

MS-ESI: 444 [MH]$^+$

The starting materials was prepared as follows:

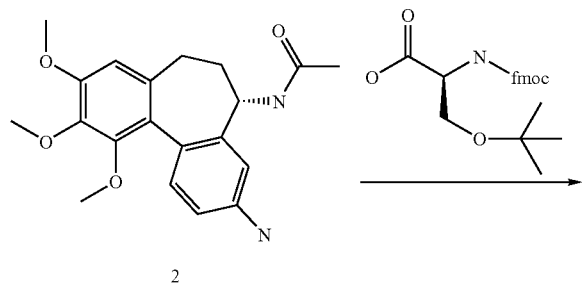

O-(7-(Azabenzotriazol-1-yl)-N,N,N',N'-tetramethyluronium hexafluorophosphate (0.468 g; 1.28 mmol) and N-[(5S)-3-amino-9,10,11-trimethoxy-6,7-dihydro-5H-dibenzo[a,c]cyclohepten-5-yl]acetamide (2) (0.398 g; 1.12 mmol) were added to a solution of N-fmoc-O-tert-butyl-l-serine (0.428 g; 1.12 mmol) in dichloromethane (18 ml) and N,N-diisopropylethylamine (0.222 ml; 1.28 mmol). The mixture was stirred overnight under argon atmosphere at ambient temperature. After addition of water, the organic phase was dried over MgSO$_4$ and evaporated to give (2S)-N-[(5S)-5-(acetylamino)-9,10,11-trimethoxy-6,7-dihydro-5H-dibenzo[a,c]cyclohepten-3-yl]-2-(fmoc-amino)-3-(tert-butoxy)propanamide (3).

Yield: 95%

$^1$H NMR spectrum (DMSOd$_6$): 1.14 (s, 9H); 1.87 (s, 3H); 1.80 (m, 1H); 2.0–2.2 (m, 2H); 2.5 (m, 1H, signal obscured by DMSO peak); 3.46 (s, 3H); 3.50–3.60 (m, 2H); 3.77 (s, 3H); 3.82 (s, 3H); 4.20–4.35 (m, 4H); 4.45 (m, 1H); 6.77 (s, 1H); 7.25 (d, 1H); 7.32 (m, 2H); 7.42 (m, 2H); 7.54 (m, 2H); 7.61 (s, 1H); 7.76 (m, 2H); 7.89 (m, 2H); 8.40 (d, 1H).

MS-ESI: 744 [MNa]$^+$

A solution of (3) (0.75 g; 1.04 mmol) and piperidine (1 ml) in dichloromethane (1.5 ml) was stirred at ambient temperature for 45 minutes. After evaporation to dryness the residue was purified by flash chromatography eluting with ethyl acetate/methanol (95/5) to give (1) as a foam.

Yield: 70%

$^1$H NMR spectrum (DMSOd$_6$): 1.14 (s, 9H); 1.87 (s, 3H); 1.89 (m, 1H); 1.90–2.15 (m, 2H); 2.5 (m, 1H, signal obscured by DMSO peak); 3.46 (s, 3H); 3.40–3.50 (m, 3H); 3.77 (s, 3H); 3.82 (s, 3H); 4.49 (m, 1H); 6.77 (s, 1H); 7.25 (d, 1H); 7.58 (m, 2H); 8.39 (d, 1H).

MS-ESI: 500.2 [MH]$^+$

EXAMPLE 29

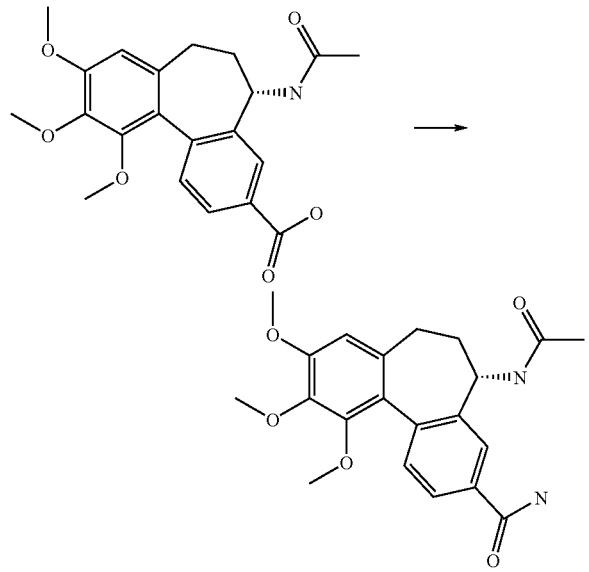

Oxalyl chloride (0.44 g; 3.4 mmol) and DMF (50 µl) were added to a suspension of N-[(5S)-3-carboxy-9,10,11-trimethoxy-6,7-dihydro-5H-dibenzo[a,c]cyclohepten-5-yl]acetamide (1) under argon atmosphere (1.15 g; 3 mmol) in dichloromethane (10 ml). The mixture was stirred at ambient temperature for 2 hours, evaporated to dryness and redissolved in dichloromethane (20 ml). The solution was cooled at −78° C. and ammonia gas was allowed to bubble through the solution for 5 minutes. The mixture was allowed to warm up and further stirred at ambient temperature for 15 minutes. After evaporation to dryness, the residue was taken up in aqueous sodium hydrogen carbonate/ethyl acetate. The organic phase was separated, evaporated and purified by flash chromatography eluting with ethyl acetate/methanol (95/5) to give N-[(5S)-3-carbamoyl-9,10,11-trimethoxy-6,7-dihydro-5H-dibenzo[a,c]cyclohepten-5-yl]acetamide.

Yield: 20%

$^1$H NMR spectrum (DMSOd$_6$): 1.89 (s, 3H); 1.89 (m, 1H); 1.96 (m, 1H); 2.5 (m, 1H, signal obscured by DMSO peak); 3.49 (s, 3H); 3.78 (s, 3H); 3.84 (s, 3H); 4.54 (m, 1H); 6.81 (s, 1H); 7.36 (d, 1H); 7.78 (dd, 1H); 7.87 (d, 1H); 7.96 (s, 1H); 8.47 (d, 1H).

MS-ESI: 407 [MNa]$^+$

EXAMPLE 30

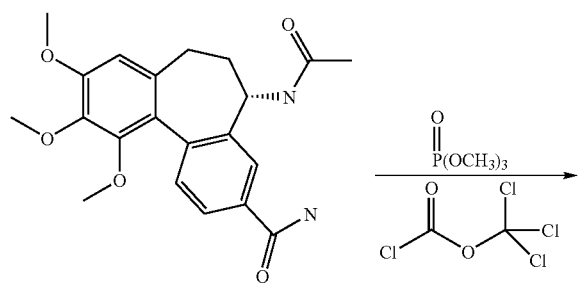

-continued

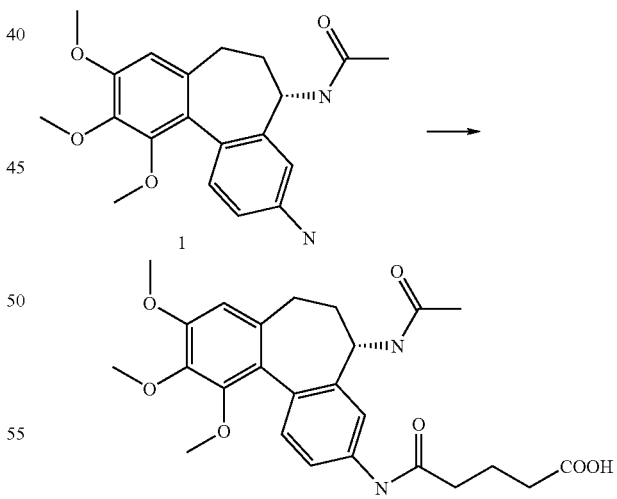

Trichloromethyl chloroformate (0.094 ml; 0.77 mmol) was added in portions at 0° C. to a solution of N-[(5S)-3-carbamoyl-9,10,11-trimethoxy-6,7-dihydro-5H-dibenzo[a,c]cyclohepten-5-yl]acetamide (0.2 g; 0.484 mmol), (prepared as described for Example 29) and trimethyl phosphate (0.306 ml; 2.6 mmol). The mixture was allowed to warm up and then heated at 60° C. for 5 minutes. The reaction mixture was poured onto ice and stirred. The resulting precipitate was filtered, dried and purified by flash chromatography, eluting with dichloromethane/ethyl acetate (1/1) to give N-[(5S)-3-cyano-9,10,11-trimethoxy-6,7-dihydro-5H-dibenzo[a,c]cyclohepten-5-yl]acetamide.

Yield: 61%.

$^1$H NMR spectrum (DMSOd$_6$): 0.97 (t, 3H); 1.60 (m, 1H); 1.95 (m, 2H); 2.30 (m, 2H); 2.45 (m, 1H, signal partially obscured by DMSO peak); 3.46 (s, 3H); 3.76 (s, 3H); 3.83 (s, 3H); 4.54 (m, 2H); 5.16 (t, 1H); 6.75 (s, 1H); 7.15–7.30 (m, 2H); 7.53 (s, 1H).

MS-ESI: 358 [MH]$^+$

EXAMPLE 31

A solution of N-[(5S)-3-amino-9,10,11-trimethoxy-6,7-dihydro-5H-dibenzo[a,c]cyclohepten-5-yl]acetamide (1) (0.3 g; 84 mmol) and glutaric anhydride (0.199 g; 84 mmol) in dichloromethane (20 ml) was stirred at ambient temperature for 90 minutes. After removal of the solvent by evaporation, the residue was purified by flash chromatography, eluting with dichloromethane/methanol (80/20) to give, after trituration in ether, N-[(5S)-3-(4-carboxybutanoylamino)-9, 10,11-trimethoxy-6,7-dihydro-5H-dibenzo[a,c]cyclohepten-5-yl]acetamide as a white solid.

Yield: 63%

¹H NMR spectrum (DMSOd₆): 1.8–2 (m, 3H); 1.88 (s, 3H); 2–2.25 (m, 2H); 2.26 (t, 2H); 2.36 (t, 2H); 2.5 (s, 1H, signal partially observed by DMSO peak); 3.46 (s, 3H); 3.77 (s, 3H); 3.82 (s, 3H); 4.48 (m, 1H); 6.76 (s, 1H); 7.22 (d, 1H); 7.53 (d, 1H); 7.56 (s, 1H); 8.4 (d, 1H); 9.97 (s, 1H).

MS-ESI: 471 [MH]⁺

| Elemental analysis | Found | C 59.2 | H 6.2 | N 5.4 |
| C₂₅H₃₀N₂O₇ | Requires | C 63.8 | H 6.4 | N 6.0% |

EXAMPLE 32

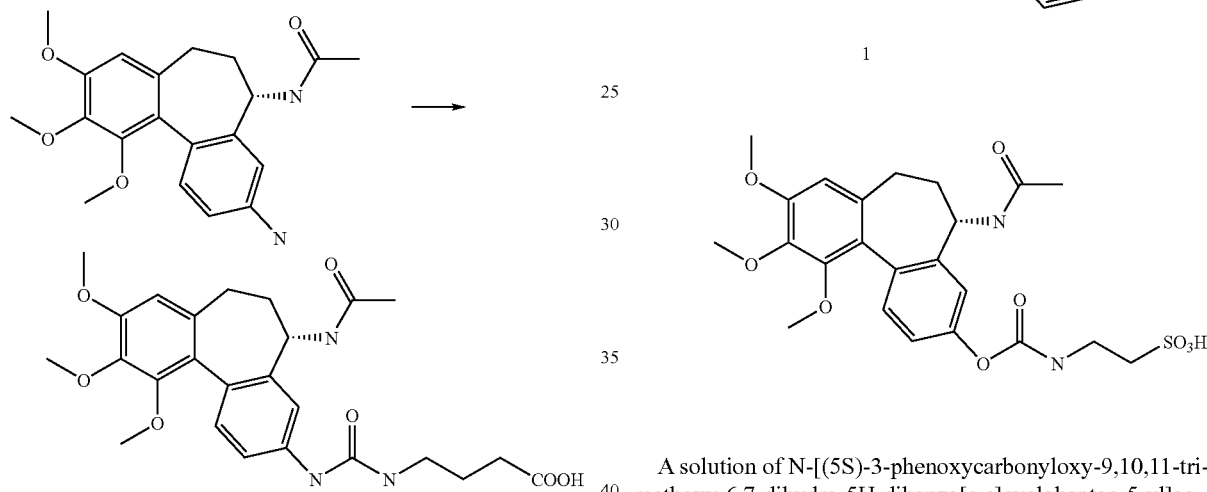

A suspension of 4-aminobutyric acid (0.111 g; 1.08 mmol) and N,O-bis(trimethylsilyl)acetamide (1.8 ml; 7.3 mmol) in dichloromethane (10 ml) was stirred at ambient temperature for 2 hours. The mixture was evaporated to dryness and redissolved in dichloromethane (10 ml) under argon atmosphere. A solution of N-[(5S)-3-amino-9,10,11-trimethoxy-6,7-dihydro-5H-dibenzo[a,c]cyclohepten-5-yl]acetamide (0.35 g; 0.98 mmol), phenyl chloroformate (135 µl; 1.08 mmol) and triethylamine (151 µl; 1.08 mmol) in dichloromethane (10 ml) was stirred for 1 hour under argon atmosphere and added to the above solution. The mixture was stirred overnight, evaporated and purified by preparative HPLC on reverse phase silica eluting with a 0–30% gradient of methanol/ammonium carbonate buffer pH7 to give, after evaporation, 4-[([(5S)-5-(acetylamino)-9,10,11-trimethoxy-6,7-dihydro-5H-dibenzo[a,c]cyclohepten-3-yl]aminocarbonyl)amino]butanoic acid as a solid Yield: 50%

¹H NMR spectrum (DMSOd₆, CF₃CO₂D): 1.68 (m, 2H); 1.88 (s, 3H); 1.85–2 (m, 1H); 2–2.2 (m, 2H); 2.27 (m, 2H); 2.5 (m, 1H, signal partially observed by DMSO peak); 3.12 (m, 2H); 3.47 (s, 3H); 3.78 (s, 3H); 3.83 (s, 3H); 4.48 (m, 1H); 6.75 (s, 1H); 7.17 (d, 1H); 7.3 (s, 1H); 7.39 (d, 1H).

MS-ESI: 486 [MH]⁺

| Elemental analysis | Found | C 58.3 | H 6.5 | N 8.7 |
| C₂₅H₃₁N₃O₇ | Requires | C 61.8 | H 6.4 | N 8.7% |

EXAMPLE 33

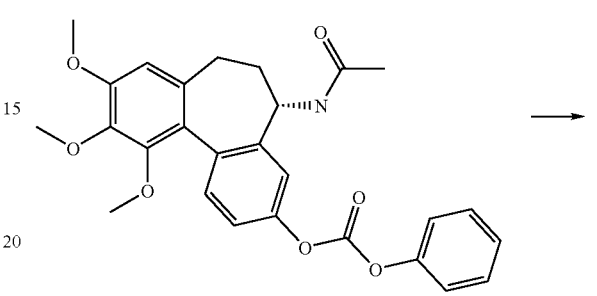

A solution of N-[(5S)-3-phenoxycarbonyloxy-9,10,11-trimethoxy-6,7-dihydro-5H-dibenzo[a,c]cyclohepten-5-yl]acetamide (1) (0.35 g; 0.73 mmol), 2-aminomethanesulphonic acid (0.156 g; 1.25 mmol) and triethylamine (174 µl; 1.25 mmol) in DMSO (2.5 ml) was heated at 70° C. for 2 days. The mixture was taken up in water and purified by preparative HPLC eluting with a 0–30% gradient of methanol/ammonium carbonate buffer (2 g/l pH7). The appropriate fractions were evaporated and the resulting solid triturated in ether and dried to give 2-[([(5S)-5-(acetylamino)-9,10,11-trimethoxy-6,7-dihydro-5H-dibenzo[a,c]cyclohepten-3-yl]oxycarbonyl)amino]ethane-1-sulphonic acid.

Yield: 22%

¹H NMR spectrum (DMSOd₆; CF₃CO₂D): 1.89 (s, 3H); 1.8–1.95 (m, 1H); 2–2.5 (m, 2H); 2.5 (m, 1H, signal partially obscured by DMSO peak); 2.71 (t, 2H); 3.4 (m, 2H); 3.54 (s, 3H); 3.8 (s, 3H); 3.85 (s, 3H); 4.58 (m, 1H); 6.8 (s, 1H); 7.08 (d, 1H); 7.1 (s, 1H); 7.32 (d, 1H).

MS-ESI: 509 [MH]⁺

| Elemental analysis: | Found | C 48.1 | H 6.0 | N 7.3 | S 5.2 |
| C₂₃H₂₈N₂O₉S; | Requires | C 48.4 | H 6.4 | N 7.4 | S 5.6% |
| 1 NH₃, 2.5 H₂O | | | | | |

The starting material was prepared as follows:

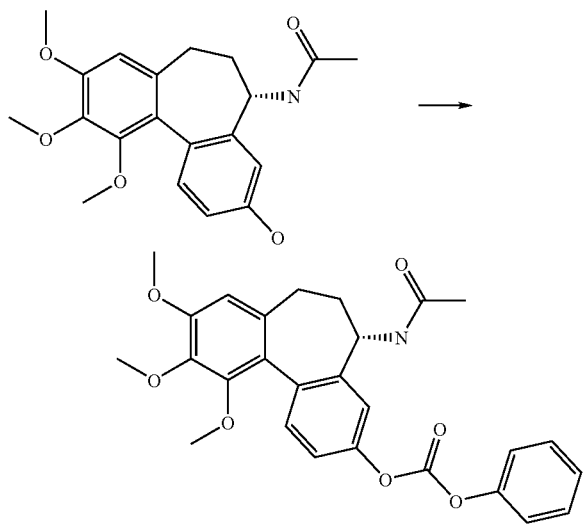

A solution of N-acetyl colchicinol (0.35 g; 0.98 mmol), phenyl chloroformate (145 µl; 1.08 mmol) and triethylamine (150 µl; 1.08 mmol) in dichloromethane (20 ml) was stirred at ambient temperature for 1 hour. The mixture was washed with water and the organic phase evaporated. The residue was purified by flash chromatography, eluting with ethyl acetate/petroleum ether (80/20) to give N-[(5S)-3-phenoxycarbonyloxy-9,10,11-trimethoxy-6,7-dihydro-5H-dibenzo[a,c]cyclohepten-5-yl]acetamide as a foam.

Yield: 79%

$^1$H NMR spectrum (DMSOd$_6$): 1.89 (s, 3H); 1.8–1.95 (m, 1H); 2–2.3 (m, 2H); 2.5 (m 1H, signal partially obscured by DMSO peak); 3.52 (s, 3H); 3.78 (s, 3H); 3.84 (s, 3H); 4.58 (m, 1H); 6.8 (s, 1H); 7.2–7.6 (m, 8H); 8.41 (d, 1H).

EXAMPLE 34

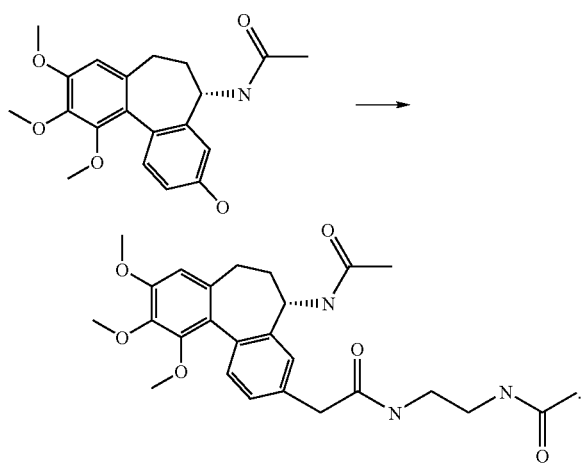

A solution of N-acetyl-cochicinol (0.25 g; 0.7 mmol), 4-nitrophenyl chloroformate (0.169 g; 0.84 mmol) and triethylamine (117 µl; 0.84 mmol) in dichloromethane (10 ml) was stirred under argon atmosphere for 1 hour. N-Acetyl-ethylenediamine (0.086 g; 0.84 mmol) was then added and the mixture was stirred further for 3 hours. After evaporation to dryness, the residue was purified by flash chromatography, eluting with methanol/acetonitrile/dichloromethane (4/48/48) to give (5S)-5-(acetylamino)-9,10,11-trimethoxy-6,7-dihydro-5H-dibenzo[a,c]cyclohepten-3-yl N-[2-(acetylamino)ethyl]carbamate.

Yield: 49%

$^1$H NMR spectrum (DMSOd$_6$): 1.84 (s, 3H); 1.88 (s, 3H); 1.85–1.95 (m, 1H); 2–2.25 (m, 2H); 2.5 (m, 1H, signal partially observed by H$_2$O peak); 3.53 (s, 3H); 3.79 (s, 3H); 3.85 (s, 3H); 4.55 (m, 1H); 6.81 (s, 1H); 7.06 (dd, 1H); 7.07 (d, 1H); 7.32 (d, 1H); 7.79 (m, 1H); 7.8 (m, 1H); 8.41 (d, 1H).

MS-ESI: 486.1 [MH]$^+$

| Elemental analysis | Found | C 60.3 H 6.6 N 8.3 |
|---|---|---|
| C$_{25}$H$_{31}$N$_3$O$_7$ 0.6 H$_2$O | Requires | C 60.5 H 6.5 N 8.5% |

EXAMPLE 35

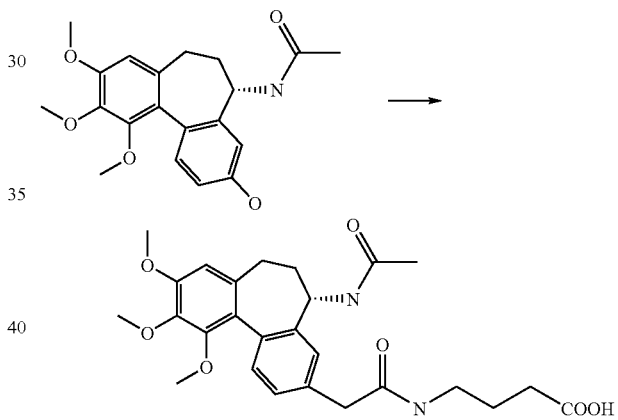

A suspension of 4-aminobutyric acid (0.087 g; 0.84 mmol) and N,O-bis(trimethylsilyl)acetamide (0.865 ml; 3.5 mmol) in dichloromethane (10 ml) was stirred under argon atmosphere for 3 hours and evaporated to dryness. The residue was then redissolved in dichloromethane (10 ml). 4-Nitrophenyl chloroformate (0.17 g; 0.84 mmol) and triethylamine (0.117 ml; 0.84 mmol) were added to a solution of N-acetyl-colchicinol (0.25 g; 0.7 mmol) in dichloromethane (10 ml). The solution was stirred for 1 hour and added to the above solution. The resulting mixture was stirred further for 3 hours. After evaporation to dryness the residue was purified by preparative HPLC on reverse phase silica eluting with methanol/ammonium carbonate buffer (2 g/l pH7) (30/70) to give, after evaporation of the appropriate fractions, 4-[([(5S)-5-(acetylamino)-9,10,11-trimethoxy-6,7-dihydro-5H-dibenzo[a,c]cyclohepten-3-yl]oxycarbonyl)amino]butanoic acid.

Yield: 44%

$^1$H NMR spectrum (DMSOd$_6$, CF$_3$CO$_2$D): 1.73 (m, 2H); 1.88 (s, 3H); 1.8–1.95 (m, 1H); 2–2.25 (m, 2H); 2.3 (m, 2H);

2.5 (m, 1H, signal partially obscured by DMSO peak); 3.11 (m, 2H); 3.53 (s, 3H); 3.79 (s, 3H); 3.84 (s, 3H); 4.45 (m, 1H); 6.8 (s, 1H); 7.05 (dd, 1H); 7.07 (d, 1H); 7.31 (d, 1H); 7.87 (m, 1H); 8.42 (d, 1H).

MS-ESI: 487.1 [MH]$^+$

| Elemental analysis | Found | C 60.2 | H 6.3 | N 6.0 |
|---|---|---|---|---|
| $C_{25}H_{30}N_2O_8$ 0.5 $H_2O$ | Requires | C 60.6 | H 6.3 | N 5.7% |

EXAMPLE 36

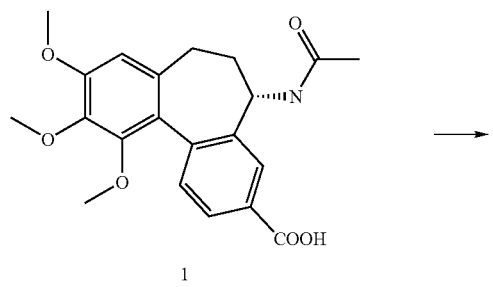

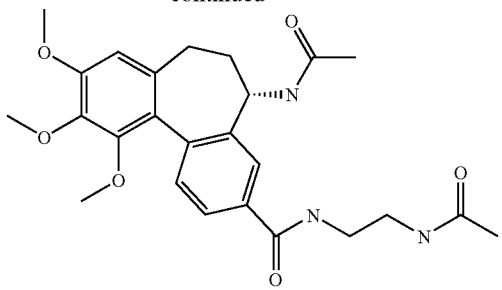

A mixture of N-[(5S)-3-carboxy-9,10,11-trimethoxy-6,7-dihydro-5H-dibenzo[a,c]cyclohepten-5-yl]acetamide (1) (0.3 g; 0.78 mmol), DCCI (0.193 g; 0.93 mmol), DMAP (0.019 g; 0.15 mmol) and N-acetylethylenediamine (0.096 g; 0.985 mmol) in dichloromethane was stirred at ambient temperature overnight. After evaporation of the solvent, the residue was purified by flash chromatography and eluted with methanol/dichloromethane (10/90) to give N-[(5S)-3-(2-acetylaminoethylcarbamoyl)-9,10,11-trimethoxy-6,7-dihydro-5H-dibenzo[a,c]cyclohepten-5-yl]acetamide.

Yield: 71%

$^1$H NMR spectrum (DMSOd$_6$): 1.82 (s, 3H); 1.89 (s, 3H); 1.85–2.05 (m, 2H); 2.17 (m, 1H); 2.5 (m, 1H, signal partially obscured by DMSO peak); 3.22 (m, 2H); 3.32 (m, 2H, signal partially observed by H$_2$O peak); 3.49 (s, 3H); 3.79 (s, 3H); 3.84 (s, 3H); 4.55 (m, 1H); 6.81 (s, 1H); 7.38 (d, 1H); 7.75 (dd, 1H); 7.84 (d, 1H); 8 (m, 1H); 8.52 (m, 2H).

MS-ESI: 470.2 [MH]$^+$

| Elemental analysis: | Found | C 60.3 | H 6.6 | N 8.2 |
|---|---|---|---|---|
| $C_{25}H_{31}N_3O_6$ 0.4 dichloromethane | Requires | C 60.6 | H 6.4 | N 8.4% |

EXAMPLE 37

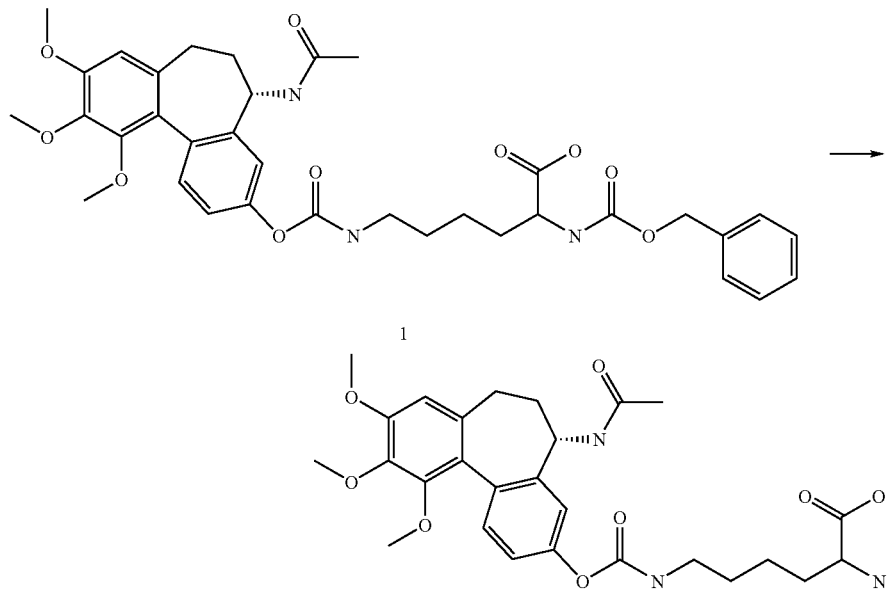

A solution of 6-[({[(5S)-5-(acetylamino)-9,10,11-trimethoxy-6,7-dihydro-5H-dibenzo[a,c]cyclohepten-3-yl]oxy}carbonyl)amino]-2-(benzyloxycarbonylamino)-hexanoic acid (1) (0.4 g; 0.6 mmol) in ethanol (80 ml) was hydrogenated in the presence of 10% palladium on carbon (0.08 g). After filtration of the catalyst and evaporation to dryness, the residue was purified by preparative HPLC eluting with a 0–40% gradient of methanol/ammonium carbonate buffer (2 g/l pH7) to give, after evaporation and trituration in ether, 6-[({[(5S)-5-(acetylamino)-9,10,11-trimethoxy-6,7-dihydro-5H-dibenzo[a,c]cyclohepten-3-yl]oxy}carbonyl)amino]-2-aminohexanoic acid as a solid.

Yield: 75%

$^1$H NMR spectrum (DMSOd$_6$): 1.35–1.55 -m, 4H); 1.62 (m, 1H); 1.72 (m, 1H); 1.9 (s, 3H); 1.9 (m, 1H); 2.05 (m, 1H); 2.15 (m, 1H); 2.5 (m, 1H, signal partially obscured by DMSO peak); 3–3.2 (m, 3H); 3.51 (s, 3H); 3.78 (s, 3H); 3.83 (s, 3H); 4.55 (m, 1H); 6.79 (s, 1H); 7.02 (dd, 1H); 7.12 (d, 1H); 7.29 (d, 1H); 7.74 (m, 1H); 8.7 (d, 1H).

MS-ESI: 530.1 [MH]$^+$

| Elemental analysis: | Found | C 60.2 | H 7.0 | N 7.8 |
| $C_{27}H_{35}N_3O_9$ 0.5 $H_2O$ | Requires | C 60.2 | H 6.7 | N 7.8% |

The starting material was prepared as follows:

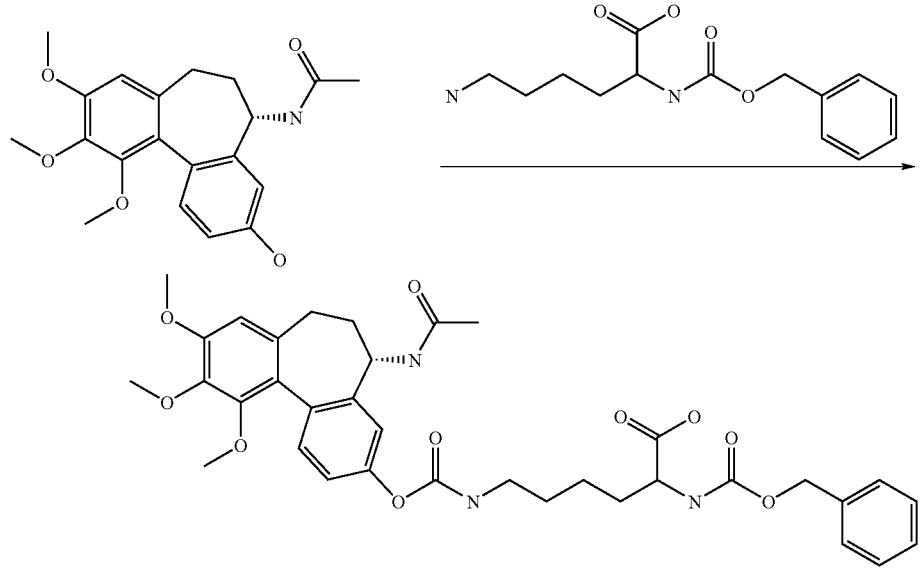

A suspension of N-(carboxybenzyloxy)-L-lysine (0.141 g; 0.5 mmol) and N,O-bis(trimethylsilyl)acetamide (0.519 ml; 2 mmol) in dichloromethane (10 ml) was stirred at ambient temperature under argon atmosphere for 3 hours. The mixture was evaporated to dryness and the residue redissolved in dichloromethane (10 ml). A solution of N-acetyl-colchicinol (0.15 g; 0.42 mmol), and 4-nitrophenyl chloroformate (0.102 g; 0.5 mmol) was stirred at ambient temperature for 1 hour and then added to the above solution. The resulting mixture was stirred overnight, evaporated to dryness and purified by preparative HPLC eluting with a 0–55% gradient of methanol/ammonium carbonate buffer (2 g/l pH7) to give (1).

Yield: 63%

$^1$H NMR spectrum (DMSOd$_6$): 1.35 (m, 2H); 1.49 (m, 2H); 1.62 (m, 1H); 1.72 (m, 1H); 1.89 (s, 3H); 1.9 (m, 1H); 2.07 (m, 1H); 2.15 (m, 1H); 2.5 (m, 1H, signal partially obscured by DMSO peak); 3.07 (m, 2H); 3.52 (s, 3H); 3.8 (s, 3H); 3.85 (s, 3H); 4.57 (m, 1H); 5.05 (m, 2H); 6.81 (s, 1H); 7 (m, 1H); 7.05 (dd, 1H); 7.1 (d, 1H); 7.32 (d, 1H); 7.3–7.4 (m, 5H); 7.75 (m, 1H; 8.58 (d, 1H).

EXAMPLE 38

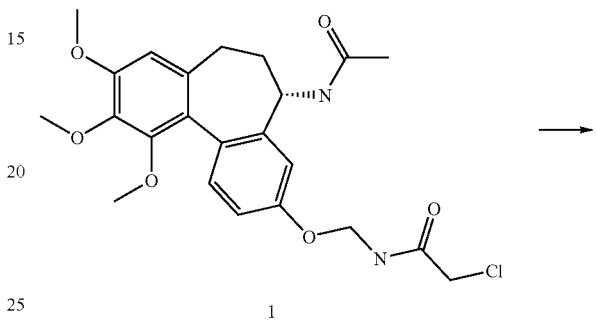

-continued

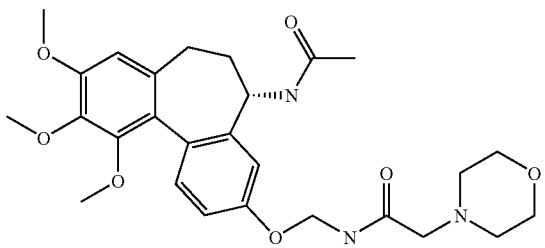

A solution of N-([(5S)-5-(acetylamino)-9,10,11-trimethoxy-6,7-dihydro-5H-dibenzo[a,c]cyclohepten-3-yl]oxymethyl)-2-chloroacetamide (1) (0.25 g; 0.55 mmol) in morpholine (2 ml)) was stirred at ambient temperature for 2 hours. After addition of dichloromethane and removal of the insoluble material by filtration, the filtrate was evaporated to dryness and the residue was purified by preparative HPLC eluting with a 0–45% gradient of ethanol/ammonium carbonate buffer (2 g/l pH7) to give, after evaporation and trituration in ether, N-([(5S)-5-(acetylamino)-9,10,11-trimethoxy-6,7-dihydro-5H-dibenzo[a,c]cyclohepten-3-yl]oxymethyl)-2-morpholinoacetamide.

Yield: 60%

$^1$H NMR spectrum (DMSOd$_6$): 1.85 (m, 1H); 1.88 (s, 3H); 1.95–2.2 (m, 2H); 2.4 (m, 4H); 2.5 (m, 1H, signal partially observed by DMSO peak); 3 (s, 2H); 3.47 (s, 3H); 3.57 (m, 4H); 3.77 (s, 3H); 3.82 (s, 3H); 4.5 (m, 1H); 5.18 (m, 2H); 6.76 (s, 1H); 6.91 (d, 1H); 6.98 (dd, 1H); 7.22 (d, 1H); 8.32 (m, 1H); 8.85 (m, 1H).

MS-ESI: 514.1 [MH]$^+$

| Elemental analysis | Found | C 61.2 | H 6.9 | N 7.9 |
| $C_{27}H_{35}N_3O_7$ | Requires | C 61.4 | H 7.0 | N 8.0% |

The starting material was prepared as follows:

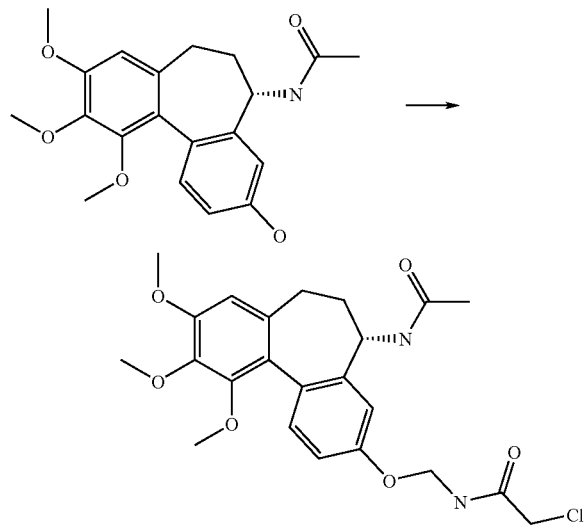

2-Chloro-N-(hydroxymethyl)-acetamide (0.342 g; 2.7 mmol), triphenylphosphine (1.1 g; 4.19 mmol) and DEAD (0.6 ml; 4.19 mmol) were added to a solution of N-acetyl-colchicinol (0.3 g; 0.84 mmol) in dichloromethane (20 ml) under argon atmosphere. The mixture was stirred at ambient temperature for 2 hours, evaporated and purified by flash chromatography eluting with ethyl acetate/dichloromethane (50/50) and dichloromethane/methanol (98/2) to give (1).

Yield: 76%

MS-ESI: 485.1 [MH]$^+$

EXAMPLE 39

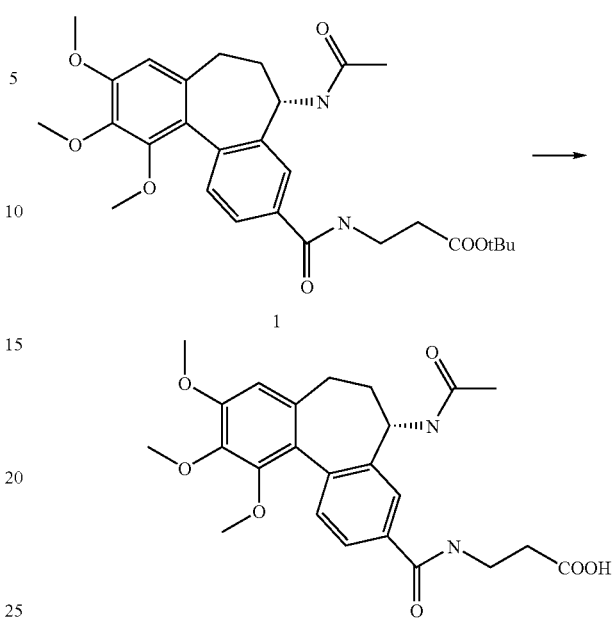

N-[(5S)-3-(2-tertButoxycarbonylethylcarbamoyl)-9,10,11-trimethoxy-6,7-dihydro-5H-dibenzo[a,c]cyclohepten-5-yl]acetamide (1) (0.26 g; 0.5 mmol) in solution in dichloromethane (10 ml) was treated with TFA (10 ml) at ambient temperature for 1 hour. After evaporation to dryness, the residue was purified by preparative HPLC eluting with methanol/ammonium carbonate buffer (2 g/l pH7) (35/65) to give, after evaporation and trituration in ether, 3-[(5S)-5-(acetylamino)-9,10,11-trimethoxy-6,7-dihydro-5H-dibenzo[a,c]cyclohepten-3-ylcarbonylamino]propanoic acid as a white solid.

Yield: 56%

$^1$H NMR spectrum (DMSOd$_6$): 1.91 (s, 3H); 1.85–2.1 (m, 2H); 2.2 (m, 1H); 2.5 (m, 1H, signal partially observed by DMSO peak); 3.2–3.6 (m, 4H, signal partially obscured by H$_2$O peak); 3.5 (s, 3H); 3.8 (s, 3H); 3.86 (s, 3H); 4.6 (m, 1H); 6.82 (s, 1H); 7.39 (d, 1H); 7.74 (dd, 1H); 7.85 (d, 1H); 8.54 (d, 1H); 8.62 (m, 1H).

MS-ESI: 457.1 [MH]$^+$

| Elemental analysis: | Found | C 60.9 | H 6.7 | N 6.7 |
| $C_{24}H_{28}N_2O_7$ | Requires | C 63.2 | H 6.2 | N 6.1% |

The starting material was prepared as follows:

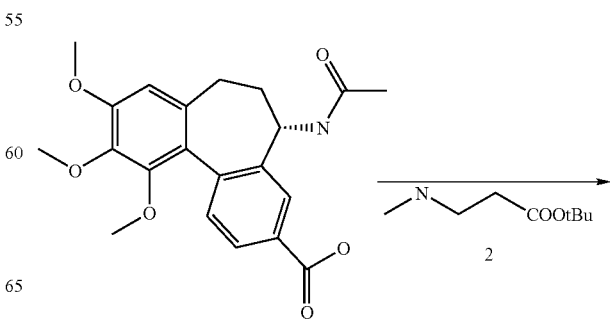

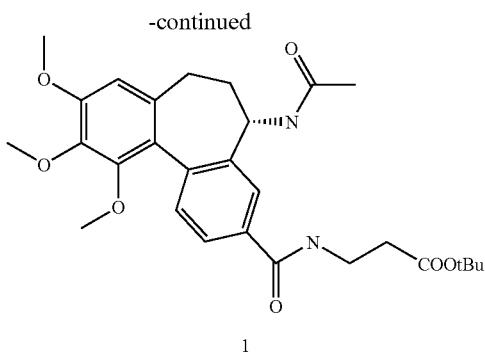

1

A mixture of N-[(5S)-3-carboxy-9,10,11-trimethoxy-6,7-dihydro-5H-dibenzo[a,c]cyclohepten-5-yl]acetamide (1) (0.3 g; 0.78 mmol), EDCI (0.179 g; 0.93 mmol), DMAP (0.019 g; 0.15 mmol), triethylamine (0.13 ml; 0.985 mmol) and tertbutyl 3-methylaminopropanoate (0.17 g; 0.985 mmol) in dichloromethane was stirred at ambient temperature overnight. After removal of the solvent by evaporation, the residue was purified by flash chromatography and eluted with ethyl acetate to give (1).

Yield: 84%

$^1$H NMR spectrum (DMSOd$_6$): 1.4 (s, 9H); 1.89 (s, 3H); 1.9 (m, 1H); 2 (m, 1H); 2.17 (m, 1H); 2.5 (m, 1H, signal partially obscured by DMSO peak); 3.25–3.55 (m, 4H); 3.49 (s, 3H); 3.78 (s, 3H); 3.84 (s, 3H); 4.55 (m, 1H); 6.81 (s, 1H); 7.37 (d, 1H); 7.7 (dd, 1H); 7.81 (d, 1H); 8.5 (m, 2H).

EXAMPLE 40

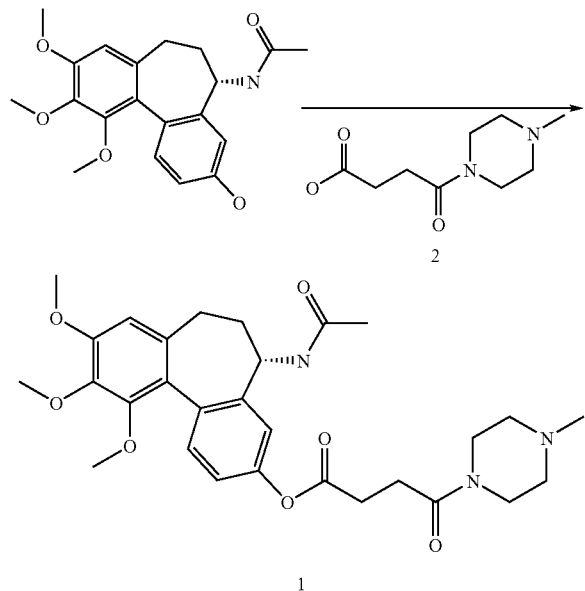

A suspension of 3-(4-methylpiperazin-1-ylcarbonyl)propanoic acid (2) (0.219 g; 1.1 mmol), DCCI (0.226 ml; 1.1 mmol) and DMAP (0.052 ml; 0.42 mmol) in dichloromethane (20 ml) was stirred under argon atmosphere for 1 hour. N-Acetyl-colchicinol (0.3 g; 0.84 mmol) was then added and the mixture was stirred overnight. After removal of the insoluble material by filtration, the filtrate was evaporated and purified by preparative HPLC eluting with a 0–50% gradient of methanol/ammonium carbonate buffer (2 g/l pH7) to give (5S)-5-(acetylamino)-9,10,11-trimethoxy-6,7-dihydro-5H-dibenzo[a,c]cyclohepten-3-yl 3-[4-methylpiperazin-1-ylcarbonyl]propanoate.

Yield: 48%

$^1$H NMR spectrum (DMSOd$_6$): 1.80–1.96 (m, 1H); 1.88 (s, 3H); 2.07 (m, 1H); 2.18 (m, 1H); 2.20 (s, 3H); 2.26 (m, 2H); 2.33 (m, 2H); 2.59 (m, 1H, signal partially obscured by DMSO peak); 2.73 (m, 2H); 2.79 (m, 2H); 3.48 (m, 4H); 3.53 (s, 3H); 3.80 (s, 3H); 3.86 (s, 3H); 4.55 (m, 1H); 6.82 (s, 1H); 7.03–7.12 (m, 2H); 7.36 (d, 1H); 8.43 (d, 1H).

MS-ESI: 540 [MH]$^+$

| Elemental analysis | Found | C 63.9 H 7.1 N 7.5 |
| --- | --- | --- |
| C$_{29}$H$_{37}$N$_3$O$_7$; 0.3 H$_2$O | Requires | C 63.9 H 7.0 N 7.7% |

The starting material was prepared as follows:

A suspension of N-methylpiperazine (1.1 ml; 10 mmol) and succinic anhydride (1.2 g; 12 mmol) in dichloromethane (20 ml) was stirred under argon atmosphere for 24 hours. After evaporation to dryness, the residue was triturated in ether/pentane to give (2) as a solid.

Yield: 91%

$^1$H NMR Spectrum (DMSOd$_6$): 2.37 (s, 3H); 2.53 (m, 2H); 2.58 (m, 2H); 2.64 (m, 4H); 3.59 (m, 2H); 3.69 (m, 2H); 5.70 (br s, 1H).

EXAMPLE 41

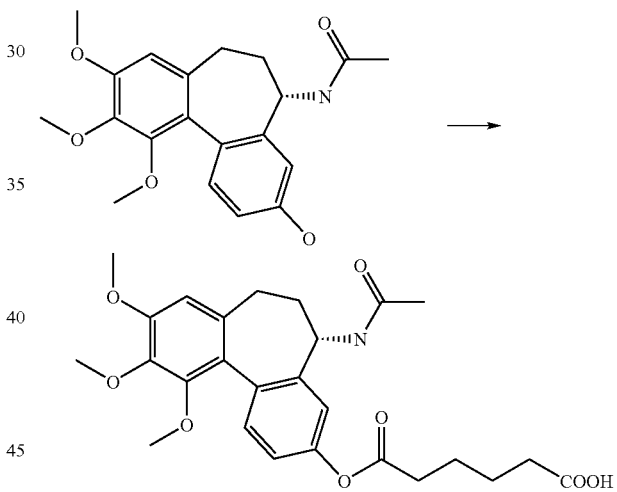

N-Acetyl-colchicinol (0.3 g; 0.84 mmol) was added under argon atmosphere to a solution of adipic acid (0.147 g; 1 mmol, O-(7-(azabenzotriazol-1-yl)-N,N,N',N'-tetramethyluronium hexafluorophosphate (0.383 g; 1 mmol) and diisopropylethylamine (0.352 ml; 2 mmol) in acetonitrile (20 ml). The reaction mixture was stirred at ambient temperature overnight and evaporated to dryness. The residue was taken up in water (4 ml), the pH was adjusted to 6.5 with 0.1M hydrochloric acid. The solution was purified by preparative HPLC eluting with a 0–40% gradient of methanol/ammonium carbonate buffer (2 g/l pH7) to give 5-[{(5S)-5-(acetylamino)-9,10,11-trimethoxy-6,7-dihydro-5H-dibenzo[a,c]cyclohepten-3-yl}oxycarbonyl]pentanoic acid.

Yield: 31%

$^1$H NMR spectrum (DMSOd$_6$): 1.54–1.75 (m, 4H); 1.85–1.90 (m, 1H); 1.87 (s, 3H); 1.98–2.28 (m, 4H); 2.57 (m, 1H, signal partially obscured by DMSO peak); 2.61 (t, 2H); 3.51 (s, 3H); 3.78 (s, 3H); 3.84 (s, 3H); 4.55 (m, 1H); 6.80 (s, 1H); 7.04–7.11 (m, 2H); 7.34 (d, 1H); 8.43 (d, 1H).

MS-ESI: 508 [MNa]$^+$

EXAMPLE 42

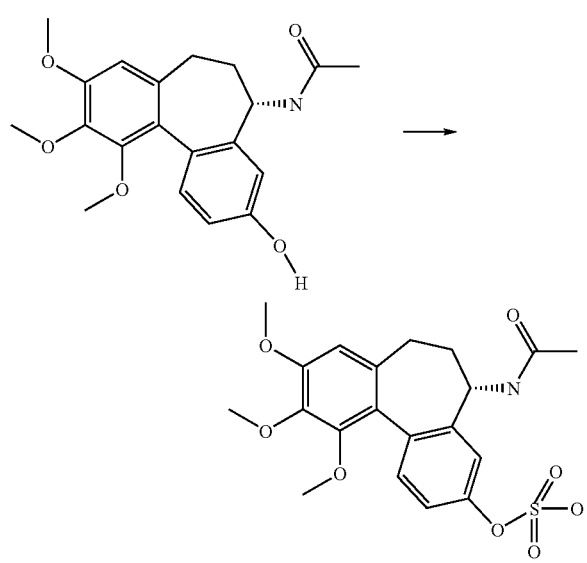

Chlorosulphonic acid (1 ml) was added at 0° C. in portions to a solution of pyridine (10 ml). After 15 minutes at 0° C., a solution of N-acetyl-colchicinol (1 g, 2.8 mmol) in pyridine (10 ml) was added. The solution was stirred overnight at ambient temperature. Water (30 ml) was added and the mixture was adjusted to pH8 by addition of sodium hydrogen carbonate. The aqueous layer was extracted with ether (3×20 ml) and purified on HP20SS resin, eluted with a 0–40% gradient of methanol/water. The volatiles were removed by evaporation to give (5S)-5-(acetylamino)-9,10,11-trimethoxy-6,7-dihydro-5H-dibenzo[a,c]cyclohepten-3-yl hydrogen sulphate as a white solid.

Yield=71%

$^1$H NMR spectrum (DMSOd$_6$): 1.9 (s, 3H), 2–2.2 (m, 2H), 2.5 (m, 1H, signal obscured by DMSO peak), 3.5 (s, 3H), 3.77 (s, 3H), 3.83 (s, 3H), 4.5 (m, 1H), 6.77 (s, 1H), 7.1 (s, 1H), 7.2 (2s, 2H), 8.4 (d, 1H).

MS-ESI: 482 [M Na]$^+$

| Elemental analysis: | Found | C 48.1 H 4.9 N 2.8 S 6.2 |
|---|---|---|
| C$_{20}$H$_{22}$O$_8$NSNa, 2 H$_2$O | Requires | C 48.5 H 5.3 N 2.8 S 6.5% |

EXAMPLE 43

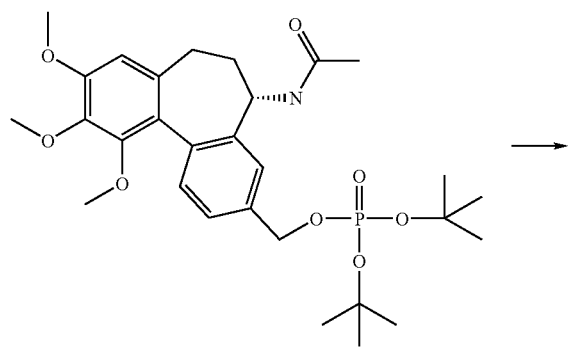

Using an analogous procedure to that described for Example 27 [(5S)-5-(acetylamino)-9,10,11-trimethoxy-6,7-dihydro-5H-dibenzo[a,c]cyclohepten-3-yl]methyl ditertbutyl phosphate was treated with 1M hydrogen chloride in 1,4-dioxane to give [(5S)-5-(acetylamino)-9,10,11-trimethoxy-6,7-dihydro-5H-dibenzo[a,c]cyclohepten-3-yl] methyl dihydrogen phosphate.

Yield: 95%

The sodium salt was prepared by addition of 2N sodium hydroxide to a suspension of [(5S)-5-(acetylamino)-9,10,11-trimethoxy-6,7-dihydro-5H-dibenzo[a,c]cyclohepten-3-yl] methyl dihydrogen phosphate in water until the mixture was at pH7. After freeze-drying, the sodium salt was obtained as a white solid.

$^1$H NMR Spectrum (D$_2$O): 1.94 (m, 1H); 1.98 (s, 3H); 2.15 (m, 1H); 2.25 (m, 1H); 2.50 (m, 1H); 3.50 (s, 3H); 3.80 (s, 3H); 3.84 (s, 3H); 4.48 (m, 1H); 4.80 (m, 2H); 6.80 (s, 1H); 7.40 (m, 3H).

MS-ESI: 496 [MH]$^+$

The starting material was prepared as follows:

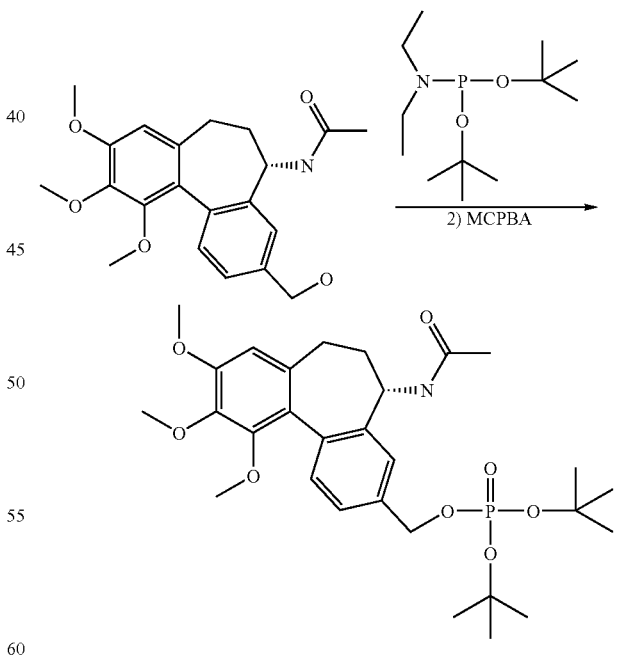

Using an analogous procedure to that described for the starting material in Example 27, N-[(5S)-3-hydroxymethyl-9,10,11-trimethoxy-6,7-dihydro-5H-dibenzo[a,c]cyclohepten-5-yl]acetamide, (prepared as described in Example 25), was reacted with di-tert-butyl diethylphosphoramidite to give [(5S)-5-(acetylamino)-9,10,11-trimethoxy-6,7-dihydro-5H-dibenzo[a,c]cyclohepten-3-yl]methyl ditertbutyl phosphate.

Yield: 59%

¹H NMR spectrum (DMSOd₆): 1.432 (s, 9H); 1.435 (s, 9H); 1.88 (s, 3H); 1.90 (m, 1H); 2.02 (m, 1H); 2.18 (m, 1H); 2.5 (m, 1H, signal obscured by DMSO peak); 3.50 (s, 3H); 3.79 (s, 3H); 3.85 (s, 3H); 4.56 (m, 1H); 4.97 (d, 2H); 6.81 (s, 1H); 7.35 (m, 2H); 7.38 (s, 1H); 8.46 (d, 1H).

EXAMPLE 44

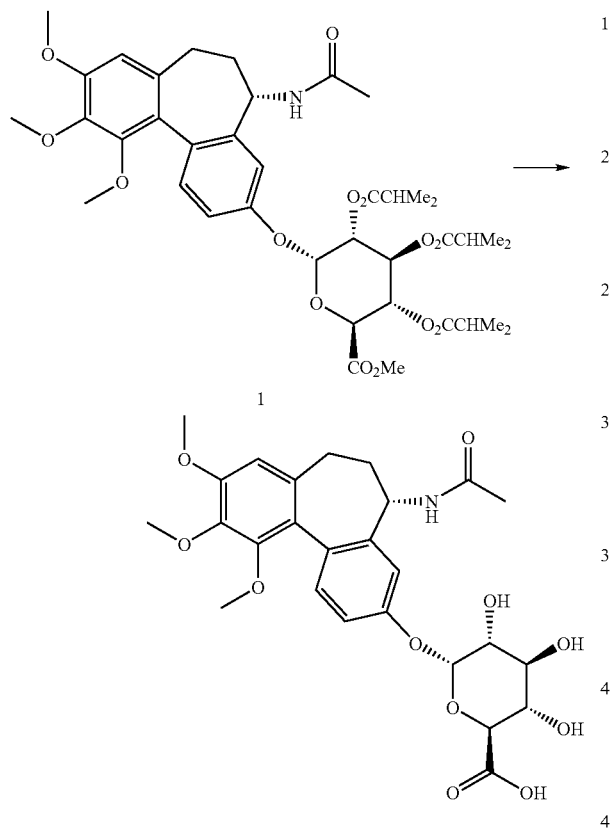

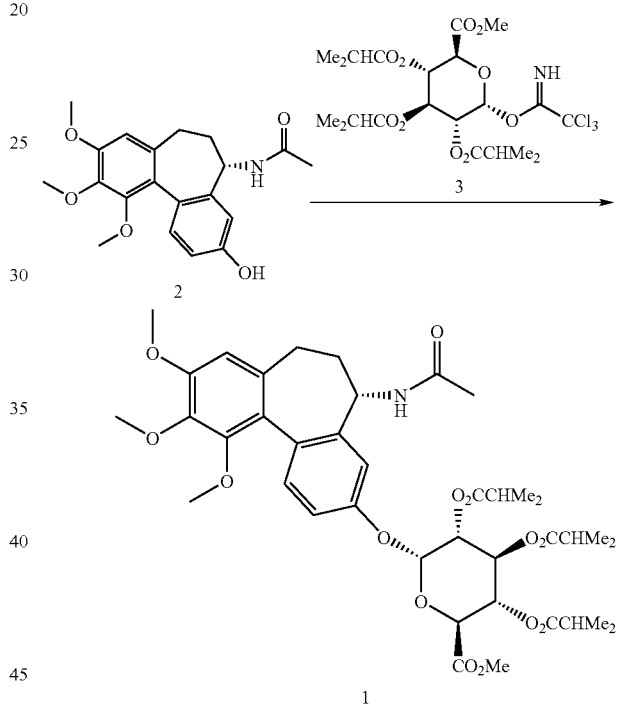

cyclohepten-3-yl]oxy}-3,4,5-trihydroxytetrahydro-2H-pyran-2-carboxylic acid as a white solid (260 mg).

Yield: 68%

¹H NMR spectrum (DMSOd₆, CF₃CO₂D): 1.88 (m, 1H); 1.89 (s, 3H); 2.08 (m, 1H); 2.15 (m, 1H); 2.52 (m, 1H, signal obscured partially by DMSO peak); 3.25–3.36 (m, 3H); 3.44 (t, 1H); 3.51 (s, 3H); 3.78 (s, 3H); 3.84 (s, 3H); 3.91 (d, 1H); 4.50 (m, 1H); 5.03 (d, 1H); 6.77 (s, 1H); 6.98 (s, 1H); 7.00 (d, 1H); 7.26 (d, 1H).

MS-ESI: 534 [MH]⁺

| Elemental analysis | Found | C 55.7 H 6.1 N 2.5 |
|---|---|---|
| C₂₆H₃₁NO₁₁; 1.5 H₂O | Requires | C 56.0 H 5.9 N 2.6% |

The starting material was prepared as follows:

A solution of methyl (2S,3R,4S,5R,6R)-6-[(5S)-5-(acetylamino)-9,10,11-trimethoxy-6,7-dihydro-5H-dibenzo[a,c]cyclohepten-3-yl]oxy-3,4,5-tris(isobutyryloxy)tetrahydro-2H-pyran-2-carboxylate (1) (515 mg; 0.68 mol) in methanol (10 ml) and water (1 ml) was treated with lithium hydroxide monohydrate (214 mg; 5.1 mmol). The reaction mixture was stirred at ambient temperature and additional solution of lithium hydroxide monohydrate (86 mg; 2 mmol) in H₂O (1 ml) was added after 12 hours and then again after a further 10 hours hours to complete the reaction. After a total of 30 hours at ambient temperature, the methanol was removed and the remaining solution was adjusted to pH6 with 2N hydrochloric acid. The resulting heterogeneous solution was deposited on a column of HP2O SS resin (35 ml) for purification, eluting with a 0 to 75% aqueous solution of methanol. After removal of the solvents by evaporation, the solid was purified further by preparative HPLC on reverse phase silica eluting with a 0–50% gradient of methanol/water to give, after removal of the methanol by evaporation and freeze drying, (2S,3S,4S,5R,6R)-6-{[(5S)-5-(acetylamino)-9,10,11-trimethoxy-6,7-dihydro-5H-dibenzo[a,c]

Freshly distilled boron trifluoride-diethyl ether (0.22 ml; 1.7 mmol) was added at 0° C. under argon atmosphere to a stirred solution of N-acetyl-colchicinol (2) (303 mg; 0.85 mmol) and methyl (trichloroacetimidoyl 2,3,4-tri-O-isobutyryl-α-D-glucopyranosid) uronate (3) (955 mg; 1.7 mmol), (THL 36, 8601, 1995), in dichloromethane (8 ml). The mixture was stirred at 0° C. for 15 minutes and then at ambient temperature for 2 hours. The reaction mixture was diluted with dichloromethane, washed with aqueous saturated sodium hydrogen carbonate, water, then dried (MgSO₄) and evaporated. The residue was purified by flash chromatography eluting with a 0 to 35% gradient of dichloromethane/ether to give, after evaporation, (1) as a light yellow-green foam.

Yield: 82%

¹H NMR spectrum (DMSOd₆+CD₃CO₂D): 1.01–1.06 (m, 18H); 1.87 (m, 1H); 1.89 (s, 3H); 2.13 (m, 1H); 2.26 (m, 1H); 2.50 (m, 4H, signal obscured partially by DMSO peak); 3.50 (s, 3H); 3.65 (s, 3H); 3.78 (s, 3H); 3.83 (s, 3H); 4.58 (m, 1H); 4.74 (d, 1H); 5.11 (t, 1H); 5.17 (d, 1H); 5.60 (t, 1H); 5.73 (d, 1H); 6.77 (s, 1H); 6.94 (s, 1H); 6.95 (d, 1H); 7.28 (d, 1H); 8.37 (d, 1H).

MS-ESI: 758 [MH]+

EXAMPLE 45

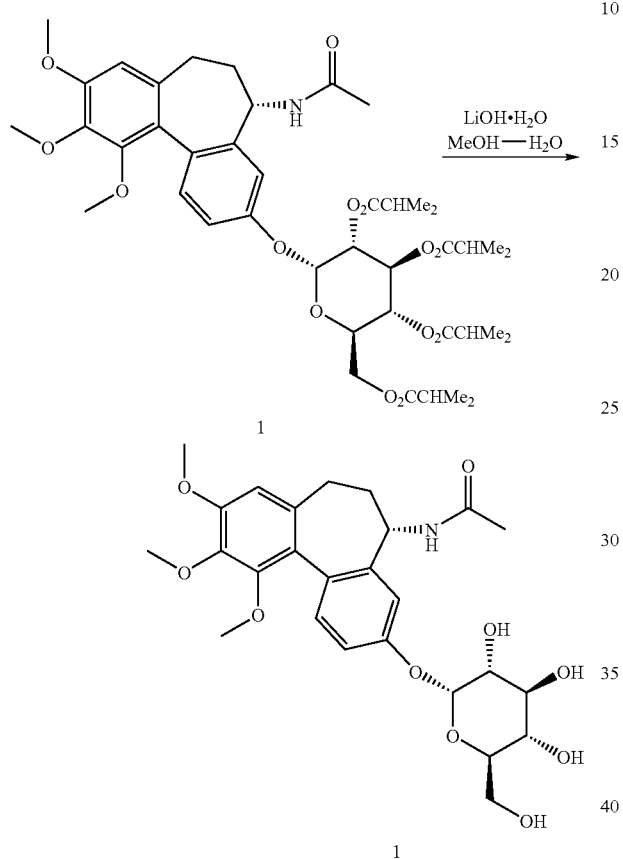

(2R,3R,4S,5R,6R)-2-[(5S)-5-(Acetylamino)-9,10,11-trimethoxy-6,7-dihydro-5H-dibenzo[a,c]cyclohepten-3-yl]oxy-3,5-bis(isobutyryloxy)-6-[(isobutyryloxy)methyl]tetrahydro-2H-pyran-4-yl 2-methylpropanoate (1) (304 mg; 0.38 mmol) and H₂O (0.25 ml) were added to a 0.48M solution of lithium hydroxide monohydrate in methanol (6 ml). The mixture was stirred at ambient temperature for 6 hours. After removal of the methanol by evaporation, the remaining aqueous solution was adjusted to pH6.2 with 2N hydrochloric acid. The resulting heterogeneous solution was deposited on a column of HP2O SS resin (35 ml) for purification, eluting with a 0–60% gradient of methanol/water. After concentration and freeze drying N-((5S)-9,10,11-trimethoxy-3-[(2R,3R,4S,5S,6R)-3,4,5-trihydroxy-6-(hydroxymethyl)tetrahydro-2H-pyran-2-yl]oxy-6,7-dihydro-5H-dibenzo[a,c]cyclohepten-5-yl) acetamide was obtained as a white solid (180 mg).

Yield: 84%

¹H NMR spectrum (DMSOd₆, CF₃CO₂D): 1.88 (m, 1H); 1.90 (s, 3H); 2.10 (m, 1H); 2.18 (m, 1H); 2.52 (m, 1H, signal obscured partially by DMSO peak); 3.21–3.37 (m, 4H); 3.51 (s, 3H); 3.48–3.58 (m, 1H); 3.74–3.81 (m, 1H); 3.80 (s, 3H); 3.84 (s, 3H); 4.50 (m, 1H); 4.92 (d, 1H); 6.78 (s, 1H); 6.98 (d, 1H); 7.00 (dd, 1H); 7.26 (d, 1H); 8.36 (d, 1H).

MS-ESI: 542 [MNa]+

| Elemental analysis | Found | C 55.3 H 6.6 N 2.6 |
| C₂₆H₃₃NO₁₀ 2.6 H₂O | Required | C 55.1 H 6.8 N 2.5% |

The starting material was prepared as follows:

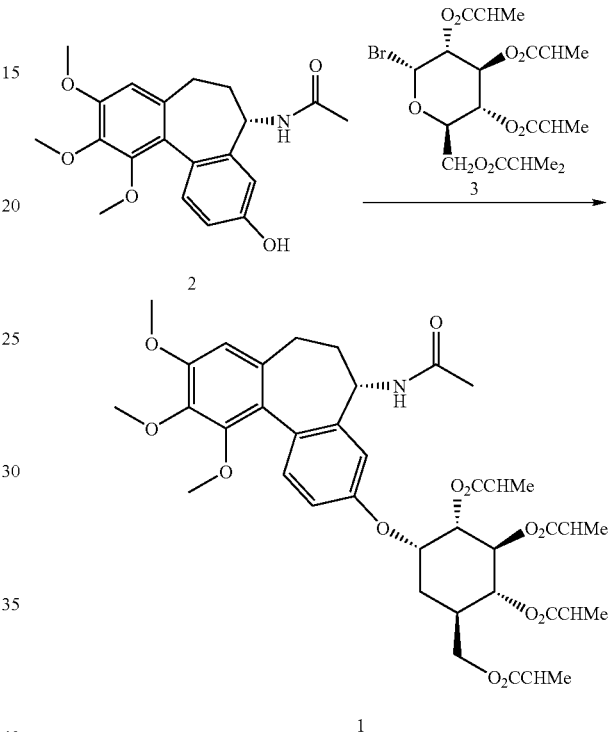

N-Benzyltributylammomium bromide (523 mg; 1 mmol) and N-acetyl-colchicinol (2) (357 mg; 1 mmol) in a 1.25N aqueous solution of sodium hydroxide were added at 0° C. to a solution of the (2R,3R,4S,5S,6R)-2-bromo-3,5-bis(isobutyryloxy)-6-[(isobutyryloxy)methyl]tetrahydro-2H-pyran-4-yl 2-methylpropanoate (3) (523 mg; 1 mmol), (J. Chem. Soc. Perkins Trans. 1 1995 p 577), in trichloromethane (2 ml). After 1 hour the reaction mixture was stirred at ambient temperature. Additional reagent (3) (250 mg; 0.48 mmol and 1.33 mg; 0.33 mmol) and 1.25N sodium hydroxide (0.2 ml and 0.1 ml) were added to the reaction mixture after 6 hours at ambient temperature and then again after a further 14 hours at ambient temperature. After a total of 24 hours, the reaction mixture was diluted with dichloromethane, washed successively with water, brine and then dried (MgSO₄). After removal of the solvent, the residue was purified by flash chromatography eluting with dichloromethane/ether (8/2 to 6/4) to give (1) (320 mg) as a foam.

Yield: 40%

¹H NMR spectrum (DMSOd₆): 1.00–1.11 (m, 24H); 1.88 (m, 1H); 1.89 (s, 3H); 2.08 (m, 1H); 2.21 (m, 1H); 2.46–2.66 (m, 5H, signal obscured partially by DMSO peak); 3.48 (s, 3H); 377 (s, 3H); 3.83 (s, 3H); 4.16–4.24 (m, 2H); 4.32 (m, 1H); 4.47 (m, 1H); 5.08 (m, 2H); 5.54 (t, 1H); 5.67 (d, 1H); 6.77 (s, 1H); 6.92 (d, 1H); 6.95 (dd, 1H); 7.25 (d, 1H); 8.38 (d, 1H).

MS-ESI: 800 [MH]+

EXAMPLE 46

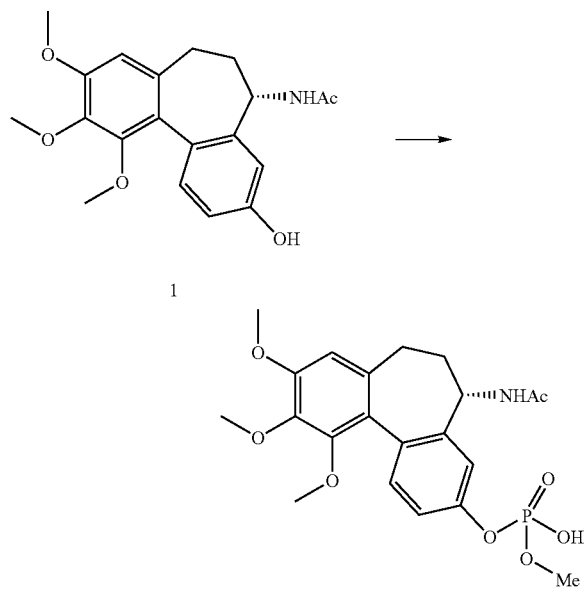

A solution of N-acetyl-colchicinol (1) (0.45 g; 1.26 mmol) in THF (40 ml) under argon was cooled to 0° C. and treated with a 1.0M solution of lithiumHMDS in THF (1.39 ml; 1.39 mmol). The mixture was stirred at 0° C. for 1 hour and then added in portions over about 15 minutes to a solution of methyl dichlorophosphate (625 µl; 4.16 mmol) in THF (150 ml). The mixture was stirred at ambient temperature for 15 minutes. After addition of water (200 ml) the THF was removed by evaporation. After removal of the insoluble material by filtration, the filtrate was purified on HP20 SS resin eluting with a gradient of 0–60% methanol/water. The appropriate fractions were freeze-dried to give (5S)-5-(acetylamino)-9,10,11-trimethoxy-6,7-dihydro-5H-dibenzo[a,c]cyclohepten-3-yl methyl hydrogen phosphate as white solid (391 mg).

Yield: 69%

$^1$H NMR spectrum (DMSO $d_6$; $CF_3CO_2D$): 1.89 (s, 3H); 1.9 (m, 1H); 2.05 (m, 1H); 2.18 (m, 1H); 2.5 (m, 1H, signal obscured partially by DMSO peak); 3.53 (s, 3H); 3.73 (d, 3H); 3.79 (s, 3H); 3.84 (s, 3H); 4.51 (m, 1H); 6.79 (s, 1H); 7.14 (d, 1H); 7.15 (s, 1H); 7.32 (d, 1H); 8.46 (d, 1H).

MS-ESI: 451 [MH]$^+$

| Elemental analysis: | Found | C 54.1 | H 5.9 | N 3.1 |
|---|---|---|---|---|
| $C_{21}H_{26}NO_8P$; 0.7 $H_2O$ | Requires | C 54.2 | H 6.0 | N 3.0% |

EXAMPLE 47

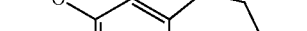

A solution of N-acetyl-colchicinol (1) (0.36 g; 1.0 mmol) in THF (40 ml) under argon was cooled to 0° C. and treated with a 1.0M solution of lithiumHMDS in THF (1.1 ml; 1.1 mmol). The mixture was stirred at 0° C. for 1 hour and then added in portions over about 2 hours to a solution of ethyl dichlorophosphate (400 µl; 3.3 mmol) in THF (150 ml). The mixture was stirred at ambient temperature for 15 minutes. After addition of water (200 ml) the THF was removed by evaporation. After removal of the insoluble material by filtration, the filtrate was purified on HP20 SS resin eluting with a gradient of 0–60% methanol/water. The appropriate fractions were freeze-dried to give (5S)-5-(acetylamino)-9,10,11-trimethoxy-6,7-dihydro-5H-dibenzo[a,c]cyclohepten-3-yl ethyl hydrogen phosphate as a white solid (259 mg).

Yield: 56%

$^1$H NMR spectrum (DMSO $d_6$; $CF_3CO_2D$): 1.25 (dt, 3H); 1.89 (s, 3H); 1.9 (m, 1H); 2.05 (m, 1H); 2.19 (m, 1H); 2.5 (m, 1H, signal obscured partially by DMSO peak); 3.53 (s, 3H); 3.79 (s, 3H); 3.85 (s, 3H); 4.09 (m, 2H); 4.52 (m, 1H); 6.80 (s, 1H); 7.13 (d, 1H); 7.15 (s, 1H); 7.32 (d, 1H); 8.45 (d, 1H).

MS-ESI: 466 [MH]$^+$

| Elemental analysis: | Found | C 54.6 | H 6.0 | N 3.0 |
|---|---|---|---|---|
| $C_{22}H_{28}NO_8P$; 1.0 $H_2O$ | Requires | C 54.7 | H 6.3 | N 2.9% |

EXAMPLE 48

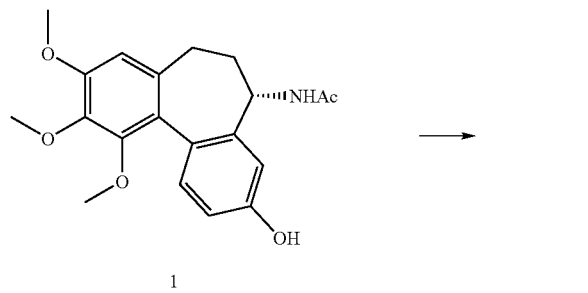

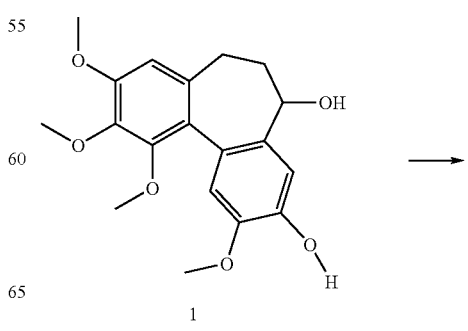

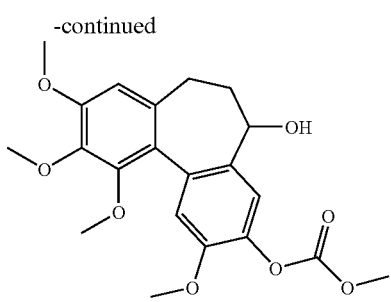

Triethylamine (140 μl; 1.0 mmol) and methyl chloroformate (80 μl; 1.0 mmol) were added to a solution of 5-hydroxy-2,9,10,11-tetramethoxy-6,7-dihydro-5H-dibenzo[a,c]cyclohepten-3-ol (1) (0.18 g; 0.5 mmol) in THF (10 ml). The mixture was stirred at ambient temperature overnight. After removal of the insoluble material by filtration the residue was purified by flash chromatography eluting with increasingly polar mixtures of ethyl acetate/hexanes (5 to 60% ethyl acetate) to give 5-hydroxy-2,9,10,11-tetramethoxy-6,7-dihydro-5H-dibenzo[a,c]cyclohepten-3-yl methyl carbonate as a hard oil/white solid (163 mg).

Yield: 81%

$^1$H NMR spectrum (CDCl$_3$): 1.89 (m, 1H); 2.39 (m, 2H); 2.54 (m, 1H); 3.61 (s, 3H); 3.87 (s, 3H); 3.91 (s, 3H); 3.92 (s, 3H); 3.93 (s, 3H); 4.56 (m, 1H); 6.59 (s, 1H); 7.15 (s, 1H); 7.45 (s, 1H).

MS-ESI: 427 [MNa]$^+$

EXAMPLE 49

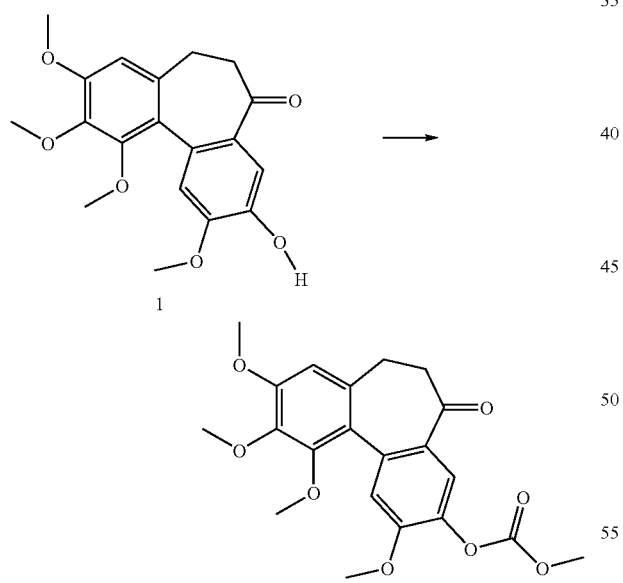

Triethylamine (35 μl; 0.225 mmol) and methyl chloroformate (20 μl; 0.225 mmol) were added to a solution of 3-hydroxy-2,9,10,11-tetramethoxy-6,7-dihydro-5H-dibenzo[a,c]cyclohepten-5-one (1) (0.052 g; 0.15 mmol) in THF (5 ml). The mixture was stirred at ambient temperature for 5 hours. After removal of the insoluble material by filtration the residue was purified by flash chromatography eluting with increasingly polar mixtures of ethyl acetate/hexanes (0 to 100% ethyl acetate) to give methyl 2,9,10,11-tetramethoxy-5-oxo-6,7-dihydro-5H-dibenzo[a,c]cyclohepten-3-yl carbonate as a white solid (57 mg).

Yield: 95%

$^1$H NMR spectrum (CDCl$_3$): 2.69 (m, 1H); 2.85 (m, 1H); 2.97 (m, 1H); 3.16 (m, 1H); 3.53 (s, 3H); 3.93 (s, 3H); 3.94 (s, 3H); 3.94 (s, 3H); 3.95 (s, 3H); 6.64 (s, 1H); 7.24 (s, 1H); 7.47 (s, 1H).

MS-ESI: 403 [MH]$^+$

| Elemental analysis: | Found | C 62.0 | H 5.5 |
| --- | --- | --- | --- |
| C$_{21}$H$_{22}$O$_8$; 0.2 H$_2$O | Requires | C 62.1 | H 5.6% |

The starting material was prepared as follows:

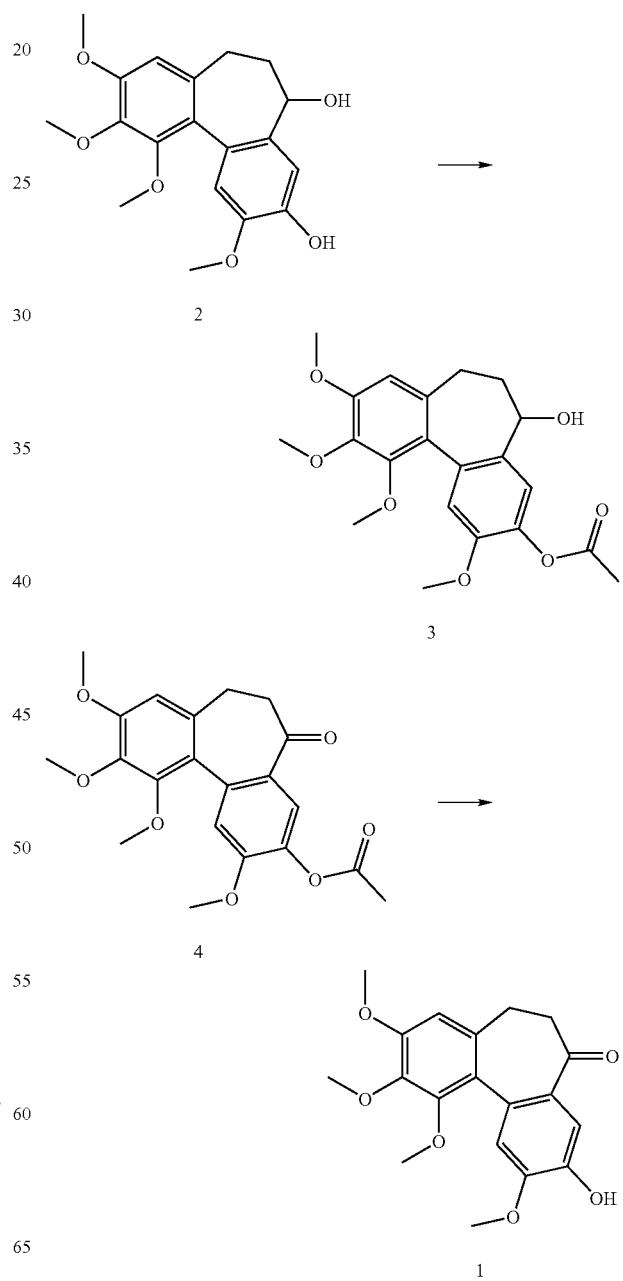

Triethylamine (1.05 ml; 7.5 mmol) and acetyl chloride (540 µl; 7.5 mmol) were added to a solution of 5-hydroxy-2,9,10,11-tetramethoxy-6,7-dihydro-5H-dibenzo[a,c]cyclohepten-3-ol (2) (1.05 g; 3.0 mmol) in THF (50 ml). The mixture was stirred at ambient temperature overnight. After removal of the insoluble material by filtration the residue was purified by flash chromatography eluting with increasingly polar mixtures of ethyl acetate/hexanes (0 to 100% ethyl acetate) to give methyl 5-hydroxy-2,9,10,11-tetramethoxy-6,7-dihydro-5H-dibenzo[a,c]cyclohepten-3-yl carboxylate (3) as a white solid (880 mg).

Yield: 76%

$^1$H NMR spectrum (CDCl$_3$): 1.89 (m, 1H); 2.34 (s, 3H); 2.38 (m, 2H); 2.53 (m, 1H); 3.61 (s, 3H); 3.84 (s, 3H); 3.90 (s, 3H); 3.91 (s, 3H); 4.55 (m, 1H); 6.59 (s, 1H); 7.14 (s, 1H); 7.35 (s, 1H).

MS-ESI: 411 [MNa]$^+$

| Elemental analysis: | Found | C 65.0 | H 6.3 |
|---|---|---|---|
| C$_{21}$H$_{24}$O$_7$ | Requires | C 64.9 | H 6.2% |

A solution of (3) (0.776 g; 2.0 mmol) in dichloromethane (30 ml) was added to a solution of Collins Reagent (3.1 g; 12.0 mmol) in dichloromethane (30 ml). The mixture was stirred at ambient temperature for 30 minutes. After removal of the insoluble material by filtration the filtrate was washed with 2N hydrochloric acid, then brine and dried over MgSO$_4$. The residue was purified by flash chromatography eluting with increasingly polar mixtures of ethyl acetate/hexanes (0 to 60% ethyl acetate) to give methyl 5-oxo-2,9,10,11-tetramethoxy-6,7-dihydro-5H-dibenzo[a,c]cyclohepten-3-yl carboxylate (4) as a white solid (706 mg).

Yield: 91%

$^1$H NMR spectrum (CDCl$_3$): 2.34 (s, 3H); 2.64 (m, 1H); 2.82 (m, 1H); 2.93 (m, 1H); 3.14 (m, 1H); 3.50 (s, 3H); 3.88 (s, 3H); 3.91 (s, 3H); 3.92 (s, 3H); 6.61 (s, 1H); 7.20 (s, 1H); 7.36 (s, 1H).

MS-ESI: 387 [MH]$^+$

| Elemental analysis: | Found | C 65.6 | H 6.0 |
|---|---|---|---|
| C$_{21}$H$_{22}$O$_7$ | Requires | C 65.3 | H 5.7% |

Water (10 ml) and saturated aqueous sodium hydrogen carbonate (10 ml) were added to a solution of (4) (0.58 g; 1.5 mmol) in methanol (50 ml). The mixture was stirred at ambient temperature overnight. After dilution with ethyl acetate the organic phase was washed with 2N hydrochloric acid, then brine and dried over MgSO$_4$. The residue was triturated with ether and hexanes to give (1) as a white solid (441 mg).

Yield: 85%

$^1$H NMR spectrum (CDCl$_3$): 2.61 (m, 1H); 2.80 (m, 1H); 2.91 (m, 1H); 3.06 (m, 1H); 3.45 (s, 3H); 3.88 (s, 3H); 3.88 (s, 3H); 3.91 (s, 3H); 5.73 (s br, 1H); 6.58 (s, 1H); 7.09 (s, 1H); 7.17 (s, 1H).

MS-ESI: 345 [MH]$^+$

| Elemental analysis: | Found | C 65.52 | H 6.10 |
|---|---|---|---|
| C$_{19}$H$_{20}$O$_6$; 0.2 H$_2$O | Requires | C 65.58 | H 5.91 |

EXAMPLE 50

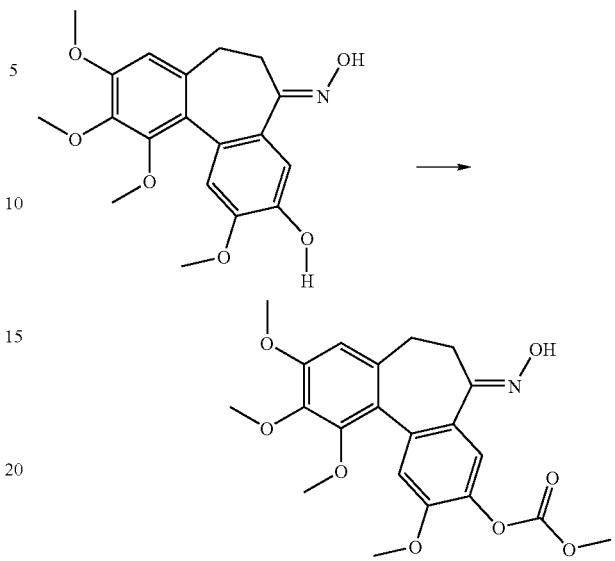

Triethylamine (18 µl; 0.12 mmol) and methyl chloroformate (10 µl; 0.12 mmol) were added to a solution of 5-(hydroxyimino)-2,9,10,11-tetramethoxy-6,7-dihydro-5H-dibenzo[a,c]cyclohepten-3-ol (1) (0.035 g; 0.1 mmol) in THF (3 ml). The mixture was stirred at ambient temperature overnight. After removal of the insoluble material by filtration the residue was purified by flash chromatography eluting with increasingly polar mixtures of ethyl acetate/hexanes (0 to 100% ethyl acetate) to give 5-(hydroxyimino)-2,9,10,11-tetramethoxy-6,7-dihydro-5H-dibenzo[a,c]cyclohepten-3-yl methyl carbonate (E isomer) as a white solid (22 mg), followed by the second (Z) isomer (7 mg).

Yield: 54%

$^1$H NMR spectrum (CDCl$_3$): 2.59 (m, 1H); 2.82 (m, 2H); 3.20 (m, 1H); 3.51 (s, 3H); 3.88 (s, 3H); 3.90 (s, 3H); 3.91 (s, 3H); 3.93 (s 3H); 6.59 (s, 1H); 7.21 (s, 1H); 7.26 (s, 1H); 8.61 (br s, 1H).

MS-ESI: 418 [MH]$^+$

| Elemental analysis: | Found | C 58.1 | H 5.7 | N 3.0 |
|---|---|---|---|---|
| C$_{21}$H$_{23}$NO$_8$; 0.8 H$_2$O | Requires | C 58.4 | H 5.7 | N 3.2% |

The starting material was prepared as follows:

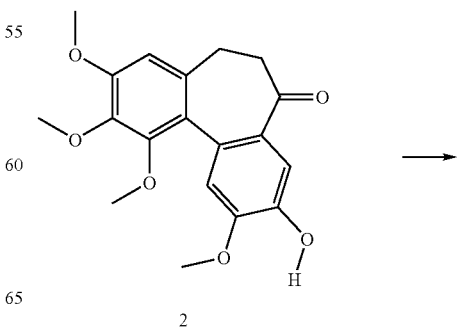

2

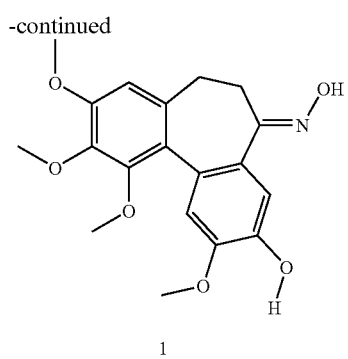

Hydroxylamine hydrochloride (70 mg; 1.0 mmol) was added to a solution of 3-hydroxy-2,9,10,11-tetramethoxy-6,7-dihydro-5H-dibenzo[a,c]cyclohepten-5-one (2) (0.172 g; 0.5 mmol) in pyridine (3.0 ml). The mixture was stirred at ambient temperature overnight. After dilution with 2N hydrochloric acid and extraction with ethyl acetate, the organic phase was washed with 2N hydrochloric acid, then brine and dried over $MgSO_4$. The residue was triturated with ether and hexanes to give (1) (a 3:1 mixture of E:Z isomers) as a white solid (170 mg).

Yield: 95%

$^1$H NMR spectrum (CDCl$_3$), major isomer: 2.56 (m, 1H); 2.66–2.9 (m, 2H); 3.18 (m, 1H); 3.45 (s, 3H); 3.86 (s, 3H); 3.88 (s, 3H); 3.89 (s, 3H); 6.55 (s, 1H); 7.08 (s, 1H); 7.24 (s, 1H).

MS-ESI: 360 [MH]$^+$

| Elemental analysis: | Found | C 62.6 | H 6.3 | N 3.6 |
|---|---|---|---|---|
| $C_{19}H_{21}NO_6$; 0.3 H$_2$O | Requires | C 62.6 | H 6.0 | N 3.8% |

EXAMPLE 51

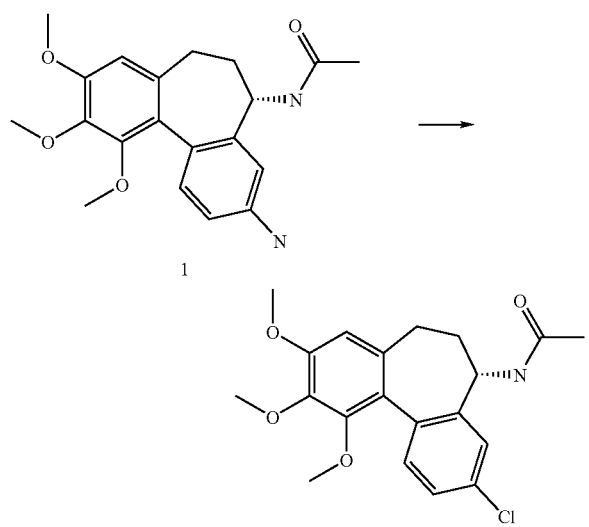

A solution of N-[(5S)-3-amino-9,10,11-trimethoxy-6,7-dihydro-5H-dibenzo[a,c]cyclohepten-5-yl]acetamide (0.712 g; 2 mmol) in ethanol (3.75 ml) and 36% hydrochloric acid (1.57 ml) was slowly added into a mixture of ice (6 ml) and 36% hydrochloric acid (1.57 ml). At 0° C. a solution of sodium nitrite (0.14 g; 2 mmol) in water (0.25 ml) was added. The mixture was stirred at 0° C. for 1 hour and then transferred into a separate flask containing a solution of copper(I) chloride (0.218 g; 2.2 mmol) in water (0.35 ml) and 36% hydrochloric acid (0.4 ml). The resulting mixture was stirred at 30° C. for 30 minutes and extracted with toluene/ethyl acetate (50/50). The organic phase was washed with water, dilute sodium hydroxide, and saturated sodium chloride solution, then dried and the volatiles were removed by evaporation. The residue was purified by flash chromatography eluting with ethyl acetate to give N-[(5S)-3-chloro-9,10,11-trimethoxy-6,7-dihydro-5H-dibenzo[a,c]cyclohepten-5-yl]acetamide.

Yield: 46%.

$^1$H NMR Spectrum (DMSOd$_6$): 1.89 (s, 3H); 1.90 (m, 1H); 2.02 (m, 1H); 2.15 (m, 1H); 2.5 (m, 1H); 3.50 (s, 3H); 3.78 (s, 3H); 3.84 (s, 3H); 4.52 (m, 1H); 6.80 (s, 1H); 7.35 (m, 3H); 8.43 (d, 1H).

MS-ESI: 398 [MNa]$^+$

EXAMPLE 52

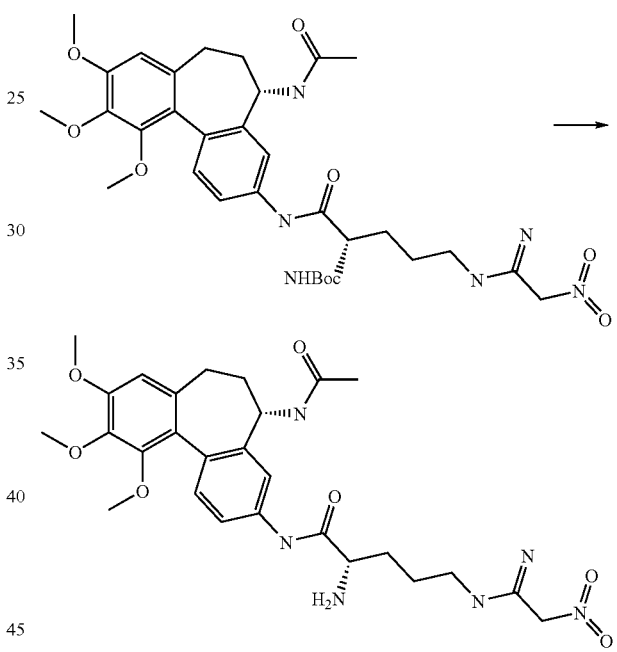

A solution of (2S)-N-[(5S)-5-(acetylamino)-9,10,11-trimethoxy-6,7-dihydro-5H-dibenzo[a,c]cyclohepten-3-yl]-2-(N-tertbutoxycarbonylamino)-5-[(2-nitroethanimidoyl)amino]pentanamide (1) (0.15 g, 0.28 mmol) in dichloromethane (2 ml) was treated at 0° C. with TFA (2 ml). The mixture was stirred at ambient temperature for 2 hours and evaporated. The residue was taken up in methanol/dichloromethane and evaporated to give an oil which was triturated in ether to give (2S)-N-[(5S)-5-(acetylamino)-9,10,11-trimethoxy-6,7-dihydro-5H-dibenzo[a,c]cyclohepten-3-yl]-2-amino-5-[(2-nitroethanimidoyl)amino]pentanamide as a solid.

Yield: 95%

$^1$H NMR spectrum (DMSOd$_6$): 1.60 (m, 2H); 1.83 (m, 2H); 1.90 (s, 3H); 1.92 (m, 1H); 2.06 (m, 1H); 2.20 (m, 1H); 2.5 (m, 1H; signal obscured by DMSO Peak); 3.22 (m, 2H); 3.50 (s, 3H); 3.79 (s, 3H); 3.85 (s, 3H); 3.95 (m, 1H); 4.48 (m, 1H); 6.80 (s, 1H); 7.32 (d, (1H); 7.45 (d, 1H); 7.75 (dd, 1H); 8.45 (d, 1H).

MS-ESI: 558 [MH]$^+$

| Elemental analysis | Found | C 48.1 H 5.7 N 13.2 |
| --- | --- | --- |
| C₂₆H₃₅N₇O₇; 1.4 TFA; 0.5 methanol | Requires | C 48.0 H 5.3 N 13.4% |

The starting material was prepared as follows:

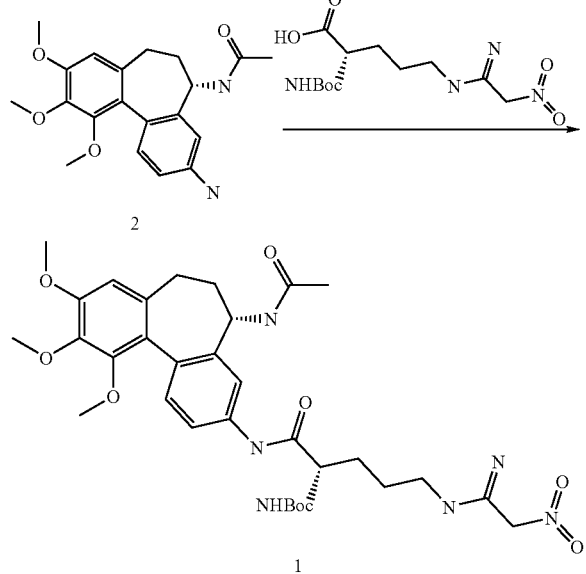

A solution of N-[(5S)-3-amino-9,10,11-trimethoxy-6,7-dihydro-5H-dibenzo[a,c]cyclohepten-5-yl]acetamide (2) (0.45 g; 1.26 mmol), Nα-tert-butoxycarbonyl-ω-nitro-L-arginine (50.402 g; 1.26 mmol), EDCI (0.312 g; 1.63 mmol) and DMAP (0.03 g; 0.25 mmol) in dichloromethane (18 ml) was stirred at ambient temperature overnight. After addition of water (2 ml) and extraction, the organic phase was evaporated to give an oil which was purified by flash chromatography eluting with ethyl acetate/methanol (95/5) to give (1).

Yield: 28%

$^1$H NMR (DMSOd₆): 1.38 (m, 2H); 1.40 (s, 9H); 1.60 (m, 2H); 1.90 (s, 3H); 1.91 (m, 1H); 2.15 (m, 2H); 2.5 (m, 2H, signal obscured by DMSO peak); 3.20 (m, 2H); 3.48 (s, 3H); 3.79 (s, 3H); 3.84 (s, 3H); 4.13 (m, 1H); 4.50 (m, 1H); 6.80 (s, 1H); 7.10 (d, 1H); 7.27 (d, 2H); 7.55 (s, 1H); 7.62 (d, 1H); 8.40 (d, 1H).

MS-ESI: 658 [MH]$^+$

EXAMPLE 53

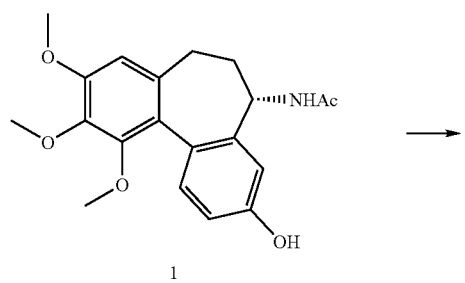

A solution of N-acetyl-colchicinol (0.36 g; 1.0 mmol) in THF (40 ml) under argon was cooled to 0° C. and treated with a 1.0M solution of lithiumHMDS in THF (1.1 ml; 1.1 mmol). The mixture was stirred at 0° C. for 1 hour and then added in portions over about 2 hours to a solution of methylphosphonic dichloride (0.53 mg; 4.0 mmol) in THF (150 ml). The mixture was stirred at ambient temperature for 15 minutes. After addition of water (200 ml) the THF was removed by evaporation. After removal of the insoluble material by filtration, the filtrate was purified on HP20 SS resin eluting with a gradient of 0–60% methanol/water. The methanol was removed by evaporation and the mixture was adjusted to pH7.14 with sodium hydroxide (0.1 M). The appropriate fractions were freeze-dried to give (5S)-5-(acetylamino)-9,10,11-trimethoxy-6,7-dihydro-5H-dibenzo[a,c]cyclohepten-3-yl hydrogen methylphosphonate as a beige solid (180 mg).

Yield: 41%

$^1$H NMR spectrum (DMSO d₆; CF₃CO₂D): 1.53 (d, 3H); 1.88 (s, 3H); 1.9 (m, 1H); 2.06 (m, 1H); 2.16 (m, 1H); 2.5 (m, 1H, signal obscured partially by DMSO peak); 3.52 (s, 3H); 3.78 (s, 3H); 3.84 (s, 3H); 4.51 (m, 1H); 6.79 (s, 1H); 7.13 (s, 1H); 7.14 (d, 1H); 7.30 d, 1H); 8.45 (d, 1H).

MS-ESI: 458 [MNa]$^+$

EXAMPLE 54

The following illustrate representative pharmaceutical dosage forms containing the compound of formula I, or a pharmaceutically acceptable salt thereof (hereafter compound X), for therapeutic or prophylactic use in humans:

| (a) | Tablet I | mg/tablet |
| --- | --- | --- |
|  | Compound X | 100 |
|  | Lactose Ph.Eur | 182.75 |
|  | Croscarmellose sodium | 12.0 |
|  | Maize starch paste (5% w/v paste) | 2.25 |
|  | Magnesium stearate | 3.0 |
| (b) | Tablet II | mg/tablet |
|  | Compound X | 50 |
|  | Lactose Ph.Eur | 223.75 |
|  | Croscarmellose sodium | 6.0 |
|  | Maize starch | 15.0 |
|  | Polyvinylpyrrolidone (5% w/v paste) | 2.25 |
|  | Magnesium stearate | 3.0 |
| (c) | Tablet III | mg/tablet |
|  | Compound X | 1.0 |
|  | Lactose Ph.Eur | 93.25 |
|  | Croscarmellose sodium | 4.0 |
|  | Maize starch paste (5% w/v paste) | 0.75 |
|  | Magnesium stearate | 1.0 |

-continued

| (d) | Capsule | mg/capsule |
|---|---|---|
| | Compound X | 10 |
| | Lactose Ph.Eur | 488.5 |
| | Magnesium stearate | 1.5 |
| (e) | Injection I | (50 mg/ml) |
| | Compound X | 5.0% w/v |
| | 1M Sodium hydroxide solution | 15.0% v/v |
| | 0.1M Hydrochloric acid (to adjust pH to 7.6) | |
| | Polyethylene glycol 400 | 4.5% w/v |
| | Water for injection to 100% | |
| (f) | Injection II | 10 mg/ml |
| | Compound X | 1.0% w/v |
| | Sodium phosphate BP | 3.6% w/v |
| | 0.1M Sodium hydroxide solution | 15.0% v/v |
| | Water for injection to 100% | |
| (g) | Injection III | (1 mg/ml, buffered to pH 6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of the formula IIa:

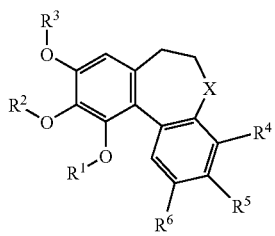

wherein

X is —CH($R^7$)— wherein $R^7$ is hydrogen, hydroxy, $C_{1-7}$alkoxy, —$OR^8$ or —$NR^8R^9$, wherein $R^8$ is a group —$Y^1R^{10}$, wherein $Y^1$ is a direct bond, —C(O)—, —C(S)—, —S—, —C(O)O—, —C(O)$NR^{11}$—, —$SO_2$— or —$SO_2NR^{12}$— (wherein $R^{11}$ and $R^{12}$, which may be the same or different, each independently represents hydrogen, $C_{1-3}$alkyl or $C_{1-3}$alkoxy$C_{2-3}$alkyl) and $R^{10}$ is selected from one of the following nine groups:
1) hydrogen, $C_{1-7}$alkyl, $C_{3-7}$cycloalkyl, $C_{1-4}$alkyl$Y^8$ $C_{1-4}$alkyl wherein $Y^8$ is as defined herein, or phenyl, which alkyl, cycloalkyl, alkyl$Y^8$alkyl or phenyl group may bear one or more substituents selected from: halogeno, amino, $C_{1-4}$alkylamino, di($C_{1-4}$alkyl)amino, hydroxy, carboxy, carbamoyl, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, phenyl, nitro, sulphate, phosphate, $Z^1$, wherein $Z^1$ represents a 5–6 membered saturated heterocyclic group (linked via carbon or nitrogen) with 1–2 heteroatoms, selected independently from O, S and N, which heterocyclic group may bear 1 or 2 substituents selected from oxo, hydroxy, halogeno, $C_{1-4}$alkyl, $C_{1-4}$hydroxyalkyl, $C_{1-4}$alkoxy, $C_{1-4}$aminoalkyl, $C_{1-7}$alkanoyl, cyano$C_{1-4}$alkyl, $C_{1-4}$alkoxy $C_{1-4}$alkyl, $C_{1-4}$alkylsulphonyl$C_{1-4}$alkyl, $C_{1-4}$alkyl$Z^1$ (wherein $Z^1$ is as defined herein), and a group —$Y^2R^{13}$, wherein $Y^2$ is —$NR^{14}$C(O)— or —O—C(O)— (wherein $R^{14}$ represents hydrogen, $C_{1-3}$alkyl or $C_{1-3}$alkoxy$C_{2-3}$alkyl) and $R^{13}$ is $C_{1-7}$alkyl, $C_{3-7}$cycloalkyl or a group $R^{15}$ wherein $R^{15}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{16}R^{17}$ and —$NR^{18}COR^{19}$ (wherein $R^{16}$, $R^{17}$, $R^{18}$ and $R^{19}$, which may be the same or different, each represents hydrogen, $C_{1-3}$alkyl or $C_{1-3}$alkoxy$C_{2-3}$alkyl);

2) $R^{15}$ wherein $R^{15}$ is as defined herein;
3) $C_{2-7}$alkenyl$R^{15}$ (wherein $R^{15}$ is as defined herein);
4) $C_{3-7}$alkynyl$R^{15}$ (wherein $R^{15}$ is as defined herein);
5) $Z^1$ (wherein $Z^1$ is as defined herein);
6) $C_{1-7}$alkyl$Z^1$ (wherein $Z^1$ is as defined herein);
7) $C_{1-7}$alkyl$Y^8Z^1$, wherein $Z^1$ is as defined herein and $Y^8$ is —C(O)—, —$NR^{59}$C(O)—, —$NR^{59}$C(O)$C_{1-4}$alkyl-, —C(O)$NR^{60}$— or —C(O)$NR^{60}$ $C_{1-4}$alkyl-, (wherein $R^{59}$ and $R^{60}$, which may be the same or different, each represents hydrogen, $C_{1-3}$alkyl, $C_{1-3}$hydroxyalkyl or $C_{1-3}$alkoxy $C_{2-3}$alkyl);

8) ($C_{1-7}$alkyl)$_cY^9Z^3$, wherein c is 0 or 1, $Z^3$ is an amino acid group and $Y^9$ is a direct bond, —C(O)— or —$NR^{61}$— (wherein $R^{61}$ is hydrogen, $C_{1-3}$alkyl or $C_{1-3}$alkoxy $C_{2-3}$alkyl); and 9) $C_{1-7}$alkyl$R^{15}$ (wherein $R^{15}$ is as defined herein); and $R^9$ is hydrogen, $C_{1-7}$alkyl or $C_{3-7}$cycloalkyl, which alkyl or cycloalkyl group may bear one or more substituents selected from $C_{1-4}$alkoxy and phenyl;

$R^1$, $R^2$ and $R^3$ are each independently hydrogen, $PO_3H_2$, sulphate, $C_{3-7}$cycloalkyl, $C_{2-7}$alkenyl, $C_{2-7}$alkynyl, $C_{1-7}$alkanoyl, a group $R^{20}C_{1-7}$alkyl (wherein $R^{20}$ is phenyl which may bear one or more substituents selected from $C_{1-4}$alkyl, $C_{1-4}$alkoxy, $C_{1-4}$aminoalkyl and $C_{1-4}$hydroxyalkoxy), $C_{1-7}$alkyl or $C_{1-7}$alkylsulphonyl, which alkyl or alkylsulphonyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^2R^{21}$, wherein $Y^2$ is —$NR^{22}C(O)$— or —O—C(O)— (wherein $R^{22}$ represents hydrogen, $C_{1-3}$alkyl or $C_{1-3}$alkoxy$C_{2-3}$alkyl) and $R^{21}$ is $C_{1-7}$alkyl, $C_{3-7}$cycloalkyl or a group $R^{23}$ wherein $R^{23}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{24}R^{25}$ and —$NR^{26}COR^{27}$ (wherein $R^{24}$, $R^{25}$, $R^{26}$ and $R^{27}$, which may be the same or different, each represents hydrogen, $C_{1-3}$alkyl or $C_{1-3}$alkoxy$C_{2-3}$alkyl);

with the proviso that at least two of $R^1$, $R^2$ and $R^3$ are $C_{1-7}$alkyl;

$R^4$ is hydrogen, cyano, halogeno, nitro, amino, hydroxy, $C_{1-7}$alkoxy, $C_{1-7}$thioalkoxy, $C_{1-7}$alkanoyl or $C_{1-7}$alkyl, which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^3R^{28}$, wherein $Y^3$ is —$NR^{29}C(O)$— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl);

$R^5$ and $R^6$ are each independently selected from hydrogen, —$OPO_3H_2$, phosphonate, cyano, halogeno, nitro, amino, carboxy, carbamoyl, hydroxy, $C_{1-7}$alkoxy, $C_{1-7}$alkanoyl, $C_{1-7}$thioalkoxy, $C_{1-7}$alkyl, which alkyl group may bear one or more substituents selected from: halogeno, amino, $C_{1-4}$alkylamino, di($C_{1-4}$alkyl)amino, hydroxy, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, sulphate, phosphate and a group —$Y^3R^{28}$, wherein $Y^3$ is —$NR^{29}C(O)$— or —O—C(O)— (wherein $R^{29}$ represents hydrogen, $C_{1-3}$alkyl or $C_{1-3}$alkoxy$C_{2-3}$alkyl) and $R^{28}$ is $C_{1-7}$alkyl, $C_{3-7}$cycloalkyl or a group $R^{30}$ wherein $R^{30}$ is a phenyl group or a 5–10-membered aromatic heterocyclic group (linked via carbon or nitrogen) with 1–4 heteroatoms selected independently from O, N and S, which phenyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{31}R^{32}$ and —$NR^{31}COR^{32}$ (wherein $R^{31}$, $R^{32}$, $R^{33}$ and $R^{34}$, which may be the same or different, each represents hydrogen, $C_{1-3}$alkyl or $C_{1-3}$alkoxy$C_{2-3}$alkyl), and a group —$Y^4R^{35}$, wherein $Y^4$ is —C(O)—, —OC(O)—, —O—, —SO—, —$SO_2$—, —$OSO_2$—, —$NR^{36}$—, —$C_{1-4}$alkyl$NR^{36}$—, —$C_{1-4}$alkylC(O)—, —$NR^{37}C(O)$—, —OC(O)O—, —$C(O)NR^{38}$— or —$NR^{39}C(O)O$— (wherein $R^{36}$, $R^{37}$, $R^{38}$ and $R^{39}$, which may be the same or different, each represents hydrogen, $C_{1-3}$alkyl or $C_{1-3}$alkoxy$C_{2-3}$alkyl) and $R^{35}$ is a sugar moiety, a mono-peptide, a di-peptide, a tri-peptide, a tetra-peptide, sulphate, hydroxy, amino, $C_{1-7}$alkyl, $C_{1-7}$alkoxy, $C_{1-7}$alkanoyl, $C_{1-7}$alkylamino, di($C_{1-7}$alkyl)amino, amino $C_{1-7}$alkylamino, $C_{1-7}$alkylamino$C_{1-7}$alkylamino, $C_{1-7}$alkanoylamino$C_{1-7}$alkyl, di($C_{1-7}$alkyl)amino $C_{1-7}$alkylamino, $C_{1-7}$alkylphosphate, $C_{1-7}$alkylphosphonate, $C_{1-7}$alkylcarbamoyl$C_{1-7}$alkyl, which alkyl, alkoxy, alkanoyl, alkylamino, dialkylamino, aminoalkylamino, alkylaminoalkylamino, alkanoylaminoalkyl, dialkylaminoalkylamino, alkylphosphate, alkylphosphate or alkylcarbamoylalkyl, may bear one or more substituents selected from: halogeno, amino, $C_{1-4}$alkylamino, di($C_{1-4}$alkyl)amino, hydroxy, $C_{1-4}$hydroxyalkyl, $C_{1-4}$alkoxy, $C_{1-4}$alkylsulphanyl, $C_{1-4}$alkylsulphonyl, $C_{1-4}$alkoxycarbonylamino, $C_{1-4}$alkanoyl, carboxy, phenyl, nitro, sulphate, phosphate and a group —$Y^5R^{40}$, wherein $Y^5$ is —$NR^{41}C(O)$—, —$C(O)NR^{42}$—, —C(O)—O— or —O—C(O)— (wherein $R^{41}$ and $R^{42}$ which may be the same or different each represents hydrogen, $C_{1-3}$alkyl or $C_{1-3}$alkoxy$C_{2-3}$alkyl) and $R^{40}$ is $C_{1-7}$alkyl, $C_{3-7}$cycloalkyl, carboxy$C_{1-7}$alkyl or a group $R^{43}$ wherein $R^{43}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, —$CONR^{44}R^{45}$ and —$NR^{46}COR^{47}$ (wherein $R^{44}$, $R^{45}$, $R^{46}$ and $R^{47}$, which may be the same or different, each represents hydrogen, $C_{1-3}$alkyl or $C_{1-3}$alkoxy$C_{2-3}$alkyl), $R^{48}$, wherein $R^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from hydroxy, nitro, halogeno, amino, $C_{1-4}$alkyl, $C_{1-4}$haloalkyl, $C_{1-4}$alkoxy, $C_{1-4}$hydroxyalkyl, $C_{1-4}$aminoalkyl, $C_{1-4}$alkylamino, di($C_{1-4}$alkyl)amino, di($C_{1-4}$alkyl)amino$C_{1-4}$alkyl, di($C_{1-4}$hydroxyalkyl)amino$C_{1-4}$alkyl, di($C_{1-4}$aminoalkyl)amino$C_{1-4}$alkyl, $C_{1-4}$hydroxyalkoxy, carboxy, $C_{1-4}$carboxyalkyl, phenyl, cyano, —$CONR^{49}R^{50}$, —$NR^{51}COR^{52}$ (wherein $R^{49}$, $R^{50}$, $R^{51}$ and $R^{52}$, which may be the same or different, each represents hydrogen, $C_{1-3}$alkyl or $C_{1-3}$alkoxy$C_{2-3}$alkyl) and $C_{1-4}$alkyl$R^{53}$ (wherein $R^{53}$ is as defined herein), $C_{1-7}$alkyl$R^{48}$ (wherein $R^{48}$ is as defined herein),
$R^{53}$, wherein $R^{53}$ is a 5–6-membered saturated heterocyclic group (linked via carbon or nitrogen) with 1–2 heteroatoms, selected independently from O, S and N, which heterocyclic group may bear 1 or 2 substituents selected from
oxo, hydroxy, halogeno, $C_{1-4}$alkyl, $C_{1-4}$hydroxyalkyl, $C_{1-4}$alkoxy, $C_{1-4}$carboxyalkyl, $C_{1-4}$aminoalkyl, di($C_{1-4}$alkyl)amino$C_{1-4}$alkyl, $C_{1-4}$alkoxy$C_{1-4}$alkyl, $C_{1-4}$alkylsulphonyl$C_{1-4}$alkyl and $R^{54}$, wherein $R^{54}$ is a 5–6-membered saturated heterocyclic group (linked via carbon or nitrogen) with 1–2 heteroatoms, selected independently from O, S and N, which heterocyclic group may bear 1 or 2 substituents selected from
oxo, hydroxy, halogeno, $C_{1-4}$alkyl, $C_{1-4}$hydroxyalkyl, $C_{1-4}$alkoxy, $C_{1-4}$alkoxy$C_{1-4}$alkyl and $C_{1-4}$alkylsulphonyl$C_{1-4}$alkyl, or
$(CH_2)_a Y^6 (CH_2)_b R^{53}$, wherein
$R^{53}$ is as defined herein, a is 0, or an integer 1–4, b is 0 or an integer 1–4 and
$Y^6$ represents a direct bond, —O—, —C(O)—, —NR$^{55}$—, —NR$^{56}$C(O)— or —C(O)NR$^{57}$— (wherein $R^{55}$, $R^{56}$, and $R^{57}$, which may be the same or different, each represents hydrogen, $C_{1-3}$alkyl or $C_{1-3}$alkoxy$C_{2-3}$alkyl),
and wherein one or more of the $(CH_2)_a$ or $(CH_2)_b$ groups may bear one or more substituents selected from hydroxy, amino and halogeno;
with the proviso that $R^5$ is not hydroxy, alkoxy, substituted alkoxy (wherein $R^5$ is $Y^4R^{35}$ and $Y^4$ is —O— and $R^{35}$ is $C_{1-7}$alkyl bearing one or more substituents selected from the list given herein), —OPO$_3$H$_2$, —O—$C_{1-7}$alkanoyl or benzyloxy;
with the further proviso that at least one of $R^5$ or $R^6$ is a group —$Y^4R^{35}$ (wherein $Y^4$ and $R^{35}$ are as defined herein) but with the further provisos
that when $R^5$ is —$Y^4R^{35}$ and $R^6$ is hydrogen, hydroxy, methoxy or methoxycarbonyl, —$Y^4R^{35}$ is not selected from cases wherein:
$Y^4$ is —C(O)—, —OC(O)—, —O—, —SO—, —OSO$_2$—, —NR$^{36}$—, —NR$^{37}$C(O)— or —C(O)NR$^{38}$— (wherein $R^{36}$, $R^{37}$ and $R^{38}$, which may be the same or different, each represents hydrogen, $C_{1-3}$alkyl or $C_{1-3}$alkoxy$C_{2-3}$alkyl) and
$R^{35}$ is a glycine, valine or lysine group, a dipeptide of glycine and valine groups, $C_{1-7}$alkyl, $C_{1-7}$alkoxy, $C_{1-7}$alkanoyl, (which alkyl, alkoxy or alkanoyl may bear one or more substituents selected from: halogeno, hydroxy, and a group —$Y^5R^{40}$ (wherein $Y^5$ is —O—C(O)— and $R^{40}$ is $C_{1-7}$alkyl), or $R^{48}$, wherein $R^{48}$ is a tetrazolyl group (which may or may not be substituted as herein defined), a phenyl group or a benzyl group which phenyl or benzyl group may bear one or more substituents selected from $C_{1-4}$alkyl; and
that when $R^6$ is —$Y^4R^{35}$ and $R^5$ is hydrogen, methoxy or methoxycarbonyl, —$Y^4R^{35}$ is not selected from cases wherein:
$Y^4$ is —C(O)—, —O— or —OSO$_2$— and
$R^{35}$ is $C_{1-7}$alkyl, $C_{1-7}$alkoxy (which alkyl, alkoxy or alkanoyl may bear one or more substituents selected from: halogeno), $R^{48}$ (wherein $R^{48}$ is a benzyl group which benzyl group may bear one or more substituents selected from $C_{1-4}$alkyl), or $R^{53}$ (wherein $R^{53}$ is piperidinyl);
or a salt thereof.

2. A compound according to claim 1 wherein
X is —CH($R^7$)—, wherein
$R^7$ is —OR$^8$ or —NR$^8$R$^9$, wherein $R^8$ is a group —$Y^1R^{10}$ (wherein $Y^1$ is —C(O)—, —C(O)O— or —C(O)NR$^{11}$— (wherein $R^{11}$ represents hydrogen, $C_{1-3}$alkyl or $C_{1-3}$alkoxy$C_{2-3}$alkyl) and $R^{10}$ is as defined in claim 1) and $R^9$ is as defined in claim 1.

3. A compound according to claim 1 wherein $R^1$, $R^2$ and $R^3$ are each methyl.

4. A compound according to claim 1 wherein $R^4$ is hydrogen.

5. A compound according to claim 1 wherein $R^6$ is hydrogen, halogeno, amino, carboxy, hydroxy, $C_{1-7}$alkoxy or a group $Y^4R^{35}$, wherein
$Y^4$ is —C(O)—, —O— or —OSO$_2$— and
$R^{35}$ is $C_{1-7}$alkyl, $C_{1-7}$alkoxy (which alkyl or alkoxy may bear one or more substituents selected from halogeno), $R^{48}$ (wherein $R^{48}$ is a benzyl group) or $R^{53}$ (wherein $R^{53}$ is a 5–6-membered saturated heterocyclic group (linked via carbon or nitrogen) with 1–2 heteroatoms selected independently from O, S and N).

6. A compound according to claim 1 wherein $R^6$ is hydrogen, C(O)OCH$_3$ or methoxy.

7. A compound according to claim 1 wherein
$R^5$ is hydrogen, halogeno, amino, carboxy, carbamoyl, $C_{1-7}$alkanoyl, $C_{1-7}$thioalkoxy, or a group —$Y^4R^{35}$, wherein
$Y^4$ is —C(O)—, —OC(O)—, —O—, —SO—, —OSO$_2$—, —NR$^{36}$—, —NR$^{37}$C(O)— or —C(O)NR$^{38}$— (wherein $R^{36}$, $R^{37}$ and $R^{38}$, which may be the same or different, each represents hydrogen, $C_{1-3}$alkyl or $C_{1-3}$alkoxy$C_{2-3}$alkyl) and
$R^{35}$ is a sugar moiety, a mono-peptide, a di-peptide, a tri-peptide, a tetra-peptide, $C_{1-7}$alkyl, $C_{1-7}$alkoxy, $C_{1-7}$alkanoyl, $C_{1-7}$alkanoylamino$C_{1-7}$alkyl,
which alkyl, alkoxy, alkanoyl, alkanoylaminoalkyl may bear one or more substituents selected from: halogeno, amino, hydroxy, carboxy, and a group —$Y^5R^{40}$, wherein
$Y^5$ is —C(O)—O— or —O—C(O)— and
$R^{40}$ is $C_{1-7}$alkyl or a group $R^{43}$ wherein $R^{43}$ is a benzyl group,
$R^{48}$, wherein $R^{48}$ is a phenyl group, a benzyl group or a 5–10-membered aromatic heterocyclic group (linked via carbon or nitrogen) with 1–4 heteroatoms selected independently from O, N and S, which phenyl, benzyl or aromatic heterocyclic group may bear one or more substituents selected from
hydroxy, fluoro, amino, $C_{1-4}$alkoxy, $C_{1-4}$hydroxyalkyl, $C_{1-4}$aminoalkyl, $C_{1-4}$alkylamino, di($C_{1-4}$alkyl)amino, di($C_{1-4}$alkyl)amino$C_{1-4}$alkyl, di($C_{1-4}$hydroxyalkyl)amino$C_{1-4}$alkyl, di($C_{1-4}$aminoalkyl)amino$C_{1-4}$alkyl, $C_{1-4}$hydroxyalkoxy, carboxy, $C_{1-4}$carboxyalkyl, cyano, —CONR$^{49}$R$^{50}$, —NR$^{51}$COR$^{52}$ (wherein $R^{49}$, $R^{50}$, $R^{51}$ and $R^{52}$, which may be the same or different, each represents hydrogen, $C_{1-3}$alkyl or $C_{1-3}$alkoxy$C_{2-3}$alkyl) and $C_{1-4}$alkyl$R^{53}$ (wherein $R^{53}$ is as defined herein), $C_{1-7}$alkyl$R^{48}$ (wherein $R^{48}$ is as defined herein), $R^{53}$, wherein
$R^{53}$ is a 5–6-membered saturated heterocyclic group (linked via carbon or nitrogen) with 1–2 heteroatoms, selected independently from O, S and N, which heterocyclic group may bear 1 or 2 substituents selected from
oxo, hydroxy, fluoro, chloro, $C_{1-4}$alkyl, $C_{1-4}$hydroxyalkyl, $C_{1-4}$alkoxy, $C_{1-4}$carboxyalkyl, C$_{1-4}$aminoalkyl, di(C$_{1-4}$alkyl)aminoC$_{1-4}$alkyl, C$_{1-4}$alkoxyC$_{1-4}$alkyl, C$_{1-4}$alkylsulphonylC$_{1-4}$alkyl and R$^{54}$, wherein R$^{54}$ is a 5–6-membered saturated heterocyclic group (linked via carbon or nitrogen) with 1–2 heteroatoms, selected independently form O, S and N, which heterocyclic group may bear 1 or 2 substituents selected from
oxo, hydroxy, halogeno, C$_{1-4}$alkyl, C$_{1-4}$hydroxyalkyl, C$_{1-4}$alkoxy, C$_{1-4}$alkoxyC$_{1-4}$alkyl and C$_{1-4}$alkylsulphonylC$_{1-4}$alkyl, or
(CH$_2$)$_a$Y$^6$(CH$_2$)$_b$R$^{53}$, wherein
R$^{53}$ is as defined herein,
a is 0, or an integer 1–4,
b is 0 or an integer 1–4 and
Y$^6$ represents a direct bond, —O—, —C(O)—, —NR$^{55}$—, —NR$^{56}$C(O)— or —C(O)NR$^{57}$— (wherein R$^{55}$, R$^{56}$, and R$^{57}$, which may be the same or different, each represents hydrogen, C$_{1-3}$alkyl or C$_{1-3}$alkoxyC$_{2-3}$alkyl),
and wherein one or more of the (CH$_2$)$_a$ or (CH$_2$)$_b$ groups may bear one or more substituents selected from hydroxy, amino and halogeno;
with the proviso that R$^5$ is not alkoxy, substituted alkoxy (wherein R$^5$ is Y$^4$R$^{35}$ and Y$^4$ is —O— and R$^{35}$ is C$_{1-7}$alkyl bearing one or more substituents selected from the list given herein), —O—C$_{1-7}$alkanoyl or benzyloxy.

8. A compound according to claim 1 selected from:
(5S)-5-(acetylamino)-9,10,11-trimethoxy-6,7-dihydro-5H-dibenzo[a,c]cyclohepten-3-yl 3-{[(2R)-2,6-diaminohexanoyl]amino}propanoate,
(5S)-5-(acetylamino)-9,10,11-trimethoxy-6,7-dihydro-5H-dibenzo[a,c]cyclohepten-3-yl 3-[(2-aminoacetyl)amino]propanoate,
N-([(5S)-5-(acetylamino)-9,10,11-trimethoxy-6,7-dihydro-5H-dibenzo[a,c]cyclohepten-3-yl]oxymethyl)-2-morpholinoacetamide,
(2S,3S,4S,5R,6R)-6-{[(5S)-5-(acetylamino)-9,10,11-trimethoxy-6,7-dihydro-5H-dibenzo[a,c]cyclohepten-3-yl]oxy}-3,4,5-trihydroxytetrahydro-2H-pyran-2-carboxylic acid,
N-[(5S)-3-(4-{4-methylpiperazin-1-ylmethyl}phenylcarbonyloxy)-9,10,11-trimethoxy-6,7-dihydro-5H-dibenzo[a,c]cyclohepten-5-yl]acetamide,
N-[(5S)-3-(4-{morpholinomethyl}phenylcarbonyloxy)-9,10,11-trimethoxy-6,7-dihydro-5H-dibenzo[a,c]cyclohepten-5-yl]acetamide,
(5S)-5-(acetylamino)-9,10,11-trimethoxy-6,7-dihydro-5H-dibenzo[a,c]cyclohepten-3-yl 3-[4-methylpiperazin-1-ylcarbonyl]propanoate,
5-[{(5S)-5-(acetylamino)-9,10,11-trimethoxy-6,7-dihydro-5H-dibenzo[a,c]cyclohepten-3-yl}oxycarbonyl]pentanoic acid,
4-(3-[(5S)-5-(acetylamino)-9,10,11-trimethoxy-6,7-dihydro-5H-dibenzo[a,c]cyclohepten-3-yl]oxy-3-oxopropyl)benzoic acid and
(2S)-N-[(5S)-5-(acetylamino)-9,10,11-trimethoxy-6,7-dihydro-5H-dibenzo[a,c]cyclohepten-3-yl]-2-amino-3-hydroxypropanamide,
and salts thereof.

9. A compound according to claim 1 selected from N-[(5S)-3-(4-{4-methylpiperazin-1-ylmethyl}phenylcarbonyloxy)-9,10,11-trimethoxy-6,7-dihydro-5H-dibenzo[a,c]cyclohepten-5-yl]acetamide and (2S)-N-[(5S)-5-(acetylamino)-9,10,11-trimethoxy-6,7-dihydro-5H-dibenzo[a,c]cyclohepten-3-yl]-2-amino-3-hydroxypropanamide,
and salts thereof.

10. A compound according to claim 1 selected from (2S)-N-[(5S)-5-(acetylamino)-9,10,11-trimethoxy-6,7-dihydro-5H-dibenzo[a,c]cyclohepten-3-yl]-2-amino-5-[(2-nitroethanimidoyl)amino]pentanamide
and salts thereof.

11. A process for the manufacture of a compound of formula IIa as defined in claim 1 which comprises:
(a) for the preparation of compounds of formula IIa and salts thereof in which R$^5$ or R$^6$ is a group Y$^4$R$^{35}$ (wherein R$^{35}$ is as defined in claim 1 and Y$^4$ is a group —OC(O)— or —NHC(O)—), the reaction of a compound of formula III or IV:

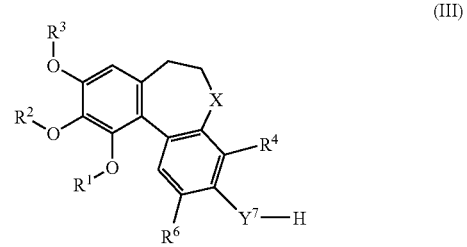

(III)

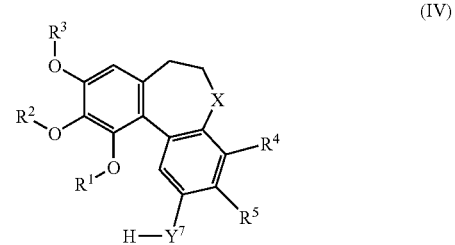

(IV)

(wherein X, R$^1$, R$^2$, R$^3$, R$^4$, R$^5$, R$^6$ are as defined in claim 1 and Y$^7$ is —O— or —NH—), by acylation or coupling reactions;
(b) for the preparation of compounds of formula IIa and salts thereof in which R$^5$ or R$^6$ is a group Y$^4$R$^{35}$ (wherein R$^{35}$ is C$_{1-7}$alkoxy which may be substituted as defined in claim 1 and Y$^4$ is a group —OC(O)— or —NHC(O)—), the reaction of a compound of formula III and IV, by acylation reactions;
(c) for the preparation of compounds of formula IIa and salts thereof in which R$^5$ or R$^6$ is a group Y$^4$R$^{35}$ (wherein R$^{35}$ is aminoC$_{1-7}$alkylamino, C$_{1-7}$alkylaminoC$_{1-7}$alkylamino, di(C$_{1-7}$alkyl)aminoC$_{1-7}$alkylamino and may be substituted as defined in claim 1, or is R$^{53}$ (wherein R$^{53}$ is as defined in claim 1) and Y$^4$ is a group —OC(O)— or —NHC(O)—), can be prepared by the reaction of a compound of formula III or IV, acylation reactions;
(d) for the preparation of compounds of formula IIa and salts thereof in which R$^5$ or R$^6$ is a group Y$^4$R$^{35}$ (wherein R$^{35}$ is a sugar moiety and Y$^4$ is a group —O— or —NH—), the reaction of a compound of formula III or IV by glycosylation reactions;
(e) for the preparation of compounds of formula IIa and salts thereof in which R$^5$ or R$^6$ is a group Y$^4$R$^{35}$ (wherein R$^{35}$ is sulphate and Y$^4$ is a group —O— or —NH—), the reaction of a compound of formula III or IV, by sulphonylation reactions;

(f) for the preparation of compounds of formula IIa and salts thereof in which $R^5$ or $R^6$ is a group $Y^4R^{35}$ (wherein $R^{35}$ is $C_{1-7}$alkylphosphate and may be substituted as defined in claim 1 and $Y^4$ is a group —O— or —NH—), the reaction of a compound of formula III or IV, by phosphorylation reactions;

(g) for the preparation of compounds of formula IIa and salts thereof in which $R^5$ is amino the reaction of a carboxylic acid of formula V:

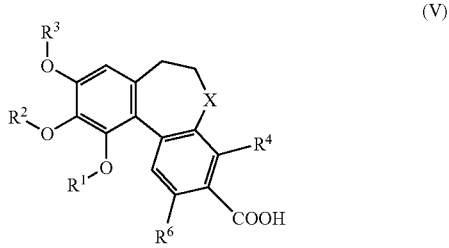

(V)

(wherein X, $R^1$, $R^2$, $R^3$, $R^4$ and $R^6$ are as defined in claim 1) via Curtius rearrangement and hydrolysis; and (h) for the preparation of compounds of formula IIa and salts thereof in which $R^5$ or $R^6$ is chloro the reaction of a compound of formula III or IV by the Sandmeyer reaction;

and when a pharmaceutically acceptable salt of a compound of formula IIa is required, reaction of the compound obtained with an acid or base whereby to obtain the desired pharmaceutically acceptable salt.

12. A pharmaceutical composition which comprises as active ingredient a compound of formula IIa as defined in claim 1 or a pharmaceutically acceptable salt thereof in association with a pharmaceutically acceptable excipient or carrier.

13. A method of reducing neovascularization by selectively damaging newly formed vascular endothelium in a warm-blooded animal in need thereof which comprises administering to said animal an effective amount of a compound of formula IIa or a pharmaceutically acceptable salt thereof as defined in any one of claims 1, 2, 5, 6, 7, 8, 9 and 10.

* * * * *